(12) United States Patent
Karimi et al.

(10) Patent No.: US 10,241,059 B2
(45) Date of Patent: Mar. 26, 2019

(54) WATER-CUT SENSOR SYSTEM

(71) Applicants: Saudi Arabian Oil Company, Dhahran (SA); King Abdullah University of Science and Technology, Thuwal (SA)

(72) Inventors: Muhammad Akram Karimi, Thuwal (SA); Atif Shamim, Thuwal (SA); Muhammad Arsalan, Dhahran (SA)

(73) Assignees: Saudi Arabian Oil Company, Dhahran (SA); King Abdullah University of Science & Technology, Thuwal (SA)

( * ) Notice: Subject to any disclaimer, the term of this patent is extended or adjusted under 35 U.S.C. 154(b) by 84 days.

(21) Appl. No.: 15/686,747

(22) Filed: Aug. 25, 2017

(65) Prior Publication Data

US 2018/0011033 A1 Jan. 11, 2018

Related U.S. Application Data

(63) Continuation-in-part of application No. 14/838,735, filed on Aug. 28, 2015, now Pat. No. 9,804,105.
(Continued)

(51) Int. Cl.
*G01R 27/26* (2006.01)
*G01N 22/04* (2006.01)
*G01N 33/28* (2006.01)

(52) U.S. Cl.
CPC ......... *G01N 22/04* (2013.01); *G01N 33/2823* (2013.01); *G01N 33/2847* (2013.01)

(58) Field of Classification Search
CPC . G01N 22/04; G01N 33/2823; G01N 33/2847
(Continued)

(56) References Cited

U.S. PATENT DOCUMENTS 3,498,112 A 3/1970 Howard
3,635,082 A 1/1972 Prellwitz et al.
(Continued)

FOREIGN PATENT DOCUMENTS

CN 201386555 1/2010
EP 0436286 7/1991
(Continued)

OTHER PUBLICATIONS

International Search Report and Written Opinion for Application No. PCT/US2017/051042; dated Nov. 27, 2017; pp. 1-12.
(Continued)

*Primary Examiner* — Melissa J Koval
*Assistant Examiner* — Courtney G McDonnough
(74) *Attorney, Agent, or Firm* — Bracwell LLP; Constance G. Rhebergen; Christopher L. Drymalla

(57) ABSTRACT

Provided in some embodiments is a method of manufacturing a pipe conformable water-cut sensors system. Provided in some embodiments is method for manufacturing a water-cut sensor system that includes providing a helical T-resonator, a helical ground conductor, and a separator at an exterior of a cylindrical pipe. The helical T-resonator including a feed line, and a helical open shunt stub conductively coupled to the feed line. The helical ground conductor including a helical ground plane opposite the helical open shunt stub and a ground ring conductively coupled to the helical ground plane. The feed line overlapping at least a portion of the ground ring, and the separator disposed between the feed line and the portion of the ground ring overlapped by the feed line to electrically isolate the helical T-resonator from the helical ground conductor.

27 Claims, 25 Drawing Sheets

Related U.S. Application Data

(60) Provisional application No. 62/393,804, filed on Sep. 13, 2016.

(58) Field of Classification Search
USPC .......................................................... 324/634
See application file for complete search history.

(56) References Cited

U.S. PATENT DOCUMENTS

| | | | |
|---|---|---|---|
| 4,499,418 | A | 2/1985 | Helms |
| 4,820,970 | A | 4/1989 | Swanson |
| 4,891,969 | A | 1/1990 | Wayland |
| 4,996,490 | A | 2/1991 | Scott |
| 5,389,883 | A | 2/1995 | Harper |
| 5,485,743 | A | 1/1996 | Taherian et al. |
| 5,864,239 | A | 1/1999 | Adams et al. |
| 5,929,343 | A | 7/1999 | Yamamoto et al. |
| 6,281,801 | B1 | 8/2001 | Cherry et al. |
| 6,441,622 | B1 | 8/2002 | Wrzesinski et al. |
| 6,915,707 | B2 | 6/2005 | Nyfors |
| 7,228,900 | B2 | 6/2007 | Schultz et al. |
| 7,712,381 | B2 | 5/2010 | Allenberg et al. |
| 8,061,186 | B2 | 11/2011 | Gysling |
| 8,225,677 | B2 | 7/2012 | Wang et al. |
| 8,570,050 | B2 | 10/2013 | Nyfors |
| 8,618,817 | B2 | 12/2013 | Jakoby et al. |
| 8,659,293 | B2 | 2/2014 | Krioutchkov et al. |
| 8,855,947 | B2 | 10/2014 | Sheila-Vadde et al. |
| 9,063,052 | B2 | 6/2015 | Folgeroe et al. |
| 9,541,665 | B2 | 1/2017 | Shanks et al. |
| 2007/0224692 | A1 | 9/2007 | Agar |
| 2012/0035858 | A1 | 2/2012 | Caduff et al. |
| 2013/0033272 | A1 | 2/2013 | Folgeroe et al. |
| 2013/0255821 | A1 | 10/2013 | Roberts |
| 2014/0182737 | A1 | 7/2014 | Jones |
| 2014/0260659 | A1 | 9/2014 | Sheila-Vadde et al. |
| 2016/0123899 | A1 | 5/2016 | Harrison et al. |

FOREIGN PATENT DOCUMENTS

| | | |
|---|---|---|
| EP | 2952887 A1 | 12/2015 |
| GB | 2365978 A | 2/2002 |
| WO | 9926316 A1 | 5/1999 |
| WO | 2011133046 A1 | 10/2011 |
| WO | 2012172333 A1 | 12/2012 |
| WO | 2014076506 | 3/2014 |
| WO | 2014064437 A2 | 5/2014 |
| WO | 2015112688 A1 | 7/2015 |

OTHER PUBLICATIONS

International Search Report and Written Opinion for International Application No. PCT/US2017/051045; dated Dec. 7, 2017 (pp. 1-14).

AGAR Corporation, "OW-200 Series Oil/Waler Meters Liquid/Liquid Concentration" available online: http://www.agarcorp.com/literature/ow200.hlml, accessed Aug. 27, 2015, pp. 1-4.

Al-Taweel, "Field Testing of Multiphase Meters" SPE 56585, Society of Petroleum Engineers Inc. Oct. 3-6, 1999, pp. 1-16.

International Search Report and Written Opinion for International Application No. PCT/US2016/048128; dated Dec. 7, 2016 (pp. 1-15).

Dongzhi, "Analysis of Multi-factor influence on Measurement of Water Content in Crude Oil and Its Prediction Model" Proceedings of the 27th Chinese Control Conference, Jul. 16-18, 2008, pp. 430-435.

EESiFlo "Water Cut Meter" available online: http://eesiflo.com/water-cut-meter.html, accessed Aug. 27, 2015, pp. 1-3.

McKerricher G., et al. "Crude oil water-cut sensing with disposable laser ablated and inkjet printed RF microfluidics" Proceedings of the 2014 IEEE MTT-S International Microwave Symposium (IMS2014) Jun. 1, 2014, pp. 1-3.

Mohamed "Effect of salinity and temperature on water cut determination in oil reservoirs" Journal of Petroleum Science and Engineering 40 (2003), pp. 177-188.

Nyfors E., et al. "Measurement of mixtures of oil, water and gas with microwave sensors. New developments and field experience of the MFI MultiPhase, and WaterCut meters of Roxar" Proceedings of SPIE, vol. 4129, Jan. 1, 2000, pp. 12-21.

Nyfors, Ebbe Gustaf; "Cylindrical Microwave Resonator Sensors for Measuring Materials Under Flow" Report S243, Helsinki University of Technology, Espoo, Finland, May 26, 2000, pp. 1-181.

Roxar, "Roxar Watercut Meter" available on line: http://www2.emersonprocess.com/siteadmincenter/PM%20Roxar%20Documenls/Roxar%20Watercut%20meter%20Brochure.pdf, accessed Aug. 27, 2015, pp. 1-16.

Wylie, "RF sensor for multiphase flow measurement through an oil pipeline" Institute of Physics Publishing, Meas. Sci. Technol. 17 (2006), pp. 2141-2149.

Yang, "The Design, Development, and Field Testing of a Water-Cut Meter Based on a Microwave Technique" SPE 20697, Society of Petroleum Engineers Inc. 1990, pp. 775-782.

Co-pending U.S. Appl. No. 15/686,747, filed Aug. 25, 2017.

| $Z_0$ of shunt stub (Ω) | Width of shunt stub (mm) | $\varepsilon_{eff}$ | Fundamental Resonant Frequency "$f_0$" (MHz) | S21 value at $f_0$ (dB) |
|---|---|---|---|---|
| 100 | 1.5 | 1.63 | 229 | -36 |
| 75 | 2.6 | 1.67 | 226 | -37 |
| 50 | 5.1 | 1.73 | 222 | -42 |
| 40 | 7.0 | 1.76 | 220 | -45 |
| 25 | 13.0 | 1.82 | 218 | -47 |

WATER-CUT SENSOR SYSTEM

RELATED APPLICATIONS

This application claims the benefit of U.S. Provisional Application No. 62/393,804, filed on Sep. 13, 2016, titled "SYSTEMS AND METHODS FOR DETERMINING WATER-CUT OF A FLUID MIXTURE," and is a continuation-in-part of U.S. patent application Ser. No. 14/838,735, filed on Aug. 28, 2015, titled "SYSTEMS AND METHODS FOR DETERMINING WATER-CUT OF A FLUID MIXTURE," which are incorporated herein by reference in their entireties.

FIELD

Embodiments relate generally to characterization of fluid content and more particularly to systems and methods for measuring the water content (or "water-cut") of a fluid mixture.

BACKGROUND

Oil and gas wells typically produce oil and gas along with byproducts, such as water. These byproducts can be resident in a formation, or can be introduced into a formation, for example, to assist in producing oil or gas from the well. For example, oil wells are often stimulated using enhanced recovery methods, such as water injection, steam injection, natural gas reinjection and gas lift, to increase rates for recovering oil from the wells. The water (or other fluids) introduced into the formation can flow into a well and mix with the oil. As a result, the well may produce a fluid mixture of water and oil. Tracking or otherwise determining the water content in oil, also referred to as "water-cut," can be useful for many reasons. For example, water-cut measurements can be used during production to determine rates for introducing fluids in to a formation or well during the above described enhanced recovery methods, in feasibility analyses of oil wells, in monitoring refining processes (e.g., processes for desalting oil), for managing pipeline use, and so forth. Accordingly, many areas, including efficient oil production and refining processes, can benefit from economical systems and methods for obtaining precise measurements of water-cut.

SUMMARY

Applicants have recognized that, due to at least the wide range of uses for water-cut measurements, as well as the variety of environments and locations in which water-cut measurements are taken, it is desirable to provide economical and robust systems and methods for acquiring precise water-cut measurements. Moreover Applicants have recognized a need for precise on-line, real-time water-cut measurements for continuously monitoring water-cut of fluid flowing through a pipe, such as when an oil and water mixture is flowing through a pipe during oil production, refining processes and/or the like. Applicants have further recognized several shortcomings of existing systems and methods for acquiring precise water-cut measurements. For example, Applicants have recognized that traditional water-cut sensors for acquiring offline water-cut measurements, although sometimes precise, are generally incapable of providing on-line, real-time information are incapable of sensing water-cut across full water-cut range (e.g., 0% to 100% water concentrations in oil), may be limited to particular uses (e.g., the sensors are only capable for use with a limited range of pipe sizes and/or environments), may not be capable of accurately sensing water-cut for across different orientations of oil/water phases inside of a pipe, and/or may not be cost effective. Applicants have also recognized that many water-cut measuring techniques, such as those based on transmissometry, capacitance measurement, Coriolis effect, infrared (IR) spectroscopy, gamma ray spectroscopy and microwave, may each exhibit drawbacks that can make them inadequate for real-time monitoring of water-cut for fluids during oil production. For example, transmissometry based water-cut sensors can suffer from high signal losses, especially at high water-cut and/or high salinity, which can make them unsuitable for use in high water-cut and/or high salinity conditions. Similarly, capacitive type water-cut sensors may not provide sufficient accuracy for high water-cut (e.g., above about 70%), which can make them unsuitable for use in high water-cut conditions. Coriolis effect based water-cut sensors typically exploit the difference in densities of oil and water, which are not very different. As a result, these types of sensors can suffer from low resolution. IR spectroscopy based water-cut sensors often employ IR sources that are susceptible to harsh-environments. Due to the generally harsh environment of water-cut measurements during oil production, the IR sources may need to be housed in a specialized enclosure, such as a scratch free and hard protective material like sapphire, which can increase complexity and cost, and still may not provide sufficient protection from the harsh environment. Gamma ray spectroscopy based water-cut sensors can present health hazards which can make them difficult to maintain and handle, and limit their use.

With regard to microwave based water-cut sensors, certain microwave based water-cut sensors rely on measuring a phase difference between transmitted and received microwave signals, which can have a direct link with the effective permittivity of the oil and water mixture. Some microwave based water-cut sensors exhibit high losses and, as a result, may not operate reliably under high water-cut conditions, especially for larger pipe sizes. In some instances, microwave based water-cut sensors for measuring water-cut of fluid flowing through pipes can employ transmit (Tx) and receive (Rx) antennas disposed inside of the pipe, such that the antennas are at least partially immersed in the fluid mixture as it flows through the pipe. Unfortunately, the portions of the antennas immersed in the fluid flow can inhibit the fluid flow in the pipe, which can cause an undesirable pressure loss in the fluid flow.

In some instances, microwave based water-cut sensors employ non-planar microwave resonators. Such resonators can be based upon either quasi cavity resonator ("quasi" in the sense that such cavity resonators have open or partially open ends to have minimum flow hindrance), cylindrical fin resonator (CFR) or terminated transmission lines (twin wire or coaxial). Applicants have recognized that, these types of microwave based water-cut sensors can also suffer from shortcomings. For example, cavity resonators may require complex feeding mechanisms through Tx and Rx antennas, CFRs may be intrusive in nature, and transmission line (TL) based resonators may need to be implemented in a bypass fashion to main a flow stream.

Recognizing these and other shortcomings of existing systems, Applicants have developed novel systems and methods for measuring water-cut of a fluid mixture in a pipe. This can include, for example, the water concentration of an oil and water mixture flowing through a cylindrical pipe. Described herein are embodiments of microwave resonator based water-cut (WC) sensors, and associated systems and methods. In some embodiments, a WC sensor employs dual ground planes disposed at least partially on opposite sides of a pipe. For example, certain embodiments include a T-resonator located on one side of the pipe and a complementary ground plane located on the opposite side of the pipe.

In some embodiments, a "straight" T-resonator includes an elongated shaped stub of conductive material that extends in a generally straight direction (e.g., parallel to the longitudinal axis of the pipe) along a side of the pipe (e.g., on an external surface of the pipe), and the ground plane includes a complementary elongated strip of conductive material that extends along on an opposite side of the pipe in a generally straight direction (e.g., parallel to the longitudinal axis of the pipe in the same). The elongated stub may have one of a variety of shapes, such as a rectangle or a ring. In the case of a rectangular shaped stub, the stub may be coupled to a feed line to form a "T" shaped resonator.

In some embodiments, a "helical" T-resonator includes an elongated helical stub of conductive material that extends in a spiral pattern along a side of the pipe (e.g., spiraling around the longitudinal axis of the pipe) and the ground plane includes an elongated helical strip of conductive material that extends in a complementary spiral pattern along the opposite side of the pipe. In such an embodiment, the elongated helical stub of the conductor and the elongated helical strip of the ground plane form a complementary pair of helical shaped conductors that spiral opposite one another around a length of the pipe. In some embodiments, a dual WC sensor can employ two resonators, extending along the length of the pipe in opposite directions (e.g., to the right and left of a feed line and/or ground ring). For example, a dual-helical WC sensor may include a first helical T-resonator and a first complementary helical ground plane that spiral opposite one another around a first length of a pipe in a first direction (e.g., to the right of a feed line) and a second helical T-resonator and second complementary helical ground plane that spiral opposite one another around a second length of the pipe in a second direction (e.g., to the left of the feed line).

As further described herein, certain embodiments of a WC sensor can employ the principles of series resonance introduced by a λ/4 open shunt stub located in the middle of a microstrip line. In certain embodiments, a corresponding WC determination can be based on the measurement of a WC sensor's resonant frequency (e.g., the resonant frequency of a T-resonator of the WC sensor) which can vary with the relative percentage of oil and water in the pipe due to the difference in the dielectric properties of oil and water.

As described herein, such WC sensors can provide for non-intrusive, in-situ water-cut sensing over full range of operation (e.g., for sensing water-cut of fluids having 0%-100% volumetric fraction of water in oil), may be suitable for use with wide range of pipe sizes, such as the various large and small pipes used in oil industry, and may be orientation insensitive. (e.g., the WC sensor may provide accurate measurements of WC independent of the orientation of the oil/water phases inside of the pipe).

Provided in some embodiments is a method of manufacturing a water-cut sensor system. The method including forming on an external surface of a cylindrical pipe, a helical T-resonator, a helical ground conductor and a separator of a water-cut sensor. Forming the helical T-resonator including the following: disposing, on the external surface of the cylindrical pipe, a feed line including a conductive material extending in a circumferential direction about the external surface of the cylindrical pipe; and disposing, on the external surface of the cylindrical pipe, a helical open shunt stub including a conductive material extending from the feed line in a spiral pattern along the external surface of the cylindrical pipe (the helical open shunt stub being conductively coupled to the feed line). Forming the helical ground conductor including the following: disposing, on the external surface of the cylindrical pipe, a ground ring including a conductive material extending in a circumferential direction about the external surface of the cylindrical pipe (the feed line overlapping the ground ring); and disposing, on the external surface of the cylindrical pipe, a helical ground plane including a conductive material extending from the ground ring in a spiral pattern along the external surface of the cylindrical pipe (the helical ground plane being located opposite the helical open shunt stub, and the helical ground plane being conductively coupled to the ground ring). Forming the separator including disposing the separator between the feed line and the ground ring (the separator being adapted to electrically isolate the feed line from the ground ring to electrically isolate the helical T-resonator from the helical ground conductor).

In some embodiments, the helical open shunt stub has a length that is greater than a diameter of the cylindrical pipe. In certain embodiments, the helical open shunt stub has a length that is between three and five times the diameter of the cylindrical pipe. In some embodiments, the spiral pattern of the helical open shunt stub includes a complete turn about the circumference of the cylindrical pipe such that the helical open shunt stub includes a complete turn about the circumference of the cylindrical pipe. In certain embodiments, the spiral pattern of the helical ground plane includes a complete turn about the circumference of the cylindrical pipe such that the helical open ground plane includes a complete turn about the circumference of the cylindrical pipe. In some embodiments, the feed line has a length that is the same or greater than a width of the helical open shunt stub. In certain embodiments, the ground ring has a width that is the same or greater than a width of the feed line. In some embodiments, the separator has a width that is the same or greater than a width of the feed line, and a length that is the same or greater than a length of the feed line. In certain embodiments, the helical ground plane has a width corresponding to an average of a first width associated with a minimum resonant frequency for oil and a second width associated with a minimum resonant frequency for water.

In some embodiments, the helical T-resonator includes a dual helical T-resonator and the helical ground conductor includes a dual helical ground conductor. Forming the helical T-resonator further includes disposing on the external surface of the cylindrical pipe, a second helical open shunt stub including a conductive material extending from the feed line in a direction opposite the helical open shunt stub and in a spiral pattern along the external surface of the cylindrical pipe. Forming the helical T-resonator further includes disposing on the external surface of the cylindrical pipe, a second helical ground plane including a conductive material extending from the ground ring in a direction opposite the helical ground plane and in a spiral pattern along the external surface of the cylindrical pipe. The second helical open shunt stub being conductively coupled to the feed line, the second helical ground plane being conductively coupled to the ground ring, and the second helical ground plane being located opposite the second helical open shunt stub.

In certain embodiments, the helical T-resonator includes an input terminal located at a first end of the feed line (the input terminal adapted to receive source signals from an external circuit) and an output terminal located at a second end of the feed line (the output terminal adapted to provide for sensing, by an external circuit, of response signals corresponding to the source signals). In some embodiments, a resonant frequency of the water-cut sensor is determined based on the source signals and the response signals, and a water-cut of fluid in the cylindrical pipe is determined based on the resonant frequency of the water-cut sensor.

In certain embodiments, disposing the helical open shunt stub on the external surface of the cylindrical pipe includes the following: disposing a first mask on the external surface of the cylindrical pipe (the first mask including a first opening at a first portion of the external surface of the cylindrical pipe for forming the helical open shunt stub); and disposing a conductive material into the first opening to form the helical open shunt stub on the first portion of the external surface of the cylindrical pipe; disposing the helical ground plane on the external surface of the cylindrical pipe includes the following: disposing a second mask on the external surface of the cylindrical pipe (the second mask including a second opening at a second portion of the external surface of the cylindrical pipe for forming the helical ground plane); and disposing a conductive material into the second opening to form the helical ground plane on the second portion of the external surface of the cylindrical pipe; disposing the ground ring on the external surface of the cylindrical pipe includes the following: disposing a third mask on the external surface of the cylindrical pipe (the third mask including a third opening at a third portion of the external surface of the cylindrical pipe for forming the ground ring); and disposing a conductive material into the third opening to form the ground ring on the third portion of the external surface of the cylindrical pipe; and disposing the feed line on the external surface of the cylindrical pipe includes the following: disposing a fourth mask on the external surface of the cylindrical pipe, the fourth mask including a fourth opening at an external surface of the dielectric separator for forming the feed line of the helical T-resonator; and disposing the fourth conductive material into the fourth opening to form the feed line on the external surface of the dielectric separator.

Provided in some embodiments is a method for manufacturing a water-cut sensor system. The method including the following: disposing a first conductive material on a first portion of an external surface of a cylindrical pipe to form a helical open shunt stub of a helical T-resonator of a water-cut sensor (the helical open shunt stub extending in a spiral pattern along the external surface of the cylindrical pipe); disposing a second conductive material on a second portion of the external surface of the cylindrical pipe to form a helical ground plane of a helical ground conductor of the water-cut sensor (the helical ground plane extending in a spiral pattern along the external surface of the cylindrical pipe, and the helical ground plane being located opposite the helical open shunt stub such that fluid flow in the cylindrical pipe is adapted to flow between the helical ground plane and the helical open shunt stub); disposing a third conductive material on a third portion of the external surface of the cylindrical pipe to form a ground ring of the helical ground conductor of the water-cut sensor (the ground ring extending in a circumferential direction about the external surface of the cylindrical pipe, and the ground ring being conductively coupled to the helical ground plane); disposing a dielectric separator on at least a portion of the ground ring to be overlapped by a feed line of the helical T-resonator of the water-cut sensor; and disposing a fourth conductive material on an external surface of the dielectric separator to form a feed line of the helical T-resonator of the water-cut sensor (the feed line overlapping the portion of the ground ring, and the feed line being conductively coupled to the helical open shunt stub).

In some embodiments, the helical open shunt stub has a length that is greater than a diameter of the cylindrical pipe. In certain embodiments, the helical open shunt stub has a length that is between three and five times the diameter of the cylindrical pipe. In some embodiments, the spiral pattern of the helical open shunt stub includes a complete turn about the circumference of the cylindrical pipe such that the helical open shunt stub includes a complete turn about the circumference of the cylindrical pipe. In certain embodiments, the spiral pattern of the helical ground plane includes a complete turn about the circumference of the cylindrical pipe such that the helical open ground plane includes a complete turn about the circumference of the cylindrical pipe. In some embodiments, the feed line has a length that is the same or greater than a width of the helical open shunt stub. In certain embodiments, the ground ring has a width that is the same or greater than a width of the feed line. In some embodiments, the dielectric separator has a width that is the same or greater than a width of the feed line, and a length that is the same or greater than a length of the feed line. In certain embodiments, the helical ground plane has a width corresponding to an average of a first width associated with a minimum resonant frequency for oil and a second width associated with a minimum resonant frequency for water.

In some embodiments, the helical T-resonator includes a dual helical T-resonator, the helical ground conductor includes a dual helical ground conductor, and the method further includes the following: disposing a fifth conductive material on a fifth portion of the external surface of the cylindrical pipe to form a second helical open shunt stub extending from the feed line in a direction opposite the helical open shunt stub and in a spiral pattern along the external surface of the cylindrical pipe (the second helical open shunt stub being conductively coupled to the feed line); and disposing a sixth conductive material on a sixth portion of the external surface of the cylindrical pipe to form a second helical ground plane extending from the ground ring in a direction opposite the helical ground plane and in a spiral pattern along the external surface of the cylindrical pipe (the second helical ground plane being conductively coupled to the ground ring, and the second helical ground plane being located opposite the second helical open shunt stub).

In certain embodiments, the helical T-resonator includes an input terminal located at a first end of the feed line (the input terminal adapted to receive source signals from an external circuit) and an output terminal located at a second end of the feed line (the output terminal adapted to provide for sensing, by an external circuit, of response signals corresponding to the source signals). In some embodiments, a resonant frequency of the microwave resonator water-cut sensor is determined based on the source signals and the response signals, and a water-cut of fluid in the cylindrical pipe is determined based on the resonant frequency of the microwave resonator water-cut sensor.

In certain embodiments, disposing a first conductive material on a first portion of an external surface of a cylindrical pipe to form the helical open shunt stub includes the following: disposing a first mask on the external surface of the cylindrical pipe (the first mask including a first opening at the first portion of the external surface of the cylindrical pipe for forming the helical open shunt stub); and disposing the first conductive material into the first opening to form the helical open shunt stub on the first portion of the external surface of the cylindrical pipe. Disposing the second conductive material on a second portion of the external surface of the cylindrical pipe to form the helical ground plane includes the following: disposing a second mask on the external surface of the cylindrical pipe (the second mask including a second opening at the second portion of the external surface of the cylindrical pipe for forming the helical ground plane, and the second portion of the external surface of the cylindrical pipe being opposite the first portion of the external surface of the cylindrical pipe); and disposing the second conductive material into the second opening to form the helical ground plane on the second portion of the external surface of the cylindrical pipe. Disposing a third conductive material on a third portion of the external surface of the cylindrical pipe to form the ground ring includes the following: disposing a third mask on the external surface of the cylindrical pipe (the third mask including a third opening at the third portion of the external surface of the cylindrical pipe for forming the ground ring, and the third portion extending at least from the ground plane about a circumference of the cylindrical pipe); and disposing the third conductive material into the third opening to form the ground ring on the third portion of the external surface of the cylindrical pipe (the ground ring being conductively coupled to the helical ground plane). Disposing a fourth conductive material on an external surface of the dielectric separator to form a feed line includes the following: disposing a fourth mask on the external surface of the cylindrical pipe (the fourth mask including a fourth opening at an external surface of the dielectric separator for forming the feed line of the helical T-resonator); and disposing the fourth conductive material into the fourth opening to form the feed line on the external surface of the dielectric separator (the feed line being conductively coupled to the helical open shunt stub).

Provided in some embodiments is a method for manufacturing a water-cut sensor. The method including the following: disposing a first mask on an external surface of a cylindrical pipe (the first mask including a first opening at a first portion of the external surface of the cylindrical pipe for forming a helical open shunt stub of a helical T-resonator); disposing a first conductive material into the first opening to form the helical open shunt stub of the helical T-resonator on the first portion of the external surface of the cylindrical pipe; disposing a second mask on the external surface of the cylindrical pipe (the second mask including a second opening at a second portion of the external surface of the cylindrical pipe for forming a helical ground plane of a helical ground conductor, and the second portion of the external surface of the cylindrical pipe being opposite the first portion of the external surface of the cylindrical pipe); disposing a second conductive material into the second opening to form the helical ground plane of the helical ground conductor on the second portion of the external surface of the cylindrical pipe; disposing a third mask on an external surface of the cylindrical pipe (the third mask including a third opening at a third portion of the external surface of the cylindrical pipe for forming a ground ring of the helical ground conductor, and the third portion extending at least from the ground plane about a circumference of the cylindrical pipe); disposing a third conductive material into the third opening to form the ground ring of the helical ground conductor on the third portion of the external surface of the cylindrical pipe (the ground ring being conductively coupled to the helical ground plane); disposing a dielectric separator on at least a portion of the ground ring to be overlapped by a feed line of the helical T-resonator; disposing a fourth mask on an external surface of the cylindrical pipe (the fourth mask including a fourth opening at an external surface of the dielectric separator for forming the feed line of the helical T-resonator); and disposing a fourth conductive material into the fourth opening to form the feed line of the helical T-resonator on the external surface of the dielectric separator (the feed line being conductively coupled to the helical open shunt stub).

Figure 1:
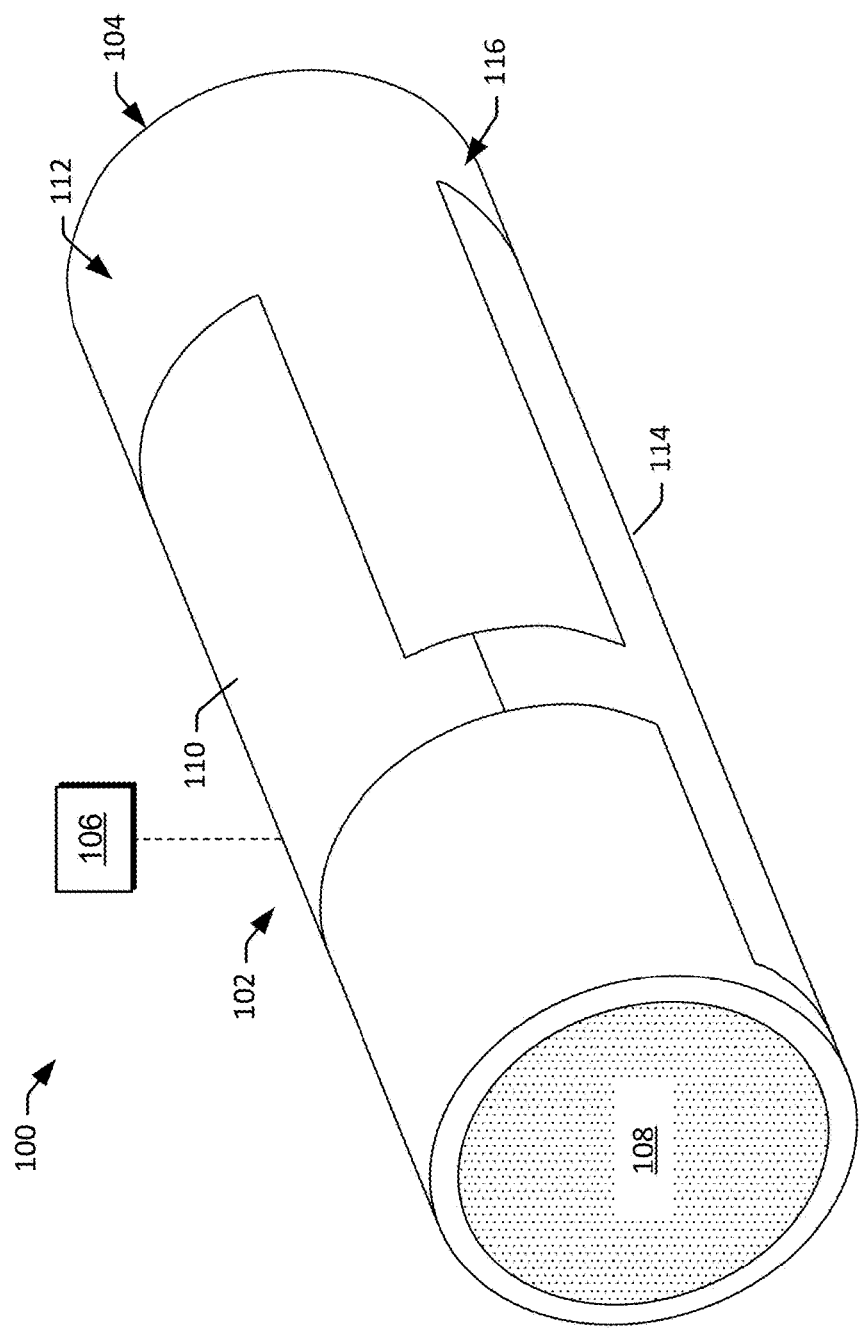
FIG. 1 is a diagram that illustrates an example water-cut (WC) sensing system in accordance with one or more embodiments.

While this disclosure is susceptible to various modifications and alternative forms, specific embodiments thereof are shown by way of example in the drawings and will be described in detail herein. The drawings may not be to scale. It should be understood, however, that the drawings and the detailed descriptions thereof are not intended to limit the disclosure to the particular form disclosed, but, to the contrary, the intention is to cover all modifications, equivalents, and alternatives falling within the spirit and scope of the present disclosure as defined by the appended claims.

DETAILED DESCRIPTION

Described are embodiments of systems and methods for measuring the water content of a fluid mixture. For example, certain embodiments provide for measuring water content in oil (e.g., volumetric fraction of water in oil), also referred to as "water-cut" (WC). In some embodiments, provided is a microwave resonator based water-cut (WC) sensor, and associated systems and methods. Embodiments of the WC sensor can provide non-intrusive, in-situ water-cut sensing over full range of operation (e.g., sensing water-cut of fluids having 0%-100% volumetric fraction of water in oil). As described herein, in some embodiments, a WC sensor employs series resonance introduced by a $\lambda/4$ open shunt stub located in the middle of a microstrip line. In some embodiments, a WC sensor can include a planar microwave resonator. For example, a WC sensor may include a signal conductor (SC) (e.g., a first conductive plane) disposed on a first portion of the surface of a cylindrical pipe, and a complementary ground conductor (GC) (e.g., a second conductive plane) disposed on a second portion of the surface of the cylindrical pipe that is opposite a complementary portion of the signal conductor on the first/upper/top surface of the pipe. In some embodiments, the signal conductor may include a T-resonator. For example, the signal conductor may include a layer of generally "T" shaped conductive material (e.g., copper) disposed on the surface of the pipe, and the ground conductor may include a complementary layer of conductive material (e.g., copper) disposed the surface of the pipe to form a ground ring that wraps around the circumference of the pipe and a ground plane (GP) that is complementary to at least a portion of the T-resonator. The T-resonator may include, for example, a feed line that wraps at least partially around the circumference of the pipe (e.g., to form the upper portion of the "T" shape) and one or more open shunt stubs (SS) that extends from a central portion the feed line, along a length of the pipe (e.g., to form the bottom portion of the "T" shape). The ground plane may include a portion of the complementary layer of conductive material disposed opposite the one or more shunt stubs.

In some embodiments, a "straight" T-resonator includes an elongated straight shunt stub that extends parallel to the longitudinal axis of the pipe and along a side of the pipe (e.g., on an external surface of the pipe), and the ground conductor includes a complementary elongated straight ground plane that extends parallel to the longitudinal axis of the pipe and along a side of the pipe opposite the elongated shunt stub. The elongated shunt stub may have one of a variety of shapes, such as a rectangle or a ring.

In some embodiments, a "helical" T-resonator includes an elongated helical open shunt stub that extends in a spiral pattern along a side of the pipe and around the longitudinal axis of the pipe, and the ground plane includes a complementary elongated helical ground plane that extends in a spiral pattern along a side of the pipe opposite the shunt stub and around the longitudinal axis of the pipe. In such an embodiment, the elongated helical open shunt stub and the complementary elongated helical ground plane may form a complementary pair of helical shaped conductors that spiral opposite one another around a length of the pipe.

In some embodiments, a "dual" water-cut sensor employs two resonators, extending along the length of the pipe in opposite directions (e.g., to the right and left of a feed line and/or ground ring). The two resonators can be mutually rotated by 90° with respect to each other around the pipe axis. For example, a "dual-helical" water-cut sensor may include a first pair of helical shaped conductors that spiral opposite one another around a length of a pipe in a first direction (e.g., to the right of a feed line) and a second pair of helical shaped conductors that spiral opposite one another around a length of a pipe in a second direction (e.g., to the left of the feed line).

As further described herein, in certain embodiments, a water-cut sensors can employ the principles of series resonance introduced by a λ/4 open shunt stub located in the middle of a microstrip line (e.g., a feed line). A corresponding water-cut determination can be based on the measurement of a water-cut sensor's resonant frequency (e.g., the resonant frequency of a T-resonator of the water-cut sensor), which can vary with the relative percentage of oil and water due to the difference in the dielectric properties of oil and water.

As described herein, embodiments of WC sensors can provide for non-intrusive, in-situ water-cut sensing over full range of operation (e.g., for sensing water-cut of fluids having 0%-100% volumetric fraction of water in oil), may be suitable for use with wide range of pipe sizes, such as the various large and small pipes used in oil industry, and may be orientation insensitive (e.g., the WC sensor may provide accurate measurements of WC independent of the orientation of the oil/water mixture inside of the pipe). Further details of embodiments of such water-cut sensor systems, and relevant concepts behind the embodiments, are discussed in more detail herein.

FIG. 1 is a block diagram that illustrates an example water-cut (WC) sensing system 100 in accordance with one or more embodiments. In some embodiments, the WC sensing system 100 includes a water-cut (WC) sensor 102, a cylindrical pipe 104, and/or a measurement processing system 106. As discussed herein, the WC sensor 102 may be disposed on (or otherwise integrated within) the cylindrical pipe 104. In some embodiments, the WC sensor 102 includes a signal conductor (SC) 110 (e.g., a first conductive plane), such as a T-resonator, disposed at a first/upper/top surface 112 of the cylindrical pipe 104, and a ground conductor (GC) 114 (e.g., a second conductive plane) disposed at a second/lower/bottom surface 116 of the cylindrical pipe 104 that is opposite the first/upper/top surface 112 of the pipe 104. That is, the center of the ground conductor 114 may have an angular offset from the center of the signal conductor 110 of about 180 degrees around the longitudinal axis of the pipe 104. In some embodiments, the ground conductor 114 may include a ring portion that extends about the circumference of the pipe 104. Thus, the ground conductor 114 may have a conductive path that wraps completely around the pipe 104. Certain embodiments of a WC sensor system employing a T-resonator are discussed in more detail herein with regard to at least FIGS. 10A-10E.

In such a configuration, the WC sensing system 100 can be employed to sense a water-cut of a fluid 108 (e.g., a water and oil mixture, or other substrate) flowing through, or otherwise present in, the pipe 104. For example, the measurement processing system 106 may introduce one or more source signals into the WC sensor 102 and/or sense one or more corresponding response signals from the WC sensor 102, and may analyze the characteristics of the one or more source signals and/or the one or more corresponding response signals to determine a resonant frequency of the WC sensor 102 in the presence of the fluid 108 (e.g., a resonant frequency of the T-resonator of the signal conductor 110) with the fluid 108 currently flowing through or otherwise located in the pipe 104 (e.g., the fluid 108 located between the signal conductor 110 and the ground conductor 114), and based on a predetermined correlation (e.g., a mapping) between the water-cut of a fluid mixture flowing through the pipe 104 and the resonant frequency of the WC sensor 102, determine the water-cut of the fluid 108. That is, the water-cut of the fluid 108 passing through the pipe 108 can be determined based on the resonant frequency of the WC sensor 102 at or near the time when the fluid 108 passes through the portion of the pipe 104 on which the WC sensor 102 is disposed. As described herein, such a WC sensor 102 may be non-intrusive, may be scaled to a wide variety of pipe sizes, may be implemented using relatively simple and inexpensive manufacturing techniques, may be orientation insensitive, and/or may be able to achieve at least about 0.1% repeatability.

Although certain embodiments are described herein with regard to a T-resonator type signal conductor 110 for the purpose of illustration, embodiments can include any suitable type/shaped signal conductor 110. For example, embodiments can be employed using a ring type signal conductor 110, or other suitable type/shape signal conductor 110, in place of or in conjunction with a T-resonator type signal conductor 110. Embodiments of a WC sensor system employing a ring type signal conductor 110 (e.g., a "ring-resonator") are discussed in more detail herein with regard to at least FIG. 4. Further details of embodiments of such a WC sensor system 100, and relevant concepts behind the embodiments, including certain characteristics of the various elements of embodiments of the WC sensor system 100, such as the shapes, dimensions, placement and/or the like of signal and/or ground conductors, are discussed in more detail herein.

In some embodiments, a microwave resonator of a WC sensor described herein may be characterized in a manner similar to a transmission line (TL), with a fluid present between the signal and ground conductors of the WC sensor being characterized as a substrate of the transmission line. The characteristic impedance of a transmission line may be the ratio of the voltage and current of a wave travelling along the line. When the wave reaches the end of the line, in general, there can be a reflected wave which travels back along the line in the opposite direction. When this wave reaches the source, it may add to the transmitted wave and the ratio of the voltage and current at the input to the line may no longer be the characteristic impedance. This new ratio is called the input impedance. The input impedance of an infinite line may equal the characteristic impedance since the transmitted wave is never reflected back from the end. It can be shown that an equivalent definition is: the characteristic impedance of a line is that impedance which when terminating an arbitrary length of line at its output will produce an input impedance equal to the characteristic impedance. This is so because there is no reflection on a line terminated in its own characteristic impedance.

A substrate (e.g., with dielectric constant of ($\varepsilon_r$) and loss tangent (tan δ)) may define the capacitance (C) and conductance (G) of a transmission line which affects its characteristic impedance ($Z_0$), as evident from the following equations for characteristic impedance ($Z_0$) (equation 1), and speed of microwaves passing through it (equation 2). Characteristic impedance ($Z_0$) for a transmission (TL) may be expressed as follows:

$$Z_O = \sqrt{\frac{R + j\omega L}{G + j\omega C}} \quad (1)$$

where R is the resistance per unit length, considering the two conductors to be in series, L is the inductance per unit length, G is the conductance of the dielectric per unit length, C is the capacitance per unit length, j is the imaginary unit, and ω is the angular frequency. Microwaves may be passed through a dielectric medium by alternate cycles of charging and discharging, such that high storage capacity (e.g., high capacitance or $\varepsilon_r$) of the substrate can cause hindrance in changing polarity, thereby causing a reduction in the speed of microwaves, as evidenced by (equation 2). The velocity (υ) of a microwave in a dielectric medium can be expressed as follows:

$$\upsilon = \frac{c}{\sqrt{\varepsilon_{\mathit{eff}1}}} \qquad (2)$$

where c is the speed of light (e.g., about 2.998×10⁸ meters per second (m/s)), and $\varepsilon_{\mathit{eff}1}$ is the effective permittivity of the dielectric medium through which the microwave is traveling and depends upon the fringing field pattern defined by the placement of signal and ground conductors. A difference in speed of microwaves can cause a transmission line of the same physical length to appear electrically different for substrates of different dielectric constants ($\varepsilon_r$) (e.g., which may vary from about 2.6 to about 80 for different watercuts). The microwave resonance phenomenon may be based upon the superposition of two oppositely travelling waves which causes the standing wave pattern to appear at different frequencies, depending upon the speed of microwaves, as provided by equation 2. As such, resonant frequency of a microwave resonator may be correlated with the substrate's dielectric constants ($\varepsilon_r$).

In some embodiments, planar microwave resonators can be constructed using different transmission line modes. For example, resonators can be constructed using a microstrip line mode configuration or a co-planar waveguide (CPW) mode configuration. A microstrip line mode configuration may employ sandwiching of a dielectric medium between a signal conductor and ground conductor. A CPW mode configuration may employ conductors disposed side-by-side on the surface of a dielectric medium. Of these two modes, microstrip line may more sensitive to the change in dielectric properties of the substrate. This sensitivity of microstrip line may be attributable to its sandwiching of a dielectric medium between signal and ground conductors, which can enable electric fields (E fields) and magnetic field (H fields) to penetrate into and through the medium located there between. In contrast, the side by side conductor placement a CPW mode may allow a relatively large proportion of fields to be directed into air adjacent the medium, with less fields penetrating into and through the medium.

Figure 2A:
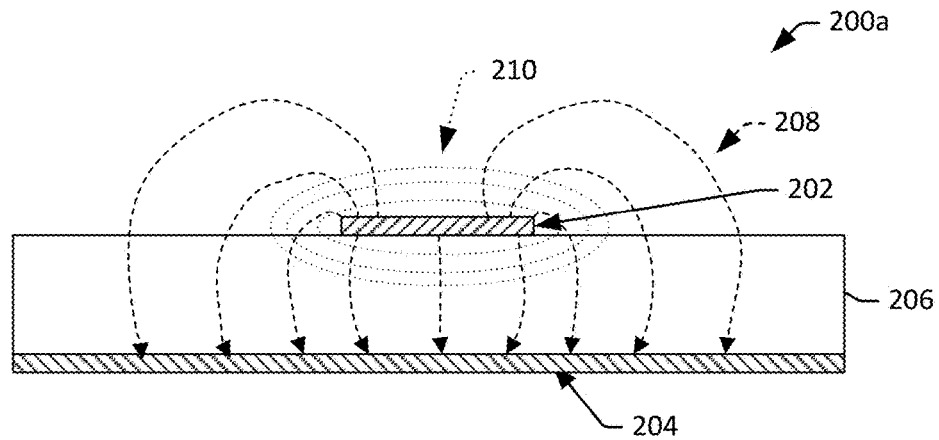
FIGS. 2A and 2B are diagrams that illustrate example microwave transmission lines employing a microstrip line mode and a co-planer waveguide mode, respectively, in accordance with one or more embodiments.
Figure 2B:
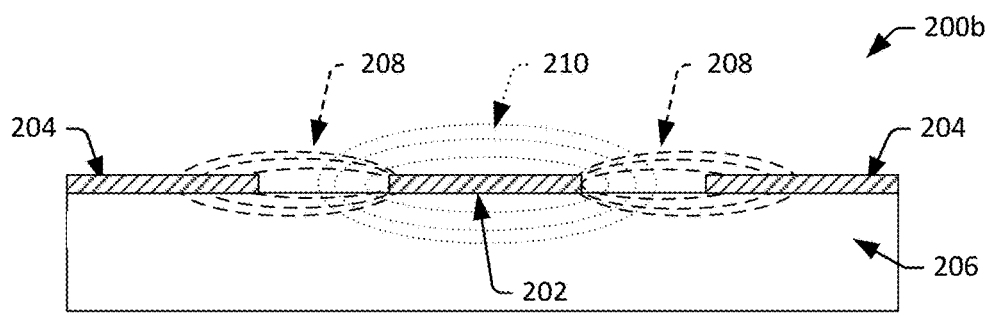

FIGS. 2A and 2B are diagrams that illustrate example microwave transmission lines 200a and 200b employing a microstrip line mode and a CPW mode, respectively, in accordance with one or more embodiments. FIGS. 2A and 2B both illustrate a signal conductor 202, ground conductor (s) 204, and a substrate (or medium) 206, as well as example E field lines (arrows 208) and H field lines (arrows 210) extending there between. As depicted in FIG. 2A, a relatively large amount of the E field lines penetrate the substrate 206 (e.g., as indicated by the arrows 208 extending from the signal conductor 202 to the ground conductor 204), with some of the H field lines passing through a portion of the substrate 206 (e.g., as indicated by only the lower portion of the H-field arrows 210 extending through the substrate 206 from the signal conductor 202 to the ground conductor 204). As depicted in FIG. 2B, a relatively small amount of the E field lines penetrate the substrate 206 (e.g., as indicated by only the lower portion of the arrows 208 extending through the substrate 206 from the signal conductor 202 to the ground conductors 204 on either side). As indicated in FIGS. 2A and 2B, in both microstrip line mode and CPW mode, a similar portion of the H field may penetrate the substrate 206 (e.g., as indicated by the lower half of the arrows 210 extending through the upper portion of the substrate 206 that is adjacent to the conductors 202).

Figure 3:
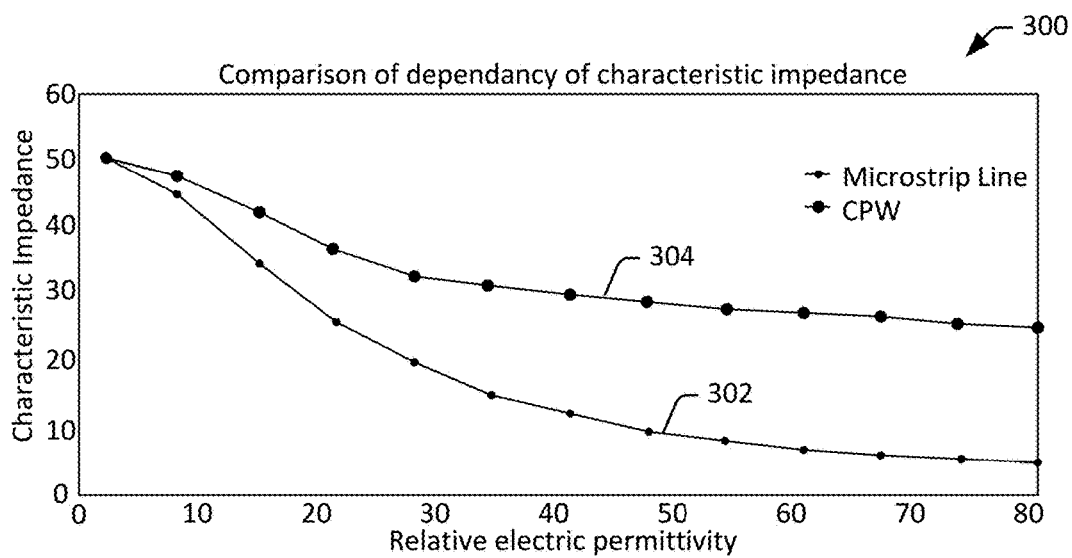
FIG. 3 is a plot diagram that illustrates values of characteristic impedance of a standard microstrip line and co-planer waveguide modes in accordance with one or more embodiments.

To verify the above described effect quantitatively, a model (e.g., an high frequency structural simulator (HFSS) model) can be generated for the microstrip line mode and/or the CPW mode. FIG. 3 is a plot diagram 300 that illustrates values of characteristic impedance (Ω or $Z_0$) of a standard microstrip line and CPW modes as a function of substrate permittivity at 200 MHz (megahertz) in accordance with one or more embodiments. The lower line 302 in the diagram represents the characteristic impedance (Ω or $Z_0$) as a function of relative electric permeability for a microstrip line mode, and the upper line 304 in the diagram represents the characteristic impedance (Ω or $Z_0$) as a function of relative electric permeability for a CPW mode. The illustrated embodiment may correspond to a substrate having a thickness of about 1.6 mm (millimeters). The diagram 300 illustrates the real part of characteristic impedance ($Z_0$) of both TL modes matched to 50 ohms at a relative electric permeability ($\varepsilon_r$) of about 2 for the medium, which is typical for oils. As can be seen, the CPW mode may be less affected by the shape/thickness of the substrate than the microstrip mode. This may be attributable to a relatively low amount of the field lines for the CPW penetrating the substrate. Thus, CPW may be suitable for wrapping the conductors around a non-planar structure, such as a three-dimensional (3D) cylindrical pipe surface. In some embodiments, the dependency of microstrip mode the geometric structure of substrate may be resolved using a dual ground plane microstrip TL, such as that described herein (e.g., a WC sensor for a pipe that includes a signal conductor (e.g., a T-resonator) disposed on one side of the substrate, and a ground conductor disposed on an opposite side of the substrate).

Figure 4:
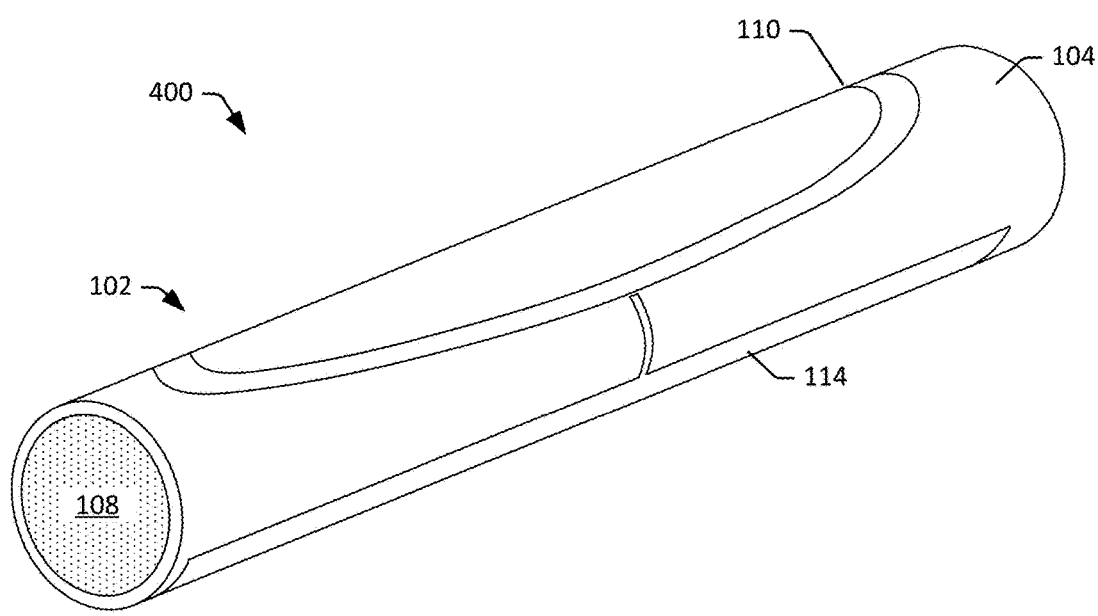
FIG. 4 is a diagram that illustrates an example ring resonator microstrip line based microwave resonator system in accordance with one or more embodiments.
Figure 5:
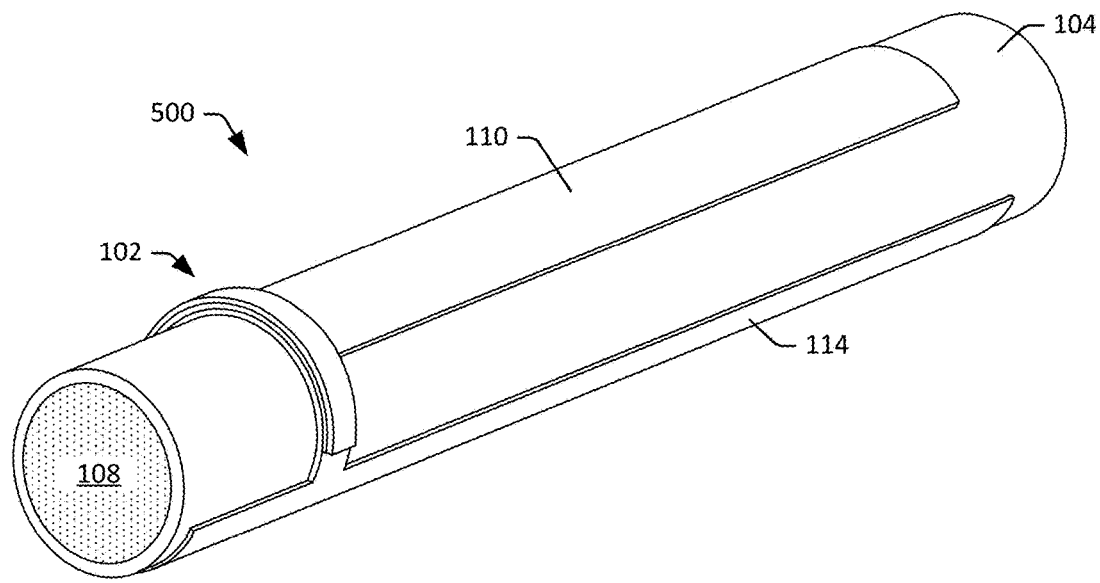
FIG. 5 is a diagram that illustrates an example T-resonator microstrip line based microwave resonator system in accordance with one or more embodiments.

In some embodiments, different types of microstrip line based microwave resonators can be implemented, such as a ring resonator (e.g., a circular resonator or an elliptical resonator) or an open/short circuited stub resonator (e.g., a T-resonator). FIG. 4 is a diagram that illustrates an example ring resonator microstrip line based microwave resonator system (or "ring system") 400 in accordance with one or more embodiments. FIG. 5 is a diagram that illustrates an example T-resonator microstrip line based microwave resonator system (or "T-resonator system") 500 in accordance with one or more embodiments. Referring to at least FIG. 4 the ring system 400 may include a WC sensor 102 having a ring shaped (e.g., circular or elliptical) signal conductor 110 disposed on one side (e.g., a first/upper/top side) of a pipe 104, and a ground conductor 114 (e.g., generally rectangular in shape) disposed on an opposite side (e.g., a second/lower/bottom side) of the pipe 104. Referring to at least FIG. 5 the T-resonator system 500 may include a WC sensor 102 having a T-shaped signal conductor 110 (e.g., having a feed line and an open shunt stub) disposed on one side (e.g., a first/upper/top side) of a pipe 104, and a ground conductor 102 (e.g., generally rectangular in shape) disposed on an opposite side (e.g., a second/lower/bottom side) of the pipe 104. Although certain embodiments are described herein with regard to a T-resonator type signal conductor 110 for the purpose of illustration, embodiments may include any suitable type/shaped signal conductor 110. For example, embodiments can be employed using a ring type signal conductor 110, or other suitable type/shape signal conductor 110, in place of or in conjunction with a T-resonator type signal conductor 110. As described herein, the T-resonator may include a "straight" T-resonator (e.g., similar to that described with regard to at least FIGS. 5 and 10A-11B) or a "helical" T-resonator (e.g., similar to that described with regard to at least FIGS. 12A-15B).

Figure 6:
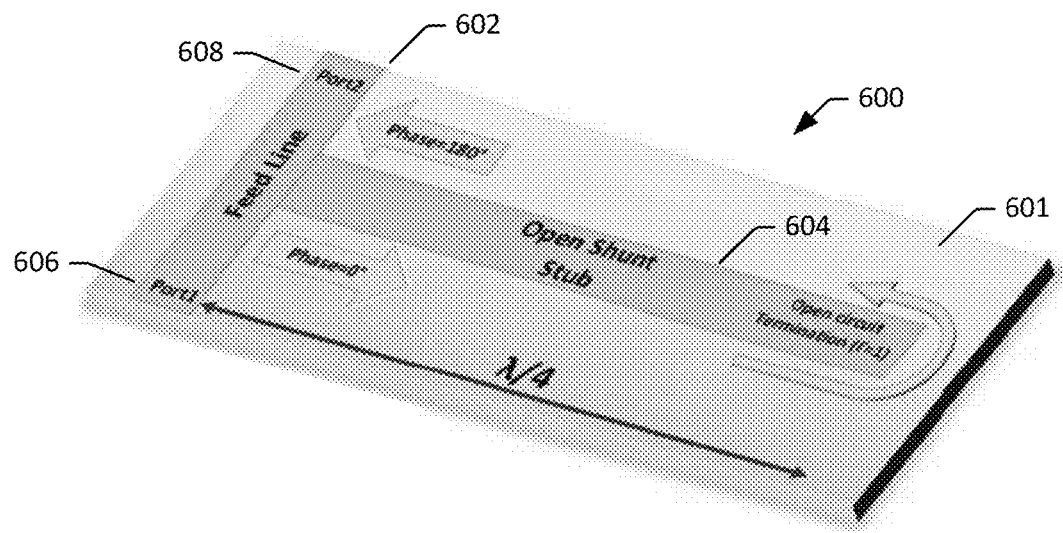
FIG. 6 is a diagram that illustrates example components of a T-resonator on a flat substrate in accordance with one or more embodiments.

A T-resonator may include a transmission line (used for feeding and receiving microwave energy) shunted with either a λ/4 length of open circuited or λ/2 length of short circuited stub. A λ/4 open circuited stub may be relatively short in size (for a given operational frequency) and, in some instances may be implemented without requiring any via. FIG. 6 is a diagram that illustrates example components of a T-resonator 600 laid flat on a substrate 601 in accordance with one or more embodiments. As depicted, the T-resonator 600 may include a conductive material of a "T" shape, having a feed line (FL) 602 and an open shunt stub (SS) 604. The feed line may include a first port 606 and a second port 608. The first port 606 may be used to introduce a signal (e.g., at a given frequency and phase) into the T-resonator 600. The second port may be used to sense a corresponding response signal (e.g., having a frequency and/or phase that may be different than the introduced signal). When deployed on a cylindrical pipe, the T-resonator 600 may take on a generally curved profile to that conforms to a surface of a pipe, as discussed in more detail herein with regard to at least FIGS. 10A-10E.

At resonant frequencies, an open shunt stub may appear as a short circuit after λ/4 transformation (π radian rotation on the smith chart) in the middle of the transmission line. That is, incident and reflected waves may differ by about 180° (opposite in phase) at resonant frequencies, in the middle of transmission line, causing choke of signal transmission (e.g., due to destructive interference) between the ports. So, an S21 response (e.g., a response signal at the second port 608 due to a source signal introduced at the first port 606, representing the power transferred from the first port 606 to the second port 608) of the T-resonator may be characterized by dips at the resonant frequencies. A resonant frequency of a T-resonator can indicate the dielectric constant ($\varepsilon_r$) of the substrate, and a guided wavelength ($\lambda_g$) can indicate the resonant frequency of a T-resonator. Based on these relationships, the guided wavelength ($\lambda_g$) and/or the resonant frequency of a T-resonator may be utilized to find an unknown dielectric constant ($\varepsilon_r$) and loss of a medium (e.g., the dielectric constant ($\varepsilon_r$) and loss of an oil/water mixture flowing through a pipe 300 on which a microwave resonator, including a T-resonator similar to T-resonator 600, is disposed).

As discussed herein, embodiments of a WC sensor employing a microwave resonator system may include wrapping a signal conductor of a T-resonator on circumference of upper semi-cylindrical pipe surface and ground conductor on lower semi-cylindrical surface. In such an embodiment, several factors may be considered, including the following:

a) guided wavelength ($\lambda_g$) of the open shunt stub (SS) ($\lambda_{g\text{-}ss}$);
b) characteristic impedance ($Z_0$) of the open shunt stub (SS) ($Z_{0\text{-}SS}$); and
c) characteristic impedance ($Z_0$) of the feed line (FL) ($Z_{0\text{-}FL}$).

With regard to the guided wavelength ($\lambda_g$) of an open shunt stub, the wavelength of microwaves in a medium can be defined as follows:

$$\lambda_g = \frac{\lambda_O}{\sqrt{\varepsilon_{\mathit{eff}}}} \quad (3)$$

where $\lambda_O$ is a free space wavelength, and $\varepsilon_{\mathit{eff}}$ is the effective permittivity of the dielectric medium through which the microwave is traveling and depends upon the fringing field pattern defined by the placement of signal and ground conductors. The effective permeability ($\varepsilon_{\mathit{eff}}$) may depend upon the following parameters:

a) a distance between signal and ground conductor; and
b) a dielectric constant ($\varepsilon_r$) of the substrate.

For the open shunt stub, the distance between ground and signal conductor may remain fixed so the guided wavelength ($\lambda_g$) may depend only on a dielectric constant ($\varepsilon_r$) of the substrate (e.g., the mixture inside the pipe). An increase in water-cut (e.g., an increase in the proportion of water to oil in the mixture) may cause the effective permeability ($\varepsilon_{\mathit{eff}}$) to increase and/or the guided wavelength ($\lambda_g$) to decrease. Consequently same physical length of shunt stub of T-resonator may appear electrically larger at a high water-cut, with a decreased resonant frequency.

Figure 7:
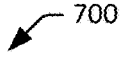
FIG. 7 is a table that illustrates example simulation results of parametric study of the effect of the characteristic impedance of the open shunt stub ($Z_{0\text{-}SS}$) of a T-resonator on performance of the T-resonator in accordance with one or more embodiments.

With regard to the characteristic impedance ($Z_0$) of the open shunt stub (SS) ($Z_{0\text{-}SS}$), similar to $\lambda g$, the characteristic impedance of the open shunt stub ($Z_{0\text{-}SS}$) can also depend upon the effective permeability ($\varepsilon_{\mathit{eff}}$). The characteristic impedance of the open shunt stub ($Z_{0\text{-}SS}$), however, may not have any pronounced effect on the performance of the T-resonator. This can be verified by a parametric study investigating the effect of the characteristic impedance of the open shunt stub ($Z_{0\text{-}SS}$) on performance of a simple flat substrate based T-resonator. FIG. 7 is a table 700 that illustrates example simulation results of parametric study of the effect of the characteristic impedance of the open shunt stub ($Z_{0\text{-}SS}$) of a T-resonator on performance of the T-resonator in accordance with one or more embodiments. The table 700 may illustrate that good signal rejection (dip) in S21 response (at $f_0$) can be achieved (e.g., $f_0$ can be identified) irrespective of the characteristic impedance of the open shunt stub ($Z_{0\text{-}SS}$). Moreover, the effective permeability ($\varepsilon_{\mathit{eff}}$) increases, approaching dielectric constant ($\varepsilon_r$), for decreasing values of the characteristic impedance of the open shunt stub ($Z_{0\text{-}SS}$). This may be attributable to field lines becoming denser in the substrate, resulting in $f_0$ shifting towards lower frequencies.

In some embodiments of a T-resonator implemented on a pipe surface, the physical width of shunt stub may be constant along its length. As demonstrated by the values in the table 700 of FIG. 7, in such an embodiment, with an increase in water-cut (e.g., an increase in the proportion of water to oil in the mixture) which appears as an increase in the effective permeability ($\varepsilon_{\mathit{eff}}$), the characteristic impedance of the open shunt stub ($Z_{0\text{-}SS}$) may decrease, the width of the shunt stub may appear to increase, and the resonant frequency ($f_0$) may decrease. That is, increasing WC (e.g., increasing the effective permeability ($\varepsilon_{\mathit{eff}}$)) can cause a decrease in the guided wavelength ($\lambda_g$) and the characteristic impedance of the open shunt stub ($Z_{0\text{-}SS}$), and, as a result, a decrease in the resonant frequency ($f_0$) of the resonator.

With regard to the characteristic impedance ($Z_0$) of the feed line (FL) ($Z_{0\text{-}FL}$), since feed line can be utilized to provide and/or receive the microwave signal from the open shunt stub, it may be matched to about 50Ω (the characteristic impedance ($Z_0$) of most of measurement equipment) to avoid mismatch losses which can negatively affect the WC sensor's performance.

In some embodiments, the characteristic impedance of the feed line ($Z_{0\text{-}FL}$) may vary based on at least the following:
a) the variable distance between the signal conductor and the ground conductor; and
b) the variable dielectric constant ($\varepsilon_r$) of the mixture inside the pipe.

As discussed herein, in some embodiments, a separate ring shaped ground (or "ground ring") for the feed line can be included. Such a ground ring may eliminate, or otherwise reduce, the effect that the variable distance between the signal conductor and the ground conductor and/or the variable dielectric constant ($\varepsilon_r$) of the mixture inside the pipe has on the characteristic impedance of the feed line ($Z_{0\text{-}FL}$). In some embodiments, this supplemental ground plane (or ground ring), may be disposed between the curved feed line and the surface of a cylindrical pipe, and may connect with a main ground plane (or "bottom" ground plane) (GP) of the ground conductor. In some embodiments, the feed line and the ground ring may be separated by a dielectric separator. Example embodiments of ground rings and dielectric separators are discussed in more detail herein with regard to at least FIGS. 10A-10E, 12A-12E and 14A-14E.

As discussed herein, a T-resonator based WC sensor can be employed on a variety of different sized pipes. This can be advantageous in the oil and gas industry, for example, as WC measurements may be taken for fluid flowing through a variety of different sized pipes (e.g., pipes up about 1500 mm in diameter, or more). In an example embodiment, a pipe may have an internal diameter of about 46 mm and an outer diameter of about 50 mm. Although the length of the pipe may vary by application, a T-resonator based WC sensor may be disposed, for example, on a given length of the pipe (e.g., across about 350 mm of the pipe's length).

For shorter lengths, a majority of the fields from the open shunt stub may terminate at the ground ring which may severely affect the resonance sensing phenomenon. The length of the open shut stub may also determine the operational range of the WC sensor. In some embodiments, the open shunt stub may have a length that is the same or greater than the diameter of the pipe (which is about the separation between the open shunt stub and the main ground plane of the ground conductor). For example, in the above described embodiment, the open shunt stub may have a length that is equal to or greater than about 50 mm. In some embodiments, the length may be up to several times the diameter of the pipe. For example, the open shunt stub may have a length that is about three to five times longer than the diameter of the pipe (e.g., about 3× to 5× the separation between open shunt stub and the main ground plane of the ground conductor). For example, in the above described embodiment, the open shunt stub may have a length that is equal to or greater than about 250 mm (or about 5× the OD of the pipe). A length of about 250 mm may, for example, provide an operating range of about 80 MHz-190 MHz.

As discussed here, the width (or arc length) of the open shunt stub may determine its characteristic impedance ($Z_{0\text{-}SS}$), but the actual characteristic impedance ($Z_{0\text{-}SS}$) may vary as the dielectric constant ($\varepsilon_r$) of the substrate varies (e.g., in the presence of different oil and water mixtures). Continuing with the above example, including an open shunt stub having a length of about 250 mm, the shut stub may have a width of about 25.4 mm to provide a characteristic impedance of the open shunt stub ($Z_{0\text{-}SS}$) of about 50Ω. If an average distance between the signal conductor and ground plane is considered to be about to be 45 mm, along with an effective permeability ($\varepsilon_{eff}$) variation of about 2-80, then the width of about 25.4 mm may correspond to characteristic impedance of the open shunt stub ($Z_{0\text{-}SS}$) between about 108Ω-20Ω (e.g., similar to the same range provided in table 700 of FIG. 7).

In some embodiments, the length of the feed line can be about the same or greater than the width of the open shunt stub. Continuing with the above example, including an open shunt stub having a width of about 25.4 mm, the length of the feed line may be about 45 mm. In some embodiments, the width of the feed line can be dimensioned to achieve a desired characteristic impedance. Continuing with the above example, the width of the feed line may be about 2.5 mm to provide a characteristic impedance of the feed line ($Z_{0\text{-}FL}$) of about 50Ω.

In some embodiments, the width of the ground ring can be dimensioned to be the same or greater than the width of the feed line. For example, the width of the feed line may be about 2.5 times the width of the feed line. Continuing with the above example, including a feed line width of about 2.5 mm, the width of the ground ring may be about 6.3 mm.

In some embodiments, the separator can be dimensioned to provide physical and/or electrical isolation between the feed line and the ground ring. The width of the ground ring can be dimensioned to be about the same or greater than the width of the feed line and/or the ground ring. Continuing with the above example, including a ground ring having a width of about 6.3 mm, the width of the separator may be about 6.3 mm. In some embodiments, the length of the separator may be about the same or greater than the length of the feed line. Continuing with the above example, including a feed line length of about 45 mm, the length of the separator may be about 45 mm. In some embodiments, the separator may be of a sufficient thickness to provide physical and/or electrical isolation between the feed line and the ground ring. Continuing with the above example, the separator may have a dielectric constant ($\varepsilon_r$) of about 2.8 and a constant thickness of about 1 mm. Such a constant thickness separator may provide a constant separation distance between the feed line and the ground ring.

In some embodiments, the ground plane can be dimensioned to provide a field pattern that encompasses a relatively large amount of a cross-sectional area inside the pipe. Such a pattern may enable the field to pass through a relatively large portion of the medium flowing through the pipe (e.g., across the entirety of the cross-sectional area of the pipe) to provide an accurate representation of the medium flowing through the pipe as a whole, as opposed to the field passing through only portions of the flow (e.g., in the upper portion of cross-sectional area of the pipe) which may only provide a representation of the medium flowing through those limited portions of the pipe.

Figure 8A:
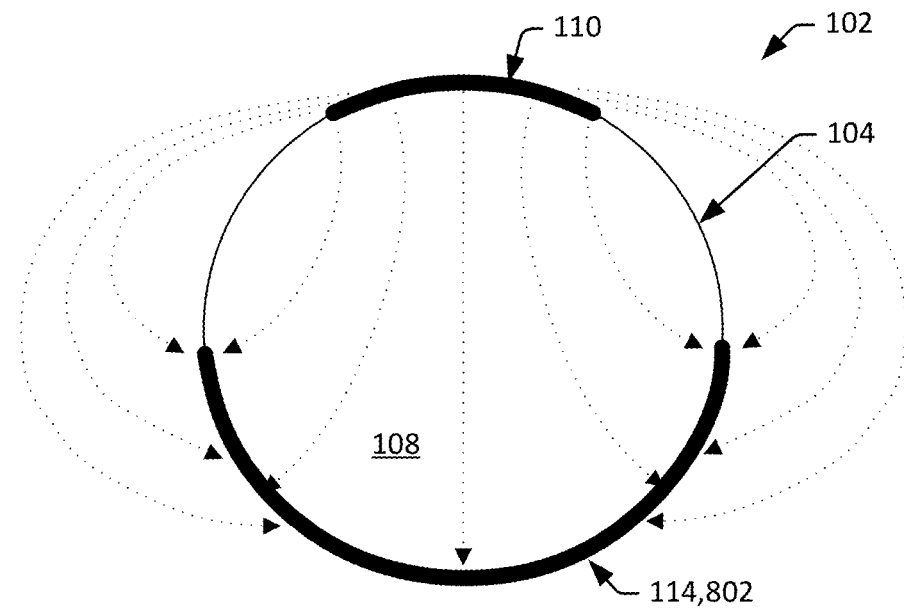
FIG. 8A is a diagram that illustrates field lines extending from a signal conductor to a relatively wide ground plane of a ground conductor on a pipe in accordance with one or more embodiments.

Referring to FIG. 8A, which is a diagram that illustrates field lines extending from a signal conductor 110 to a relatively wide "bottom" or "main" ground plane (GP) 802 of a ground conductor (GC) 114 on a cylindrical pipe 104 in accordance with one or more embodiments, a ground plane 802 with a relatively large width (e.g., having an arc length spanning a greater portion of the curvature of the second/lower/bottom side of the pipe 104), may cause a larger number of the field lines to terminate at or near the edges of the ground plane 802, with a smaller number of the field lines terminating on the central/bottom portion of the bottom ground plane 802. As a result, the field lines may pass through the upper/outside edges of the interior of the pipe 104, but may not cross through the lower/center portion of the interior of the pipe 104. Such an embodiment (e.g., incorporating a relatively wide ground plane 802) may be sensitive to relative percentage change of oil and water which occurs in the edge/side portions of the interior of the pipe 104, but may not be very sensitive to relative percentage change of oil and water which occurs in the lower/central portion of the interior of the pipe 104.

Figure 8B:
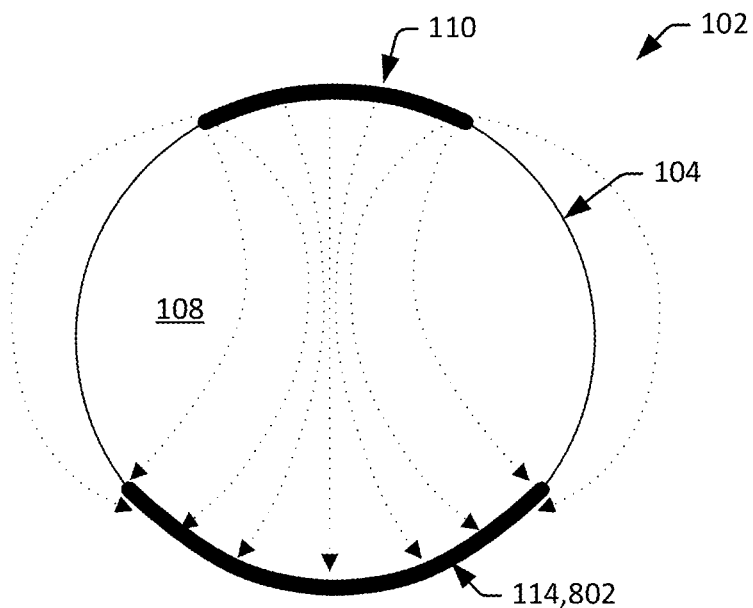
FIG. 8B is a diagram that illustrates field lines extending from a signal conductor to a relatively narrow ground plane of a ground conductor on a pipe in accordance with one or more embodiments.

Referring to FIG. 8B, which is a diagram that illustrates field lines extending from a signal conductor 110 to a relatively narrow ground plane 802 of a ground conductor 114 on a pipe 104 in accordance with one or more embodiments, a ground plane 802 with a relatively small width (e.g., having an arc length spanning a lesser portion of the curvature of the second/lower/bottom side of the pipe 104), may cause the field lines to pass primarily through the central portion of the interior pipe 104 and terminate along the ground plane 802, with a smaller number of the field lines extending through the edge/side portions of the interior of the pipe 104. As a result, the field lines may pass through the lower/center portion of the interior of the pipe 104, but may not pass through the edge/side portions of the interior of the pipe 104. Such an embodiment (e.g., incorporating a relatively narrow ground plane 802) may be sensitive to relative percentage change of oil and water which occurs in the lower/central portion of the interior of the pipe 104, but may not be very sensitive to relative percentage change of oil and water which occurs in the edge/side portions of the interior of the pipe 104. Accordingly, the width (or "arc length") of the ground plane 802 can play significant role in the performance of a WC sensor. As described herein, embodiments may employ a ground plane having a width that reduces fringing of the field and, thus, provides improved sensitivity. That is, a ground plane may be of an optimum size (e.g., to provide field lines that are similar to that shown in FIG. 8B) to provide improved performance.

In some instances, a minimum fringing field point can depend on the medium inside the pipe 104. Given this dependency, a parametric study on the arc length size of the ground plane 802 can be conducted for at least two extreme cases (e.g., a pipe filled with water and pipe filled with oil), and the study may be used to determine the arc length (e.g., the width) of the ground plane 802 to be used. Starting from an arc length of about 64 mm, for example, the arc length of the ground plane 802 may be decreased and tested iteratively, in an effort to expose a valley point where a minimum resonant frequency of T-resonator occurs. Decreasing the size of ground plane 802 may cause decrement in fringing through air and increment in the effective permeability ($\varepsilon_{\it eff}$) experienced for a T-resonator. This may, in turn, decrease the resonant frequency as explained above. Moreover, decreasing the arc length of the ground plane 802 beyond the valley point may causes the E fields to terminate at the ground ring instead of the ground plane 802 (e.g., as described with regard to FIG. 8A). Decreasing the arc length of the ground plane 802 beyond the valley point may also hinder the propagation of microwaves along the full length of the shunt stub, causing an increase in resonance frequency. A smaller ground plane 802 created by decreasing the ground plane arc length beyond the valley point can also cause radiation loss, which may be undesirable. This being said, it may be desirable to employ a ground plane 802 having an arc length that corresponds the valley for a particular medium inside the pipe.

Figure 9A:
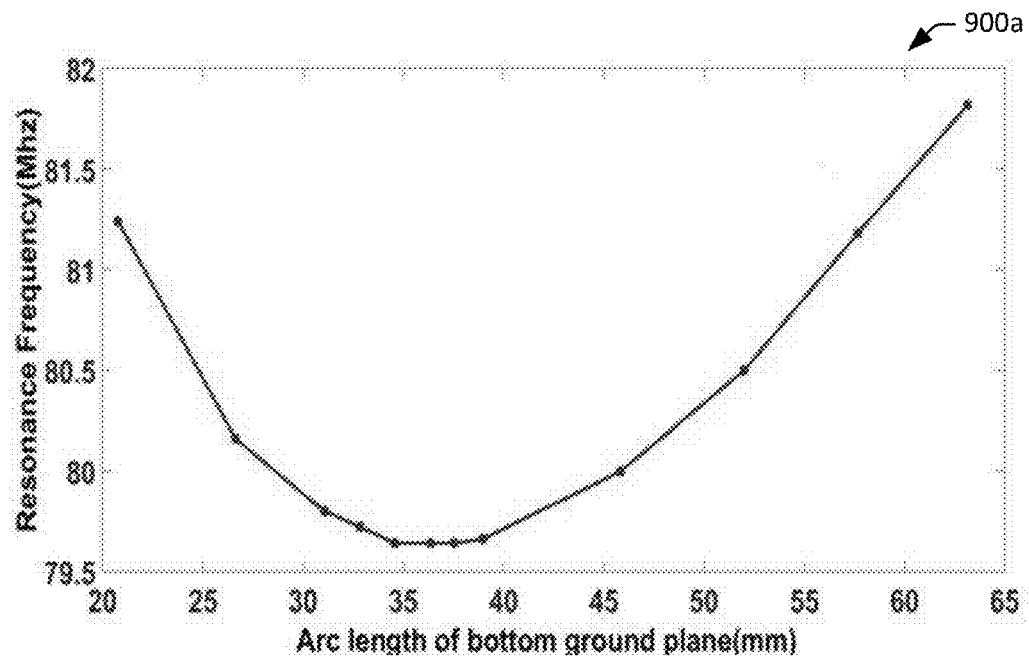
FIG. 9A is a plot diagram that illustrates example results for resonance frequency versus different arc lengths (or widths) of a ground plane employed on a pipe filled with water in accordance with one or more embodiments.

FIG. 9A is a plot 900a that illustrates example results for resonance frequency versus different arc lengths of a ground plane employed on a pipe filled with water in accordance with one or more embodiments. A valley point (or range) for a water filled pipe may occur where a slope of the curve is about zero. In the illustrated embodiment, the valley point (or range) may be determined to occur at an arc length of about 35-40 mm.

Figure 9B:
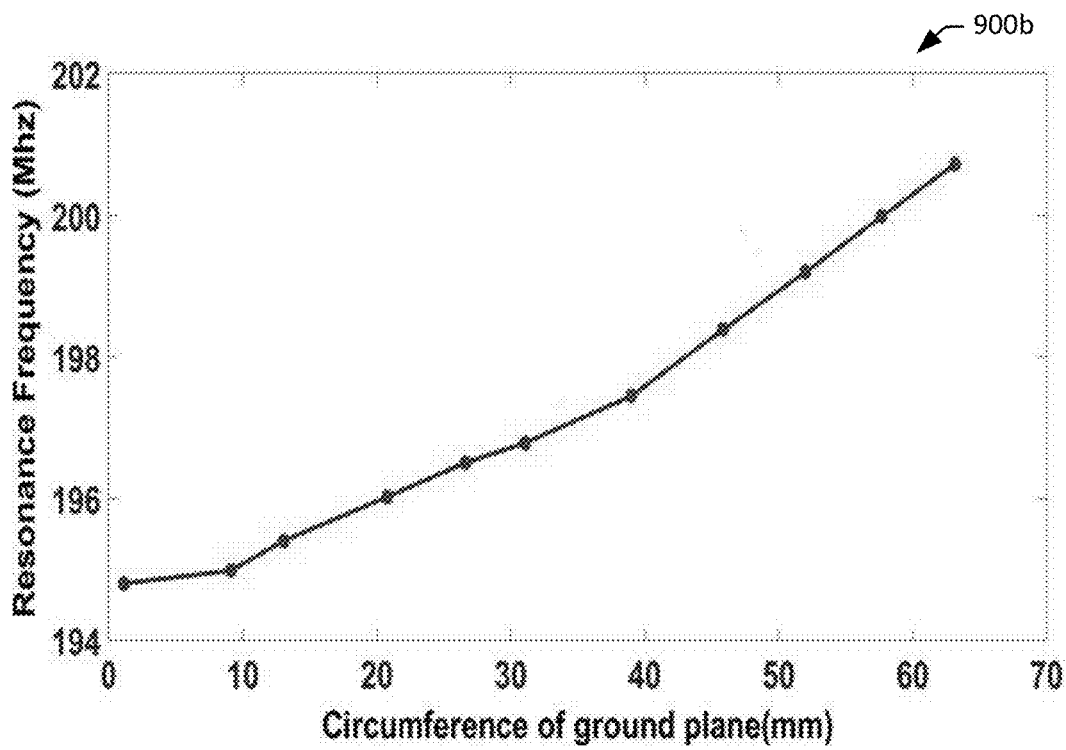
FIG. 9B is a plot diagram that illustrates example results for resonance frequency versus different arc lengths (or widths) of a ground plane employed on a pipe filled with oil in accordance with one or more embodiments.

FIG. 9B is a plot 900b that illustrates example results for resonance frequency versus different arc lengths of a ground plane employed on a pipe filled with oil in accordance with one or more embodiments. Fringing fields may be less common for the case of water because of its higher electric permittivity, but may be less common for the case of oil because due to its lower electric permittivity. Although the plot 900b does not appear to illustrate a well-defined valley point (or range) in case of oil, in the illustrated embodiment, the valley point (or range) may be determined to occur at an arc length of about 2-10 mm. In some embodiments, the arc length of a ground plane employed on a WC sensor for sensing water-cut of a mixture of fluids may be determined based on arc lengths determined for some or all of the fluids present in the mixture. For example, the arc length of the ground plane may be determined as the average of the arc length determined for each of the fluids in the mixture. Continuing with the above example, where a first arc length of about 37.5 mm is determined for the case of a pipe filled with water (e.g., an average of the arc length range of about 35-40 mm) and a second arc length of about 6 mm is determined for the case of a pipe filled with oil (e.g., an average of the arc length range of about 2-10 mm), the arc length for the ground plane for a WC sensor used to measure water-cut of a mixture of water and oil may be determined to be about 22 mm (e.g., ([(35+40)/2]+[(2+10)/2])/2). In such an embodiment, the ground plane of a WC sensor for use in detecting water-cut of a mixture of oil and water in a pipe having an outside diameter of about 50 mm may have an arc-length (or width) of about 22 mm (e.g., about 14% of the pipe circumference).

In some embodiments, the ground plane may have a length that is greater than the length of the resonator. Continuing with the above example of a pipe having an outer diameter of 50 mm and the open shunt stub having a length of about 250 mm in, the ground plane may have a length of about 300 mm. The length of "bottom" ground plane should be sufficient enough only to span the area of overlying T-resonator. A longer bottom ground plane can affect the fringing field pattern, and hence the performance of the WC sensor. The length of the bottom ground plane may be scaled, e.g., to account for different pipe sizes.

Figure 10A:
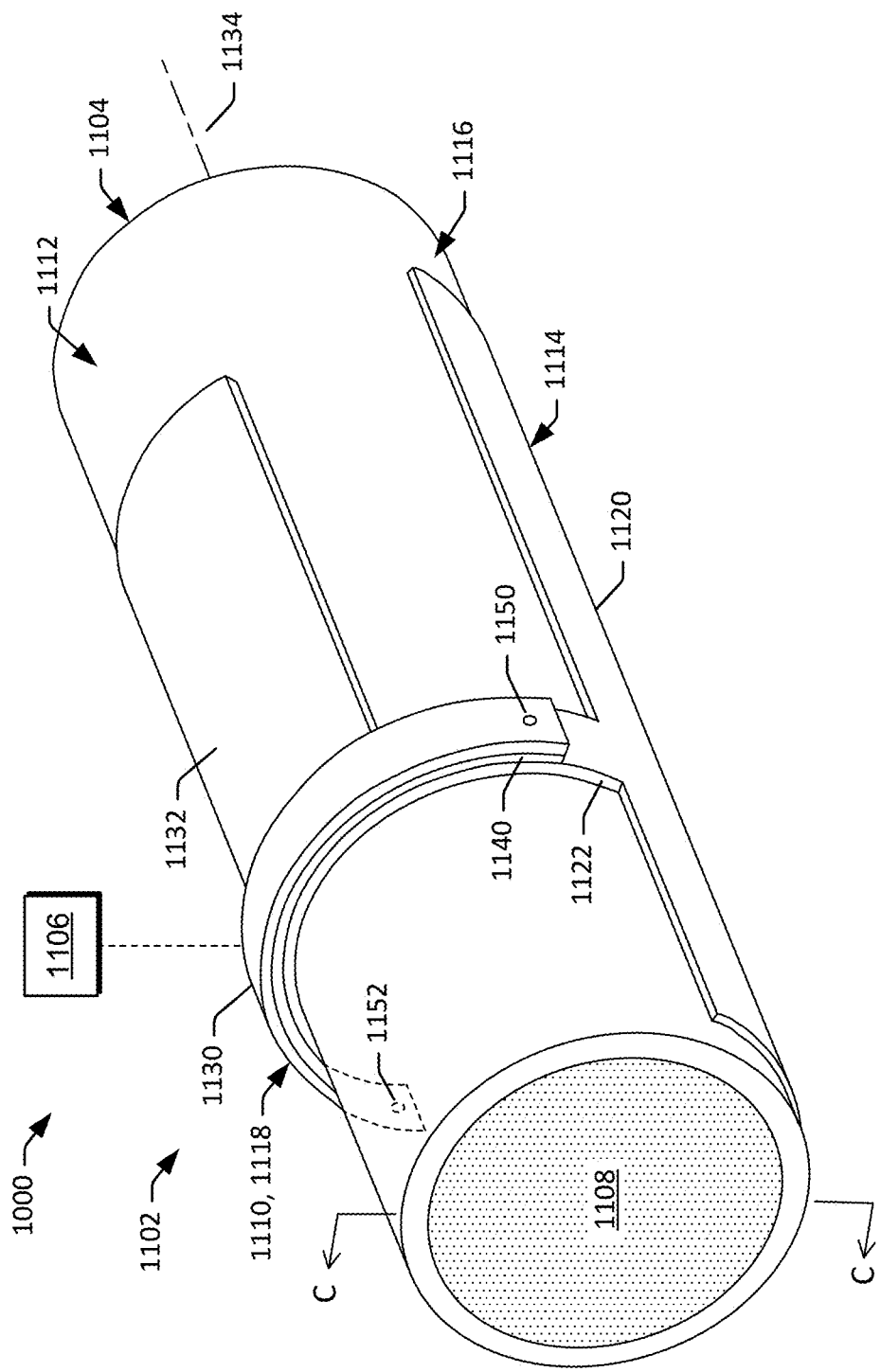
FIGS. 10A-E are diagrams that illustrate of various views of an example embodiment of a water-cut sensing system employing a straight T-resonator and a complementary straight ground conductor in accordance with one or more embodiments.
Figure 10B:
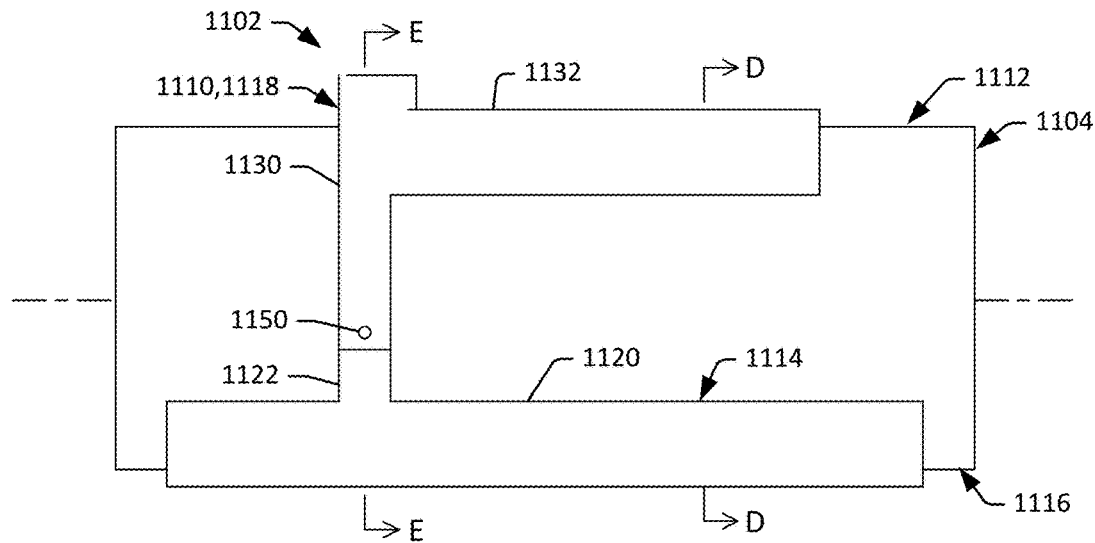
Figure 10C:
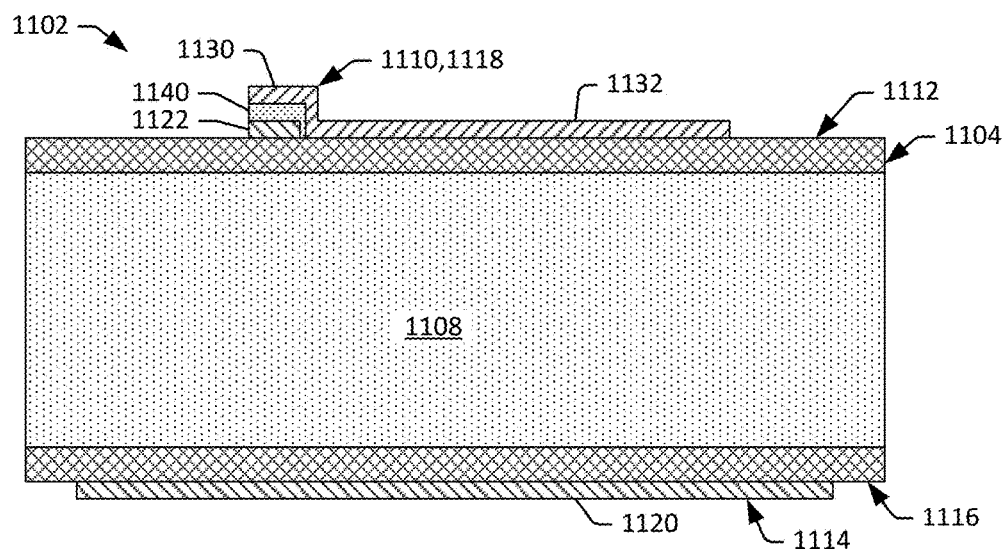
Figure 10D:
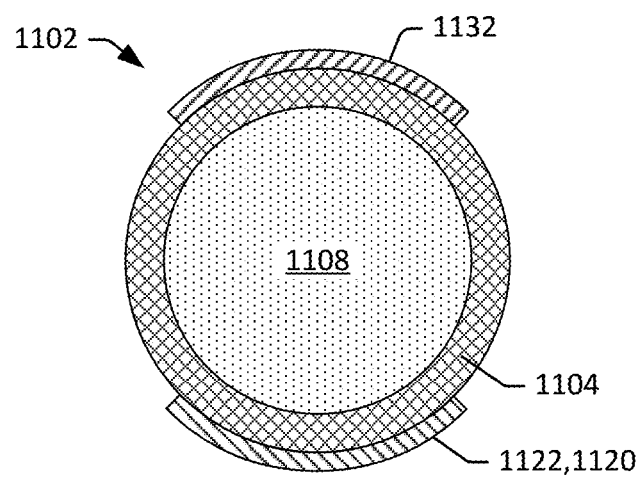
Figure 10E:
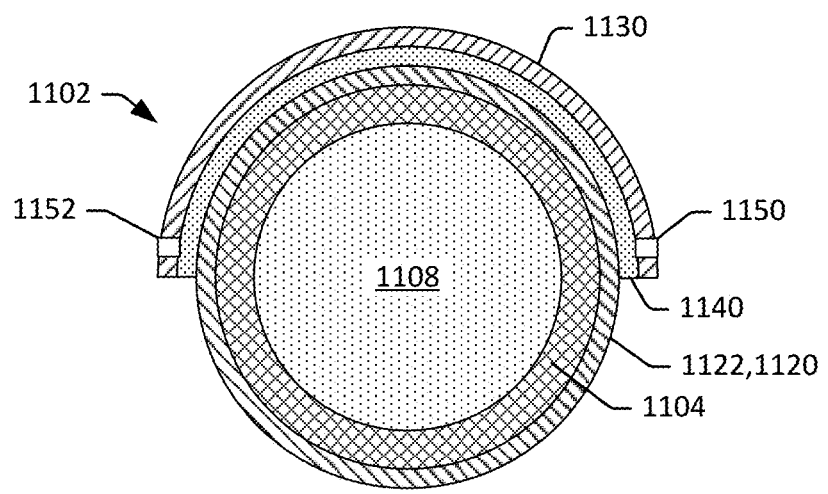

FIGS. 10A-E are diagrams that illustrate of various views of an example embodiment of a water-cut (WC) sensing system 1000 employing a straight T-resonator and a complementary straight ground conductor in accordance with one or more embodiments. More specifically, FIG. 10A is an isometric view of the WC sensing system 1000, FIG. 10B is an side view of the WC sensing system 1000, FIG. 10C is a cross-sectional side view of the WC sensing system 1000 taken along the line C-C of FIG. 10A, FIG. 10D is a cross-sectional end view of the WC sensing system 1000 taken along the line D-D of FIG. 10B, and FIG. 10E is a cross-sectional end view of the WC sensing system 1000 taken along the line E-E of FIG. 10B. Based at least on the shape of the T-resonator of the system 1000, the WC sensing system 1000 may be referred to as a "straight" WC sensing system 1000.

In some embodiments, the WC sensing system 1000 includes a water-cut (WC) sensor 1102, a cylindrical pipe 1104, and/or a measurement processing system 1106. As discussed herein, the WC sensor 1102 may be disposed on (or otherwise integrated within) a wall of the cylindrical pipe

1104. In some embodiments, the WC sensor 1102 includes a signal conductor (SC) 1110 (e.g., a first conductive plane), such as a "straight" T-resonator, disposed at a first/upper/top surface 1112 of the cylindrical pipe 1104, and a ground conductor (GC) 1114 (e.g., a second conductive plane) disposed at a second/lower/bottom surface 1116 of the cylindrical pipe 1104 that is opposite the first/upper/top surface 1112 of the pipe 1104. In such a configuration, the WC sensing system 1100 can be employed to sense a water-cut of a fluid 1108 (e.g., a water and oil mixture, or other substrate) flowing through or otherwise present in the section of the pipe 1104 at or near the WC sensor 1102 (e.g., between the signal conductor 1110 and the ground conductor 1114).

In some embodiments, the signal conductor 1110 includes a "straight" T-resonator 1118. For example, the signal conductor 1110 may include a T-resonator 1118 including a sheet of generally "T" shaped conductive material (e.g., copper) disposed along the length of the first/upper/top surface 1112 of the pipe 1104. The ground conductor 1114 may include a "main" or "bottom" ground plane (GP) 1120 and a ground ring (GR) 1122. The ground plane 1120 may be a generally rectangular shaped conductive sheet of material (e.g., copper) that is disposed along the length of the second/lower/bottom surface 1116 of the pipe 1104. The ground plane 1120 may be arranged to extend longitudinally along the length of the surface of the pipe 1104 (e.g., parallel to the longitudinal axis 1134 of the pipe 1104). The ground ring 1122 may include a band of conductive sheet of material (e.g., copper) that is disposed (e.g., wrapped) around the circumference (e.g., the outer diameter) of the pipe 1104. The ground ring 1122 may be arranged to extend laterally about the circumference of the pipe 1104 (e.g., perpendicular to the longitudinal axis 1134 of the pipe 1104).

In some embodiments, a portion of the T-resonator 1118 of the signal conductor 1110 at least partially overlaps a portion of the ground ring 1122 of the ground conductor 1114. For example, the T-resonator 1118 may include a feed line (FL) 1130 and an open shunt stub (SS) 1132. The feed line 1130 may include the "top" portion of the "T" shape of the T-resonator 1118, and the open shunt stub 1132 may include the "bottom" portion of the "T" shape of the T-resonator 1118. The feed line 1130 may be arranged to extend laterally about the circumference of the pipe 1104 (e.g., perpendicular to the longitudinal axis 1134 of the pipe 1104). The open shunt stub 1132 may be arranged to extend longitudinally along the length of the surface of the pipe 1104 (e.g., parallel to the longitudinal axis 1134 of the pipe 1104). The feed line 1130 may wrap about an upper portion of the circumference of the pipe 1104 by a first distance, and the open shunt stub 1132 may wrap about an upper portion of the circumference of the pipe 104 by a second distance that is less than the first distance. The ground ring 1122 may similarly be wrapped about the circumference of the pipe 1104, including around at least the upper portion of the pipe 1104 about which the feed line 1130 is wrapped. Further, in some embodiments, the feed line 1130 of the T-resonator 1118 may overlap at least a portion of the ground ring 1122 such that at least this portion of the ground ring 1122 is disposed (or "sandwiched") between feed line 1130 and the surface of the pipe 1104.

In some embodiments, a dielectric separator 1140 is provided between at least the overlapping portions of the signal conductor 1110 and the ground conductor 1114 to physically and/or electrically isolate them from one another. For example, a dielectric separator 1140 may include a strip of dielectric material (e.g., a Teflon strip) about the size of (or larger than) the feed line 1130 and that is disposed between the feed line 1130 and the overlapped portion of the ground ring 1122 to maintain physical and/or electrical isolation of the signal conductor 1110 (e.g., including the T-resonator 1118) from the ground conductor 1114. In some embodiments, the dielectric separator 1140 may be of a constant thickness (e.g., about 1 mm) to maintain a constant distance between the overlapping portions of the signal conductor 1110 (e.g., including the T-resonator 1118) and the ground conductor 1114.

In some embodiments, the signal conductor 1110 includes a first/input port 1150 for input of a source signal of a first frequency and phase, and a second/output port 1152 for output of a corresponding response signal of a second frequency and phase. Continuing with the above example employing the T-resonator 1118, the first/input port 1150 may be located at or near a first end of the feed line 1130, and the second/output port 1152 may be located at or near a second end of the top portion of the feed line 1130 (opposite the first end). Electrical leads of the measurement processing system 1106 may be coupled to the ports 1150 and 1152 for introducing source signals and sensing response signals. For example, an input lead for introducing a source signal may extend from an output circuit of the measurement processing system 1106 to the first/input port 1150, and an output lead for sensing the response signal may extend from an input circuit of the measurement processing system 1106 to the second/output port 1152. As described herein, the measurement processing system 1106 may provide and sense the respective signals and use the characteristics of the signals to determine a water-cut of the fluid 1108 in the pipe 1104.

During use the fluid 1108 (e.g., a production fluid including a mixture of oil and water) flows through the center of the pipe 1104 such that the fluid 1108 passes between at least a portion of the signal conductor 1110 disposed on the first/upper/top surface 1112 of the pipe 1104 and at least a portion of the ground conductor 1114 disposed on the second/lower/bottom surface 1116 of the pipe 1104. For example, if the WC sensor 1102 is disposed on a length (or section) of the pipe 1104 used to transport production fluid including a mixture of oil and water) from a well, the production fluid may flow through the pipe 1104, between the signal conductor 1110 and the ground conductor 1114 disposed on opposite sides of the pipe 1104. A source signal can be introduced into the signal conductor 1110 while the fluid 1108 is flowing through the pipe 1104 (or otherwise present in the pipe 1104), and a corresponding response signal present at the signal conductor 1110 can be sensed. For example, a source signal of a first/predetermined frequency and phase can be introduced at the first/input port 1150, and a corresponding response signal of a second/resulting frequency and phase can be sensed at the second/output port 1152. As described herein, the source signal may be generated by the measurement processing system 1106. For example, the measurement processing system 1106 may include a vector network analyzer (VNA), and the source signal may be generated by a source circuit, such as a signal generator, of the vector network analyzer (VNA). As described herein, in some embodiments, the response signal may be sensed/measured by the measurement processing system 1106. For example, a sensing circuit, such as a receiver of the vector network analyzer (VNA), may receive the response signal. In some embodiments, the signals may be processed by the measurement processing system 1106 to determine various characteristics of the fluid 1108, such as the water-cut of the fluid 1108. For example, the measurement processing system 1106 may include a processor, such as a computer processor of the vector network analyzer (VNA) and/or other computing devices, that analyzes the characteristics of the source signal and/or the corresponding response signal to determine the resonant frequency of the WC sensor 1102 in the presence of the fluid 1108 (e.g., a resonant frequency of the T-resonator with the fluid 1108 currently flowing through or otherwise located in the pipe 1104, between the signal conductor 1110 and the ground conductor 1114). Based on a predetermined correlation between the water-cut of a fluid mixture flowing through the pipe 104 and the resonant frequency of the WC sensor 1102, the water-cut of the fluid 1108 flowing through the pipe 104 can be determined. That is, the water-cut of the fluid 1108 passing through the pipe 1108 can be determined based on the resonant frequency of the WC sensor 1102 at or near the time when the fluid 1108 passes through the WC sensor 1102.

Figure 11A:
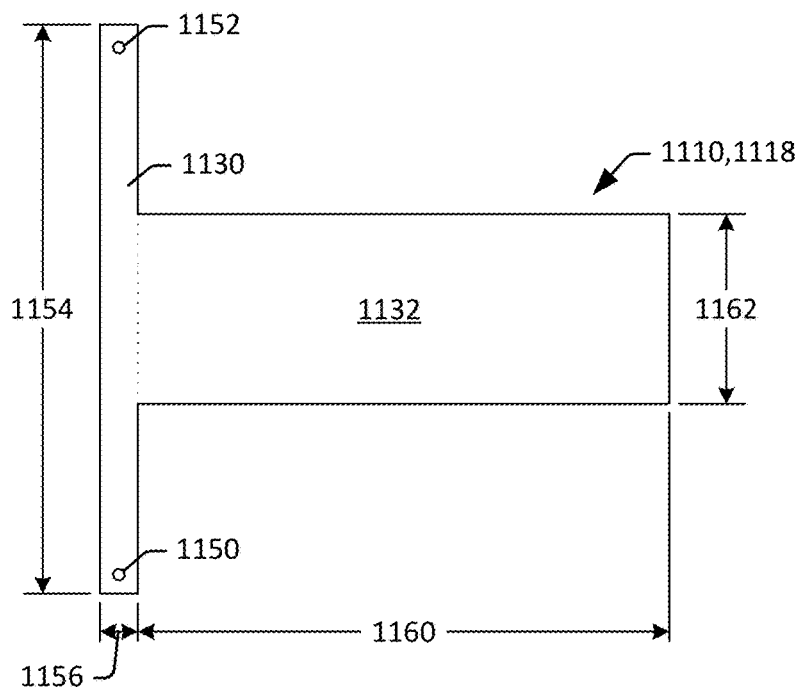
FIG. 11A is a diagram that illustrates a planar view of the straight T-resonator of FIGS. 10A-10E in accordance with one or more embodiments.
Figure 11B:
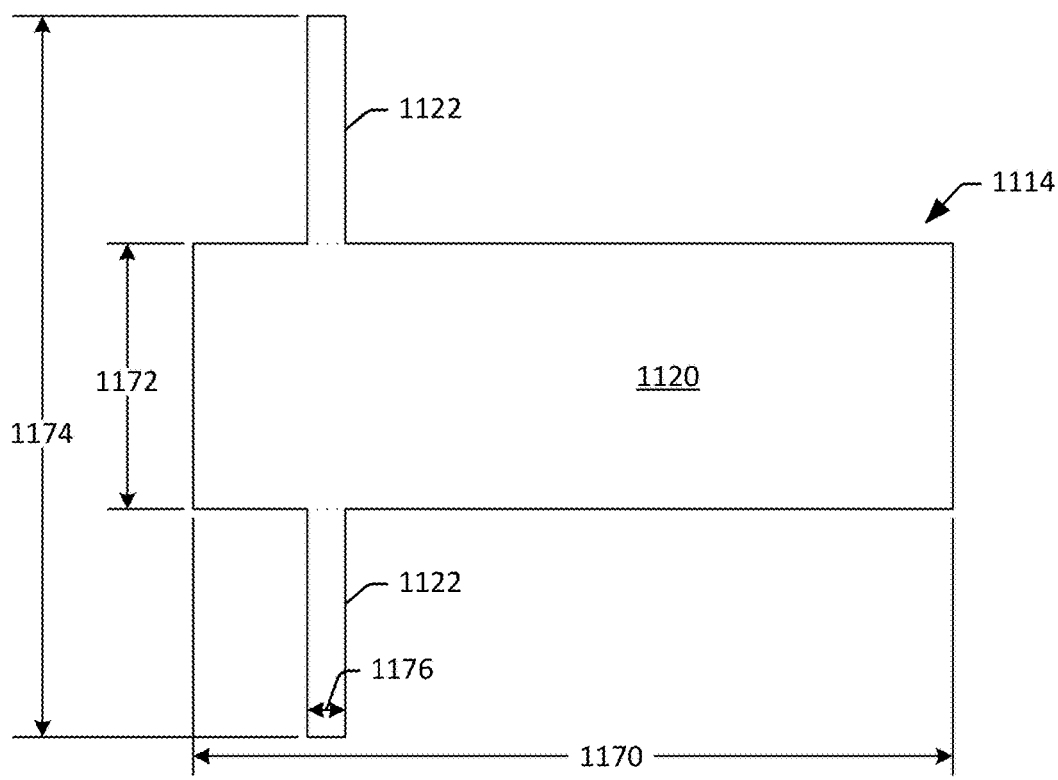
FIG. 11B is a diagram that illustrates a planar view of the straight ground conductor of FIGS. 10A-10E in accordance with one or more embodiments.

FIG. 11A is a diagram that illustrates a planar view of the "straight" T-resonator 1118 in accordance with one or more embodiments. This view may represent the planar shape of the T-resonator 1118 if it was laid flat (or "unwrapped"), as opposed to being disposed on the curved surface of the pipe 1104. FIG. 11B is a diagram that illustrates a planar view of the ground conductor 1114 in accordance with one or more embodiments. This view may represent the planar shape of the ground conductor 1114 if it was laid flat (or "unwrapped"), as opposed to being disposed on the curved surface of the pipe 1104, and the ground ring 1122 was "broken" as opposed to being contiguously wrapped about the pipe 1104.

In an example embodiment, the pipe 1104 may have an internal diameter of about 46 mm and an outer diameter of about 50 mm. Consistent with the dimensioning discussed above, and referring to FIG. 11A, the feed line 1130 may have a length (or arc length) 1154 of about 45 mm and a width 1156 of about 2.5 mm, and the open shunt stub 1132 may have a length 1160 of about 250 mm and a width (or arc length) 1162 of about 25.4 mm. With reference to FIG. 11B, the ground plane 1120 may have a length 1170 of about 300 mm and a width (or arc length) 1172 of about 22 mm, and the ground ring 1122 may have a length (or arc length) 1174 of about 157 mm (e.g., the circumference of the pipe 1104) and a width 1176 of about 6.3 mm. The separator 1140 may have a length (or arc length) of about 45 mm and a width of about 6.3 mm.

Figure 12A:
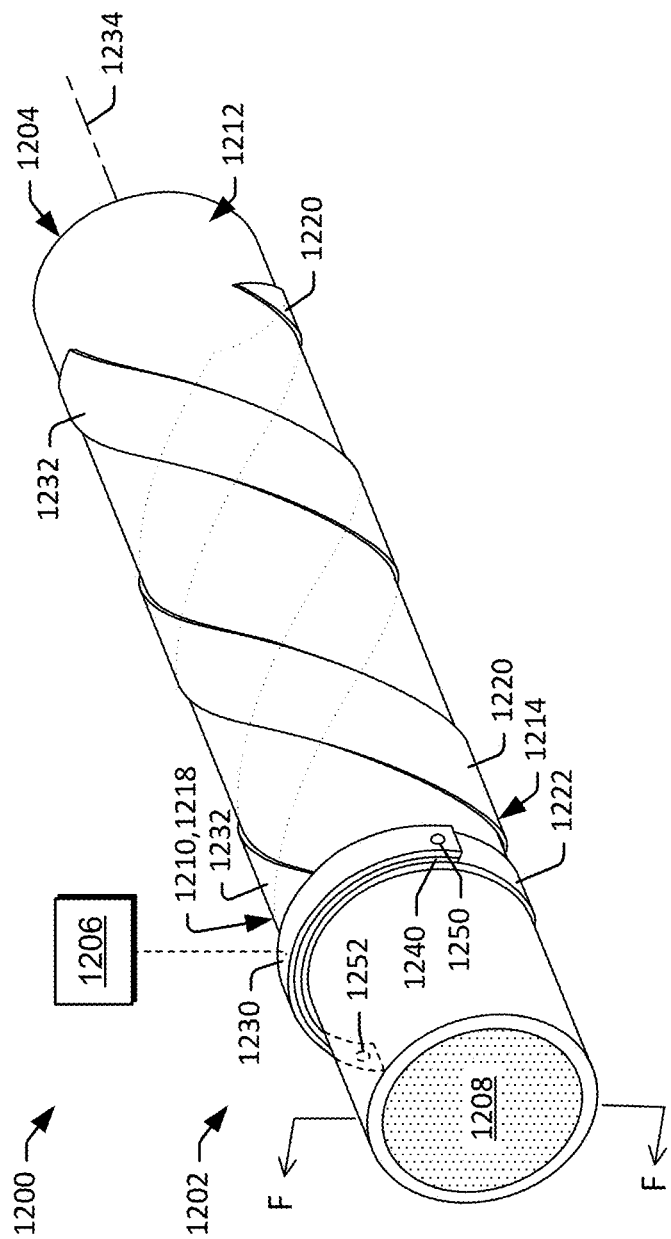
FIGS. 12A-E are diagrams that illustrate of various views of an example embodiment of a water-cut sensing system employing a helical T-resonator and a complementary helical ground conductor in accordance with one or more embodiments.
Figure 12B:
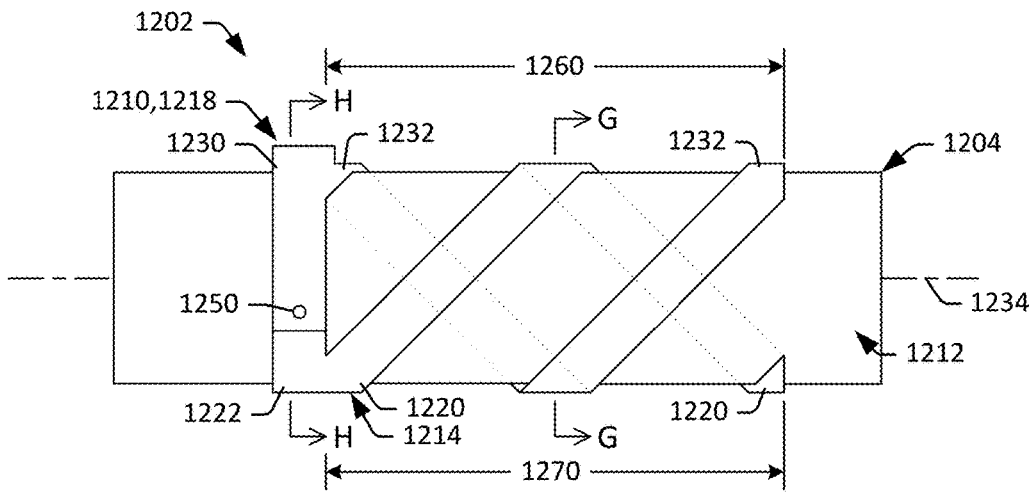
Figure 12C:
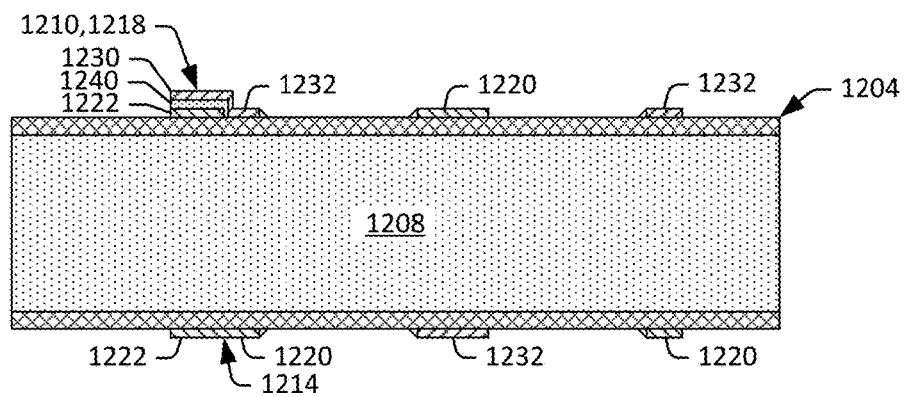
Figure 12D:
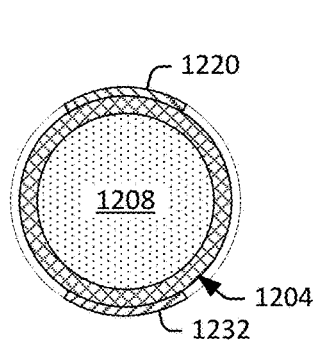
Figure 12E:
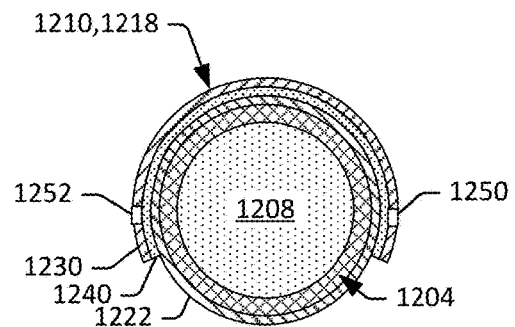

FIGS. 12A-E are diagrams that illustrate of various views of an example embodiment of a water-cut (WC) sensing system 1200 employing a single helical T-resonator and a complementary single helical ground conductor in accordance with one or more embodiments. More specifically, FIG. 12A is an isometric view of the WC sensing system 1200, FIG. 12B is an side view of the WC sensing system 1200, FIG. 12C is a cross-sectional side view of the WC sensing system 1200 taken along the line F-F of FIG. 12A, FIG. 12D is a cross-sectional end view of the WC sensing system 1200 taken along the line G-G of FIG. 12B, and FIG. 12E is a cross-sectional end view of the WC sensing system 1200 taken along the line H-H of FIG. 12B. Based at least on the shape and configuration of the T-resonator of the system 1200, the WC sensing system 1200 may be referred to as a "single helical" WC sensing system 1200.

In some embodiments, the WC sensing system 1200 includes a water-cut (WC) sensor (e.g., a single helical WC sensor) 1202, a cylindrical pipe 1204, and/or a measurement processing system 1206. As discussed herein, the water-cut (WC) sensor 1202 may be disposed on (or otherwise integrated within) a wall of the cylindrical pipe 1204. In some embodiments, the WC sensor 1202 includes a "helical" signal conductor (SC) 1210 (e.g., a first conductive plane), such as a "helical" T-resonator, disposed on a surface 1212 of the cylindrical pipe 1204, and a "helical" ground conductor (GC) 1214 (e.g., a second conductive plane) disposed on the surface 1212 of the cylindrical pipe 1204. In such a configuration, the WC sensing system 1200 can be employed to sense a water-cut of a fluid 1208 (e.g., a water and oil mixture, or other substrate) flowing through or otherwise present in the section of the pipe 1204 at or near the WC sensor 1202 (e.g., between the signal conductor 1210 and the ground conductor 1214).

In some embodiments, the signal conductor 1210 includes a "helical" T-resonator 1218 that includes a feed line 1230 and an elongated helical open shunt stub 1232. The feed line 1230 may form the "top" portion of the "T" shape of the helical T-resonator 1218, and the helical open shunt stub 1232 may form the "bottom" portion of the "T" shape of the T-resonator 1218. The feed line 1230 may include a band of conductive material that extends laterally about at least a portion of the circumference of the pipe 1204 (e.g., perpendicular to a longitudinal axis 1234 of the pipe 1204). The helical open shunt stub 1232 may extend from a central portion of the feed line 1230, in a spiral pattern along the surface 1212 of the pipe 1204 and around the longitudinal axis 1234 of the pipe 1204. The helical open shunt stub may, for example, make a single wrap about the circumference of the pipe 1204, as illustrated. In some embodiments, the signal conductor 1210 includes a contiguous sheet of conductive material (e.g., copper) disposed on the surface 1212 of the pipe 1204 to form the feed line 1230 and the elongated helical open shunt stub 1232.

In some embodiments, the ground conductor 1214 includes a ground ring (GR) 1222 and a helical ground plane (GP) 1220. The ground ring 1222 may include a band of conductive material that extends laterally about the circumference of the pipe 1204 (e.g., perpendicular to the longitudinal axis 1234 of the pipe 1204). The helical ground plane 1220 may include a strip of conductive material that extends from the ground ring 1222, in a spiral pattern along the surface 1212 of the pipe 1204 and around the longitudinal axis 1234 of the pipe 1204. In some embodiments, the ground conductor 1214 includes a contiguous sheet of conductive material (e.g., copper) disposed on the surface 1212 of the pipe 1204 to form the ground ring 1222 and the helical ground plane 1220. In some embodiments, corresponding portions of the helical open shunt stub 1232 and the helical ground plane 1220 are located on opposite surfaces/sides of the pipe 1204 from one another to form a pair of complementary helical conductors that spiral opposite one another along a length of the pipe 1204.

The feed line 1230 may overlap at least a portion of the ground ring 1222 such that at least this portion of the ground ring 1222 is disposed (or "sandwiched") between feed line 1230 and the surface of the pipe 1204. A dielectric separator 1240 may be provided between at least the overlapping portions of the signal conductor 1210 and the ground conductor 1214 to physically and/or electrically isolate them from one another. For example, the dielectric separator 1240 may include a strip of dielectric material (e.g., a Teflon strip) about the size of (or larger than) the feed line 1230 and that is disposed between the feed line 1230 and the overlapped portion of the ground ring 1222 to maintain physical and/or electrical isolation of the signal conductor 1210 (e.g., including the helical T-resonator 1218) and the ground conductor 1214. The dielectric separator 1240 may be of a constant thickness (e.g., about 1 mm) to maintain a constant distance between the overlapping portions of the signal conductor 1210 (e.g., including the helical T-resonator 1218) and the ground conductor 1214.

The signal conductor 1210 may include a first/input port 1250 for input of a source signal of a first frequency and phase, and a second/output port 1252 for output of a corresponding response signal of a second frequency and phase. The first/input port 1250 may be located at or near a first end of the feed line 1230, and the second/output port 1252 may be located at or near a second end of the feed line 1230 that is opposite the first end. Electrical leads of the measurement processing system 1206 may be coupled to the ports 1250 and 1252 for introducing source signals and sensing response signals. For example, an input lead for introducing a source signal may extend from an output circuit of the measurement processing system 1206 to the first/input port 1250, and an output lead for sensing the response signal may extend from an input circuit of the measurement processing system 1206 to the second/output port 1252. As described herein, the measurement processing system 1206 may provide and sense the respective signals and use the characteristics of the signals to determine a water-cut of the fluid 1208 in the pipe 1204.

During use, the fluid 1208 (e.g., a production fluid including a mixture of oil and water) may flow through the center of the pipe 1204 such that the fluid 1208 passes between at least a portion of the signal conductor 1210 and at least a portion of the ground conductor 1214. For example, if the WC sensor 1202 is disposed on a length (or section) of the pipe 1204 used to transport production fluid including a mixture of oil and water) from a well, the production fluid may flow through the pipe 1204, between the signal conductor 1210 and the ground conductor 1214. A source signal can be introduced into the signal conductor 1210 while the fluid 1208 is flowing through the pipe 1204 (or otherwise present in the pipe 1204), and a corresponding response signal present at the signal conductor 1210 can be sensed. For example, a source signal of a first/predetermined frequency and phase can be introduced at the first/input port 1250, and a corresponding response signal of a second/ resulting frequency and phase can be sensed at the second/ output port 1252. As described herein, in some embodiments, the source signal is generated by the measurement processing system 1206. For example, the measurement processing system 1206 may include a vector network analyzer (VNA), and the source signal may be generated by a source circuit, such as a signal generator, of the vector network analyzer (VNA). As describe herein, in some embodiments, the response signal is sensed/measured by the measurement processing system 1206. For example, a sensing circuit, such as a receiver of the vector network analyzer (VNA), may receive the response signal. In some embodiments, the signals are processed by the measurement processing system 1206 to determine various characteristics of the fluid 1208, such as the water-cut of the fluid 1208. For example, the measurement processing system 1206 may include a processor, such as a computer processor of the vector network analyzer (VNA) and/or other computing devices, that analyzes the characteristics of the source signal and/or the corresponding response signal to determine the resonant frequency of the WC sensor 1202 in the presence of the fluid 1208 (e.g., a resonant frequency of the helical T-resonator 1218 with the fluid 1208 currently flowing through or otherwise located in the pipe 1204, between the signal conductor 1210 and the ground conductor 1214). Based on a predetermined correlation between the water-cut of a fluid mixture flowing through the pipe 1204 and the resonant frequency of the WC sensor 1202, the water-cut of the fluid 1208 flowing through the pipe 1204 can be determined. That is, the water-cut of the fluid 1208 passing through the pipe 1208 can be determined based on the resonant frequency of the WC sensor 1202 at or near the time when the fluid 1208 passes through the WC sensor 1202.

Figure 13A:
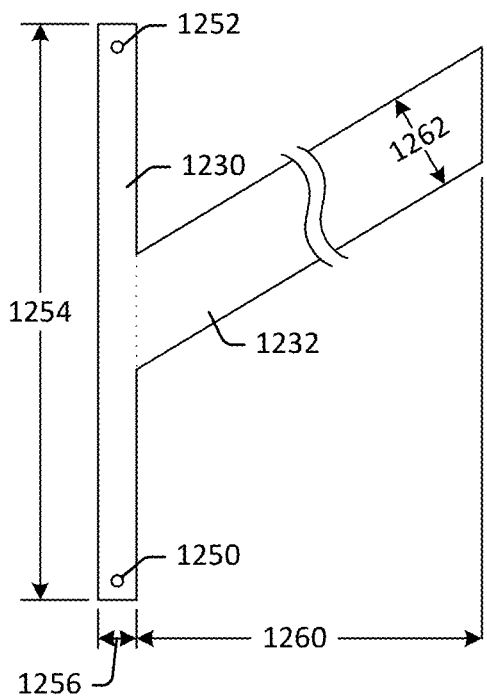
FIG. 13A is a diagram that illustrates a planar view of the helical T-resonator of FIGS. 12A-12E in accordance with one or more embodiments.
Figure 13B:
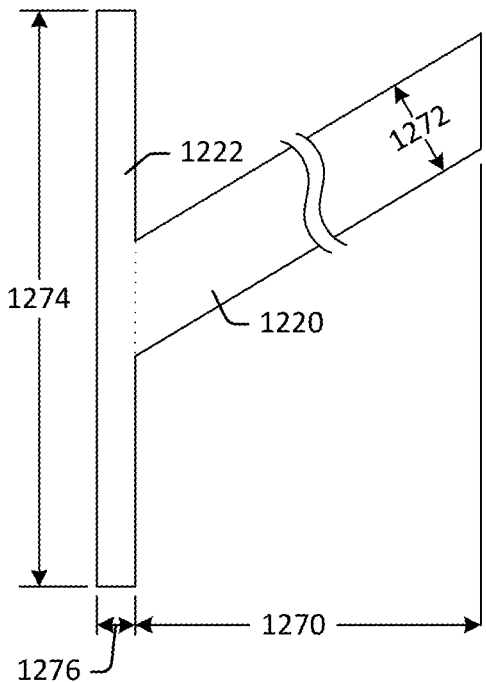
FIG. 13B is a diagram that illustrates a planar view of the helical ground conductor of FIGS. 12A-12E in accordance with one or more embodiments.

FIG. 13A is a diagram that illustrates a planar view of the "helical" T-resonator 1218 in accordance with one or more embodiments. This view may represent the planar shape of the T-resonator 1218 if it was laid flat (or "unwrapped"), as opposed to being disposed on the curved surface of the pipe 1204. FIG. 13B is a diagram that illustrates a planar view of the helical ground conductor 1214 in accordance with one or more embodiments. This view may represent the planar shape of the helical ground conductor 1214 if it was laid flat (or "unwrapped"), as opposed to being disposed on the curved surface of the pipe 1204, and the ground ring 1222 was "broken" as opposed to being contiguously wrapped about the pipe 1204.

In an example embodiment, the pipe 1204 may have an internal diameter of about 46 mm and an outer diameter of about 50 mm. Consistent with the dimensioning discussed above, and referring to FIG. 13A, the feed line 1230 may have a length (or arc length) 1254 of about 45 mm and a width 1256 of about 2.5 mm, and the helical open shunt stub 1232 may have a length 1260 of about 250 mm and a width 1262 of about 25.4 mm. Thus, when wrapped about the pipe 1204, the helical open shunt stub 1232 may extend a distance of about 250 mm along the length of the pipe 1204, as illustrated by distance 1260 in FIG. 12B. With reference to FIG. 13B, the helical ground plane 1220 may have a length 1270 that is the same or similar to that of the length 1270 of the 1260 of the helical open shunt stub 1232 (e.g., a length 1270 of about 250 mm) and a width 1272 that is the same or similar to that of the width 1262 of the helical open shunt stub 1232 (e.g., a width 1272 of about 22 mm), and the ground ring 1222 may have a length (or arc length) 1274 of about 157 mm (e.g., the circumference of the pipe 1204) and a width 1276 of about 6.3 mm. The separator 1240 may have a length (or arc length) of about 45 mm and a width of about 6.3 mm.

Figure 14A:
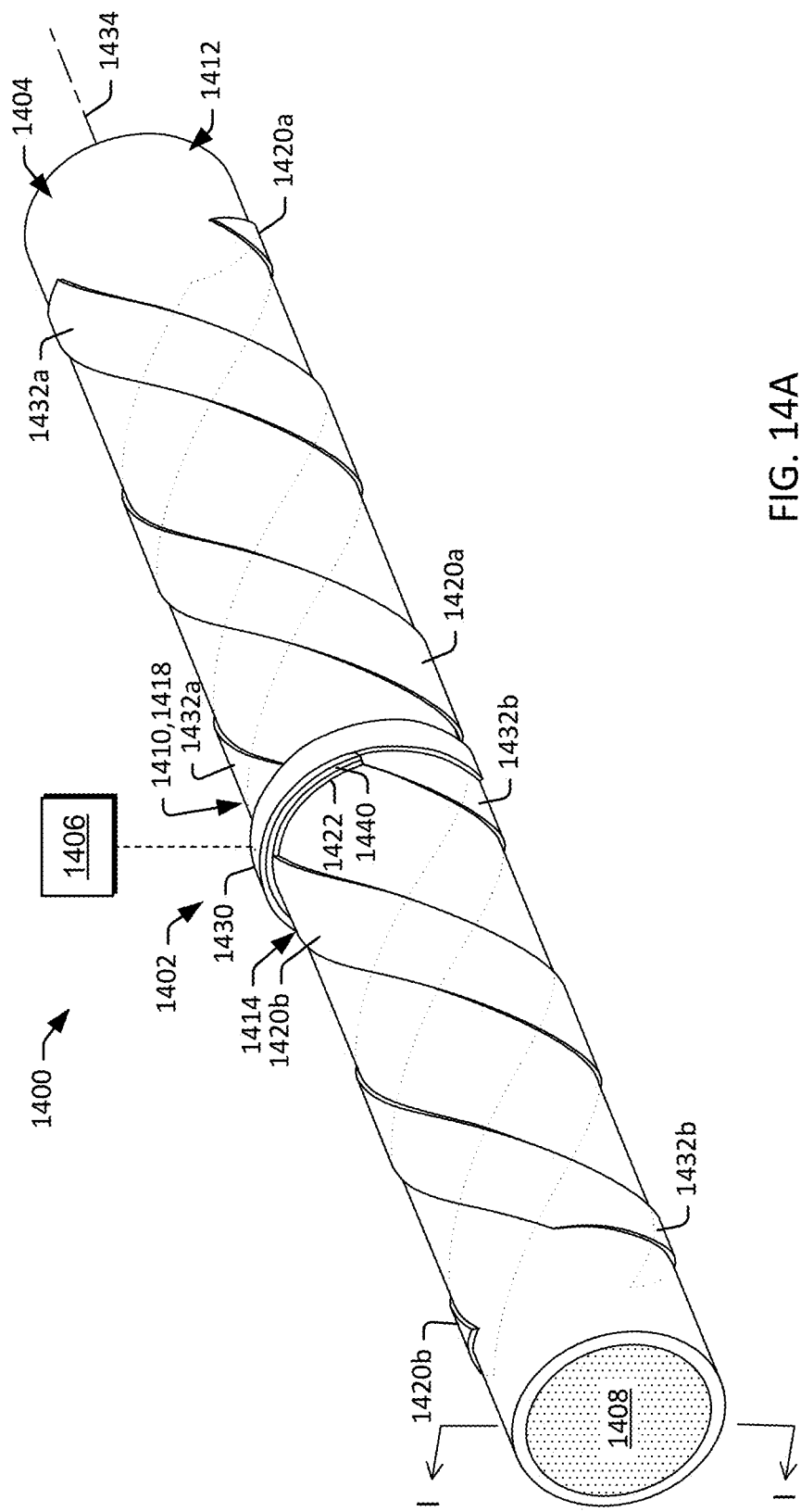
FIGS. 14A-E are diagrams that illustrate of various views of an example embodiment of a water-cut sensing system employing a dual helical T-resonator and a complementary dual helical ground conductors in accordance with one or more embodiments.
Figure 14B:
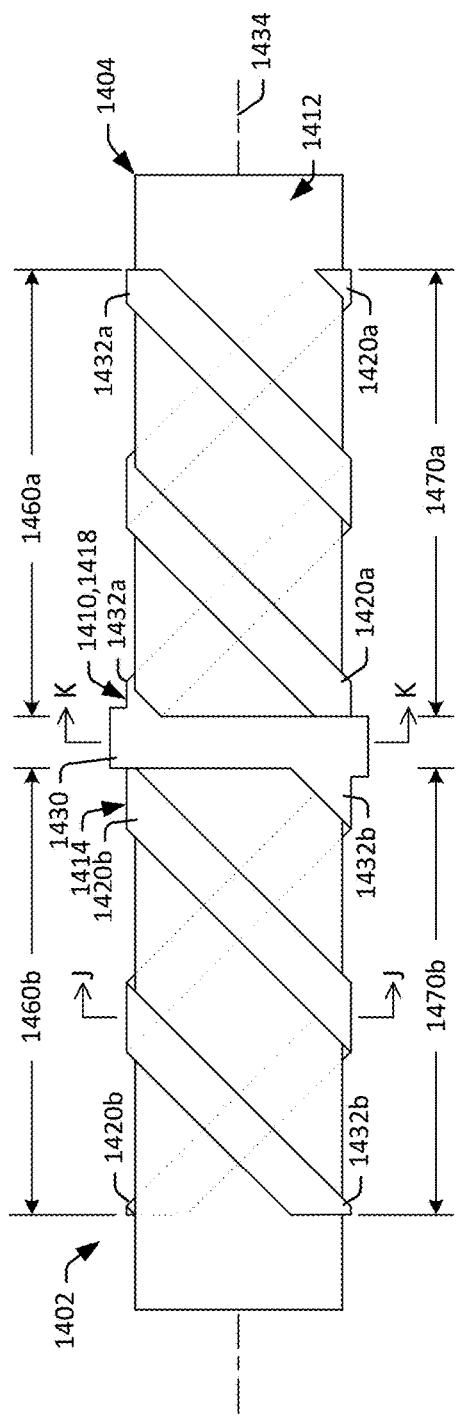
Figure 14C:
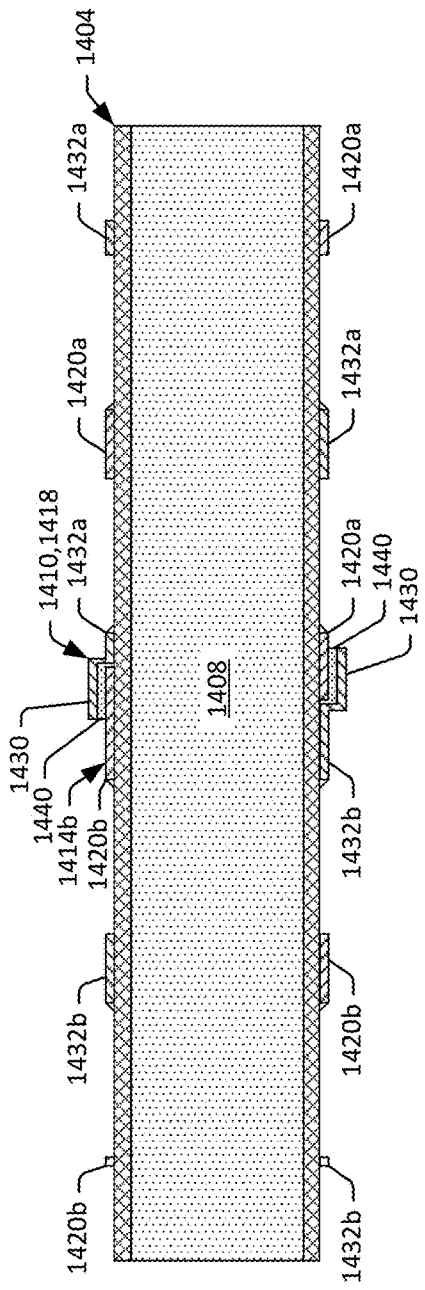
Figure 14E:
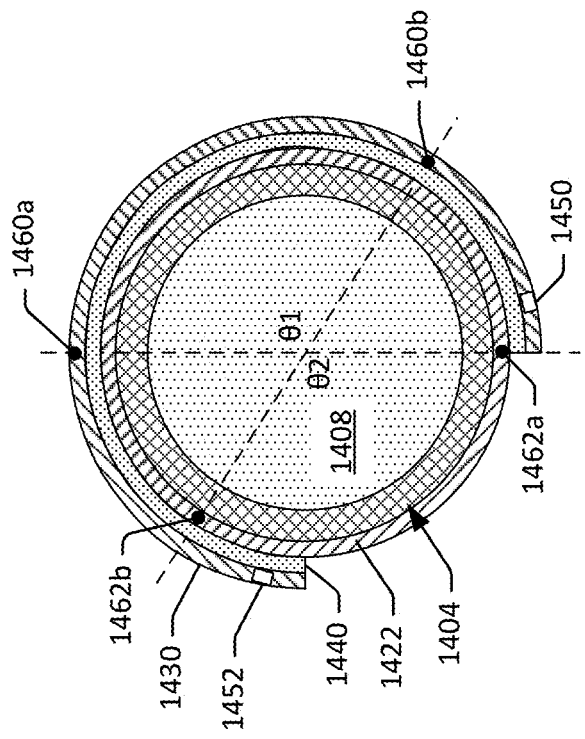
Figure 14D:
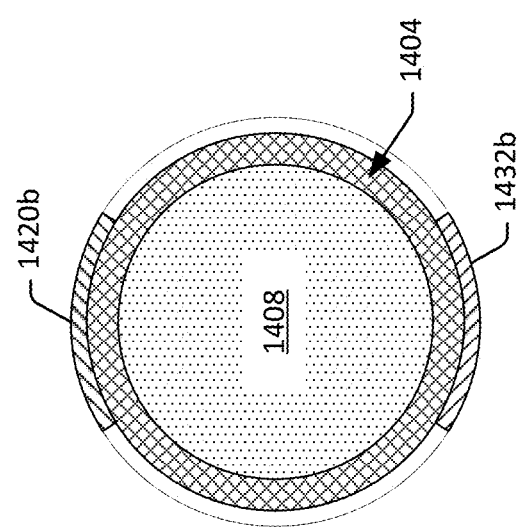

FIGS. 14A-E are diagrams that illustrate of various views of an example embodiment of a water-cut (WC) sensing system 1400 employing a dual helical T-resonator and a complementary dual helical ground conductor in accordance with one or more embodiments. More specifically, FIG. 14A is an isometric view of the WC sensing system 1400, FIG. 14B is an side view of the WC sensing system 1400, FIG. 14C is a cross-sectional side view of the WC sensing system 1400 taken along the line I-I of FIG. 14A, FIG. 14D is a cross-sectional end view of the WC sensing system 1400 taken along the line J-J of FIG. 14B, and FIG. 14E is a cross-sectional end view of the WC sensing system 1400 taken along the line K-K of FIG. 14B. Based at least on the shape and configuration of the T-resonator of the system 1400, the WC sensing system 1200 may be referred to as a "dual helical" WC sensing system 1200.

In some embodiments, the WC sensing system 1400 includes a water-cut (WC) sensor (e.g., a dual helical WC sensor) 1402, a cylindrical pipe 1404, and/or a measurement processing system 1406. As discussed herein, the water-cut (WC) sensor 1402 may be disposed on (or otherwise integrated within) a wall of the cylindrical pipe 1404. In some embodiments, the WC sensor 1402 includes a signal conductor (SC) 1410 (e.g., a first conductive plane), such as a "dual helical" T-resonator, disposed on a surface 1412 of the cylindrical pipe 1404, and a "dual helical" ground conductor (GC) 1414 (e.g., a second conductive plane) disposed on the surface 1412 of the cylindrical pipe 1404. In such a configuration, the WC sensing system 1400 can be employed to sense a water-cut of a fluid 1408 (e.g., a water and oil mixture, or other substrate) flowing through or otherwise present in the section of the pipe 1404 at or near the WC sensor 1402 (e.g., between the signal conductor 1410 and the ground conductor 1414).

In some embodiments, the signal conductor 1410 includes a "dual helical" T-resonator 1418 that includes a common feed line (FL) 1430, a first elongated helical open shunt stub (SS) 1432a and a second elongated helical open shunt stub (SS) 1432b. The feed line 1430 may include a band of conductive material that extends laterally about at least a portion of the circumference of the pipe 1404 (e.g., perpendicular to a longitudinal axis 1434 of the pipe 1404). The first helical open shunt stub 1432a may extend in a first direction from a central portion of the feed line 1230, in a spiral pattern along the surface 1412 of the pipe 1204 and around the longitudinal axis 1234 of the pipe 1404. The second helical open shunt stub 1432b may extend in a second direction (e.g., opposite the first direction) from a central portion of the feed line 1230, in a spiral pattern along the surface 1412 of the pipe 1204 and around the longitudinal axis 1234 of the pipe 1404. The spiral pattern of the first helical open shunt stub 1432a may be the same or similar to that of the second helical open shunt stub 1432b. For example, both of the first helical open shunt stub 1432a and the second helical open shunt stub 1432b may spiral in the same direction (e.g., clockwise) and make a single wrap about the circumference of the pipe 1204, as illustrated. The first helical open shunt stub 1432a may have an angular offset from the second helical open shunt stub 1432b. For example, referring to FIG. 14E, a center of the first helical open shunt stub 1432a may intersect the feed line 1430 at a first location 1460a, and a center of the second helical open shunt stub 1432a may intersect the feed line 1230 at a second location 1460b that is offset by an angle ($\theta_1$) from the first location 1460a. The angle ($\theta_1$) may be, for example, 60 degrees. In some embodiments, the signal conductor 1410 includes a contiguous sheet of conductive material (e.g., copper) disposed on the surface 1412 of the pipe 1404 to form the feed line 1430, the first helical open shunt stub 1432a and the second helical open shunt stub 1432b.

In some embodiments, the ground conductor 1414 includes a ground ring (GR) 1422, a first helical ground plane (GP) 1420a and a second helical ground plane (GP) 1420b. The ground ring 1422 may include a band of conductive material that extends laterally, about the circumference of the pipe 1404 (e.g., perpendicular to the longitudinal axis 1434 of the pipe 1404). The first helical ground plane 1420a may include a strip of conductive material that extends in a first direction from the ground ring 1422, in a spiral pattern along the surface 1412 of the pipe 1404 and around the longitudinal axis 1434 of the pipe 1404. The second helical ground plane 1420b may include a strip of conductive material that extends in a second direction (e.g., opposite the first direction) from the ground ring 1422, in a spiral pattern along the surface 1412 of the pipe 1404 and around the longitudinal axis 1434 of the pipe 1404. The spiral pattern of the first helical ground plane 1420a may be the same or similar to that of the second helical ground plane 1420b. For example, both of the first helical ground plane 1420a and the second helical ground plane 1420b may spiral in the same direction (e.g., clockwise) and make a single wrap about the circumference of the pipe 1204, as illustrated. The first helical ground plane 1420a may have an angular offset from the second helical ground plane 1420b. For example, referring to FIG. 14E, a center of the first ground plane 1420a may intersect the ground ring 1422 at a first location 1462a, and a center of the second helical ground plane 1420b may intersect the ground ring 1422 at a second location 1462b that is offset by an angle ($\theta_2$) from the first location 1462a. The angle ($\theta_2$) may be equal to that of the offset angle for the first and second helical ground planes 1420a and 1420b. For example, the angle ($\theta_2$) may be 60 degrees. In some embodiments, the ground conductor 1414 includes a contiguous sheet of conductive material (e.g., copper) disposed on the surface 1412 of the pipe 1404 to form the ground ring 1422, the first helical ground plane 1420a and the second helical ground plane 1420b. In some embodiments, corresponding portions of the first helical open shunt stub 1432a and the first helical ground plane 1420a are located on opposite surfaces/sides of the pipe 1404 from one another to form a pair of complementary helical conductors that spiral opposite one another along a length of the pipe 1404, and/or corresponding portions of the second helical open shunt stub 1432b and the second helical ground plane 1420b are located on opposite surfaces/sides of the pipe 1404 from one another to form a pair of complementary helical conductors that spiral opposite one another along a length of the pipe 1404.

The feed line 1430 may overlap at least a portion of the ground ring 1422, such that at least this portion of the ground ring 1422 is disposed (or "sandwiched") between feed line 1430 and the surface of the pipe 1404. A dielectric separator 1440 may be provided between at least the overlapping portions of the signal conductor 1410 and the ground conductor 1414 to physically and/or electrically isolate them from one another. For example, the dielectric separator 1440 may include a strip of dielectric material (e.g., a Teflon strip) about the size of (or larger than) the feed line 1430 that is disposed between the feed line 1430 and the overlapped portion of the ground ring 1422 to maintain physical and/or electrical isolation of the signal conductor 1410 (e.g., including the dual helical T-resonator 1418) and the ground conductor 1414. The dielectric separator 1440 may be of a constant thickness (e.g., about 1 mm) to maintain a constant distance between the overlapping portions of the signal conductor 1410 (e.g., including the helical T-resonator 1418) and the ground conductor 1414.

The signal conductor 1410 may include a first/input port 1450 for input of a source signal of a first frequency and phase, and a second/output port 1452 for output of a corresponding response signal of a second frequency and phase. The first/input port 1450 may be located at or near a first end of the feed line 1430, and the second/output port 1452 may be located at or near a second end of the feed line 1430 that is opposite the first end. Electrical leads of the measurement processing system 1406 may be coupled to the ports 1450 and 1452 for introducing source signals and sensing response signals. For example, an input lead for introducing a source signal may extend from an output circuit of the measurement processing system 1406 to the first/input port 1450, and an output lead for sensing the response signal may extend from an input circuit of the measurement processing system 1406 to the second/output port 1452. As described herein, the measurement processing system 1406 may provide and sense the respective signals and use the characteristics of the signals to determine a water-cut of the fluid 1408 in the pipe 1204.

During use, the fluid 1408 (e.g., a production fluid including a mixture of oil and water) may flow through the center of the pipe 1404 such that the fluid 1408 passes between at least a portion of the signal conductor 1410 disposed on the surface 1412 of the pipe 1404 and at least a portion of the ground conductor 1414 disposed on the surface 1412 of the pipe 1404. For example, if the WC sensor 1402 is disposed on a length (or section) of the pipe 1404 used to transport production fluid including a mixture of oil and water) from a well, the production fluid may flow through the pipe 1404, between the signal conductor 1410 and the ground conductor 1414. A source signal can be introduced into the signal conductor 1410 while the fluid 1408 is flowing through the pipe 1404 (or otherwise present in the pipe 1404), and a corresponding response signal present at signal conductor 1410 can be sensed. For example, a source signal of a first/predetermined frequency and phase can be introduced at the first/input port 1450, and a corresponding response signal of a second/resulting frequency and phase can be sensed at the second/output port 1452. As described herein, in some embodiments, the source signal is generated by the measurement processing system 1406. For example, the measurement processing system 1406 may include a vector network analyzer (VNA), and the source signal may be generated by a source circuit, such as a signal generator, of the vector network analyzer (VNA). As describe herein, in some embodiments, the response signal is sensed/measured by the measurement processing system 1406. For example, a sensing circuit, such as a receiver of the vector network analyzer (VNA), may receive the response signal. In some embodiments, the signals are processed by the measurement processing system 1406 to determine various characteristics of the fluid 1408, such as the water-cut of the fluid 1408. For example, the measurement processing system 1406 may include a processor, such as a computer processor of the vector network analyzer (VNA) and/or other computing devices, that analyzes the characteristics of the source signal and/or the corresponding response signal to determine the resonant frequency of the WC sensor 1402 in the presence of the fluid 1408 (e.g., a resonant frequency of the helical T-resonator 1418 with the fluid 1408 currently flowing through or otherwise located in the pipe 1404, between the signal conductor 1410 and the ground conductor 1414). Based on a predetermined correlation between the water-cut of a fluid mixture flowing through the pipe 1404 and the resonant frequency of the WC sensor 1402, the water-cut of the fluid 1408 flowing through the pipe 1404 can be determined. That is, the water-cut of the fluid 1408 passing through the pipe 1408 can be determined based on the resonant frequency of the WC sensor 1402 at or near the time when the fluid 1408 passes through the WC sensor 1402.

Figure 15A:
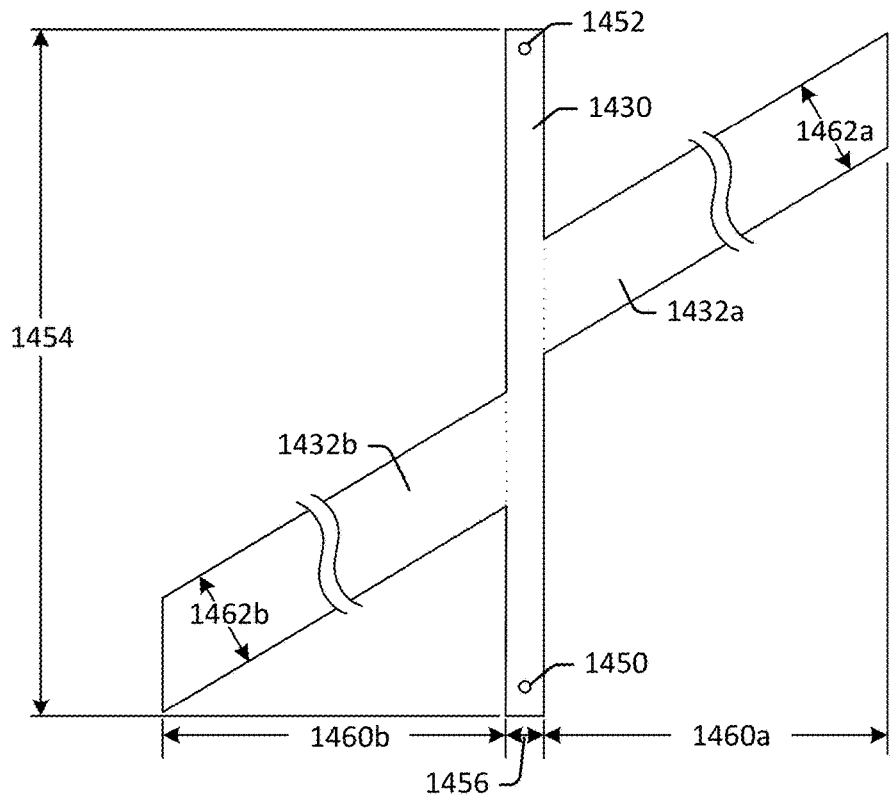
FIG. 15A is a diagram that illustrates a planar view of the dual helical T-resonator of FIGS. 14A-14E in accordance with one or more embodiments.
Figure 15B:
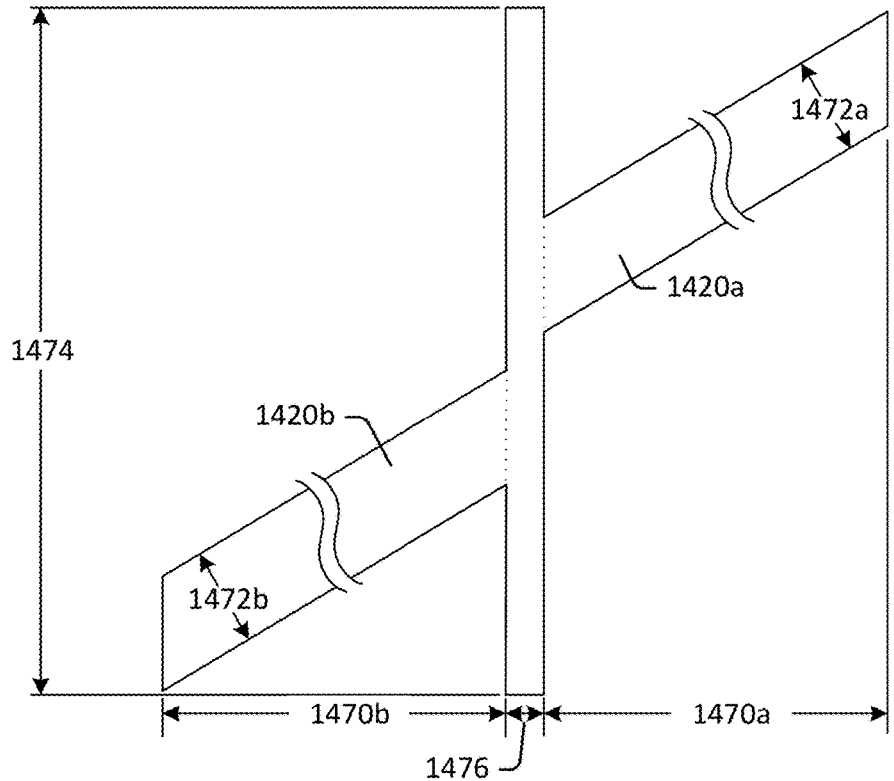
FIG. 15B is a diagram that illustrates a planar view of the dual helical ground conductor of FIGS. 14A-14E in accordance with one or more embodiments.

FIG. 15A is a diagram that illustrates a planar view of the "dual helical" T-resonator 1418 in accordance with one or more embodiments. This view may represent the planar shape of the T-resonator 1418 if it was laid flat (or "unwrapped"), as opposed to being disposed on the curved surface of the pipe 1404. FIG. 15B is a diagram that illustrates a planar view of the dual helical ground conductor 1414 in accordance with one or more embodiments. This view may represent the planar shape of the helical ground conductor 1414 if it was laid flat (or "unwrapped"), as opposed to being disposed on the curved surface of the pipe 1404, and the ground ring 1422 was "broken" as opposed to being contiguously wrapped about the pipe 1404.

In an example embodiment, the pipe 1404 may have an internal diameter of about 46 mm and an outer diameter of about 50 mm. Consistent with the dimensioning discussed above, and referring to FIG. 15A, the feed line 1430 may have a length (or arc length) 1454 of about 68 mm and a width 1456 of about 2.5 mm, the first helical open shunt stub 1432a may have a length 1460a of about 250 mm and a width 1462a of about 25.4 mm, and the second helical open shunt stub 1432b may have a length 1460b of about 250 mm and a width 1462b of about 25.4 mm. Thus, when wrapped about the pipe 1404, each of the first helical open shunt stub 1432a and the second helical open shunt stub 1432b may extend a distance of about 250 mm along the length of the pipe 1404, as illustrated by distances 1460a and 1460b of FIG. 14B. With reference to FIG. 15B, the first helical ground plane 1420a may have a length 1270a that is the same or similar to that of the length of the first helical open shunt stub 1432a (e.g., a length 1470a of about 250 mm) and a width 1472a that is the same or similar to that of the width of the first helical open shunt stub 1432a (e.g., a width 1472a of about 22 mm), the second helical ground plane 1420b may have a length 1470b that is the same or similar to that of the length of the second helical open shunt stub 1432b (e.g., a length 1470b of about 250 mm) and a width 1472b that is the same or similar to that of the width 1462b of the second helical open shunt stub 1432b (e.g., a width 1472b of about 22 mm), and the ground ring 1422 may have a length (or arc length) 1474 of about 157 mm (e.g., the circumference of the pipe 1404) and a width 1476 of about 6.3 mm. The separator 1440 may have a length (or arc length) of about 45 mm and a width of about 6.3 mm.

Figure 16:
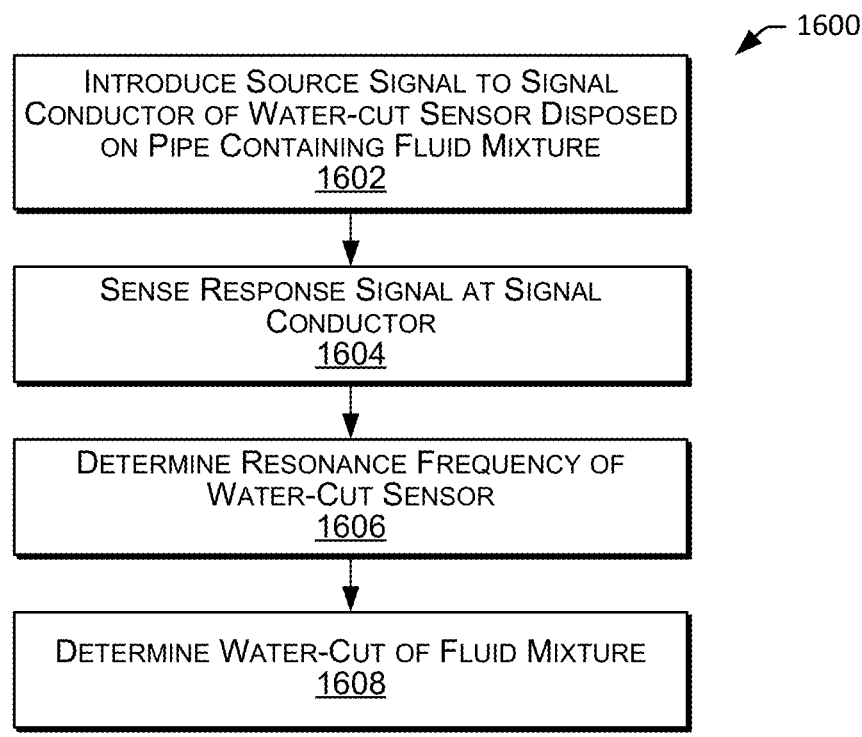
FIG. 16 is a flowchart that illustrates an example method of determining water-cut of a water-oil fluid mixture in a pipe using a microwave based water-cut sensor in accordance with one or more embodiments.

FIG. 16 is a flowchart that illustrates a method 1600 of determining water-cut of a water-oil fluid mixture in a pipe using a microwave based water-cut sensor in accordance with one or more embodiments. Method 1600 may generally include introducing a source signal at a signal conductor of a water-cut sensor disposed on a pipe having a fluid mixture therein (block 1602), sensing a response signal at the signal conductor (block 1604), determining a resonant frequency of the WC sensor based on the response signal (block 1606), and determining a water-cut for the fluid mixture based on the resonant frequency (block 1608). In some embodiments, some or all of the operations of the method 1600 are performed by the measurement processing system 106,1106 or 1206 or 1406 using the WC sensor 102, 1102, 1202 or 1402, respectively.

In some embodiments, introducing a source signal at a signal conductor of a water-cut sensor disposed on a pipe having a fluid mixture therein (block 1602) can include the measurement processing system (e.g., the measurement processing system 106,1106 or 1206 or 1406) driving a signal conductor of a water-cut sensor disposed on a pipe having a fluid therein with one or more source signals of different phase and/or frequencies. For example, the measurement processing system 106 may drive the signal conductor 110 of the WC sensor 102 disposed on the pipe 104, the measurement processing system 1106 may drive the signal conductor 1110 of the straight WC sensor 1102 disposed on the pipe 1104, the measurement processing system 1206 may drive the signal conductor 1210 of the helical WC sensor 1202 disposed on the pipe 1204, or the measurement processing system 1406 may drive the first signal conductor 1410a and the second signal conductor 1410b of the double-helical WC sensor 1402 disposed on the pipe 1404. The source signals may be for example in the operational range of the respective WC sensor (e.g., in the range of about 50 MHz to about 130 Mhz).

In some embodiments, sensing a response signal at the signal conductor (block 1604), can include the measurement processing system (e.g., measurement processing system 1106, 1206 or 1406) sensing the phase and/or frequency of one or more response signals at another portion of the signal conductor (e.g., signal conductor 1110, 1210, 1410a or 1410b) that are generated as a result of the introduction of the one or more source signals.

Figure 19:
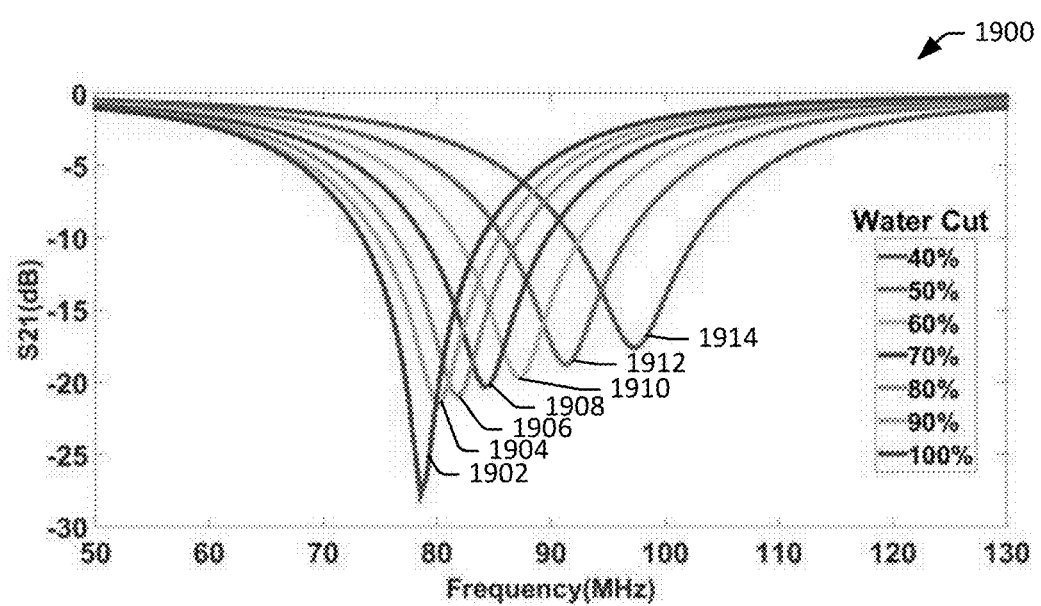
FIG. 19 is a plot diagram that illustrates example S21 responses of a water-cut sensor determined for fluids in a pipe in accordance with one or more embodiments.
Figure 20A:
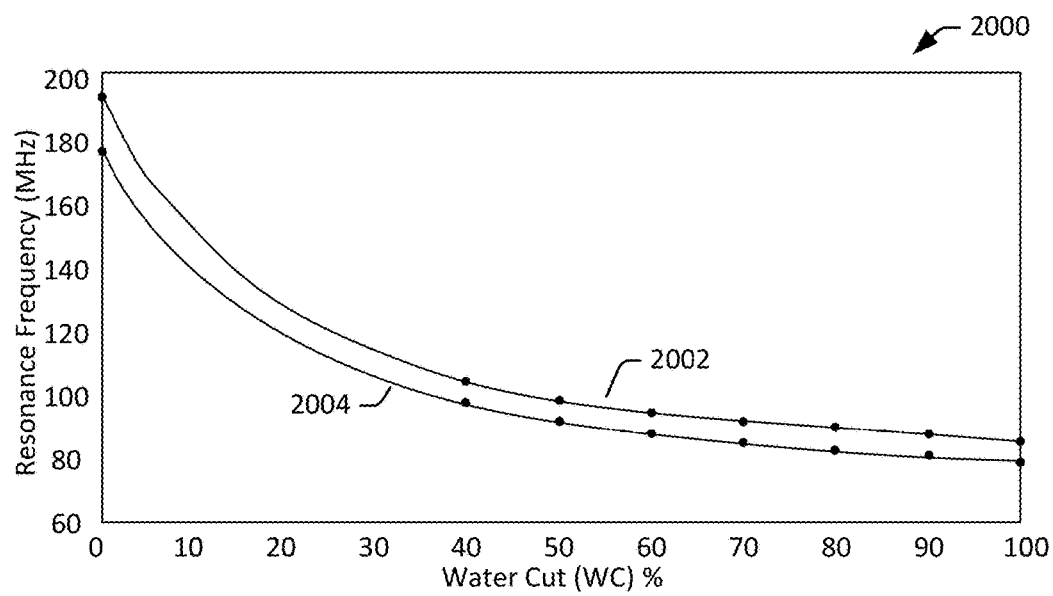
FIG. 20A is a plot diagram that illustrates an example comparison of simulated vs. measured characteristic curves of a water-cut sensor with homogeneously mixed oil and water in accordance with one or more embodiments.
Figure 20B:
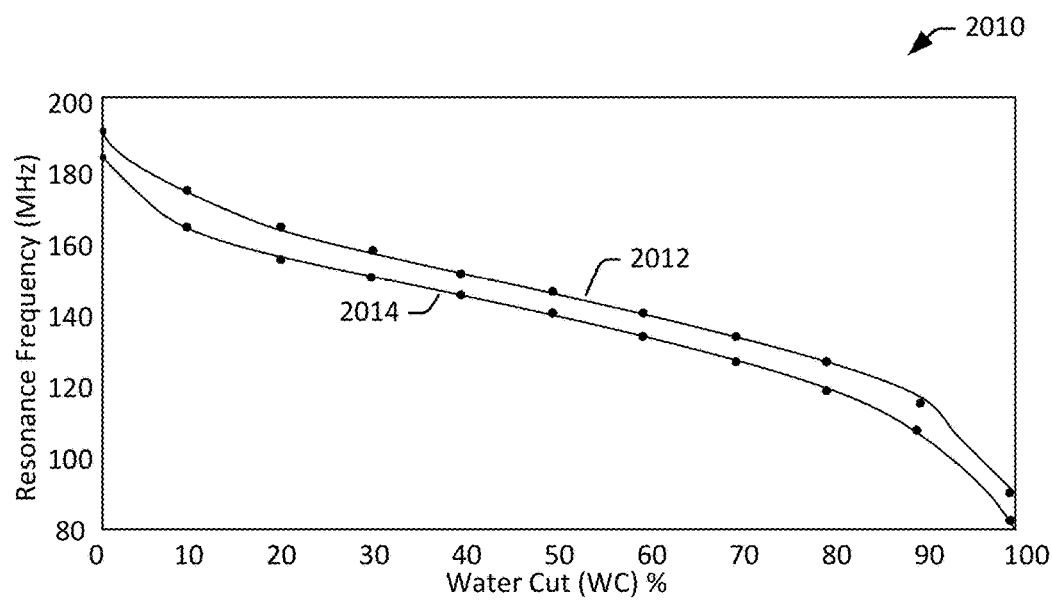
FIG. 20B is a plot diagram that illustrates an example comparison of simulated vs measured characteristic curves of a water-cut sensor with separate oil and water phases in accordance with one or more embodiments.
Figure 21A:
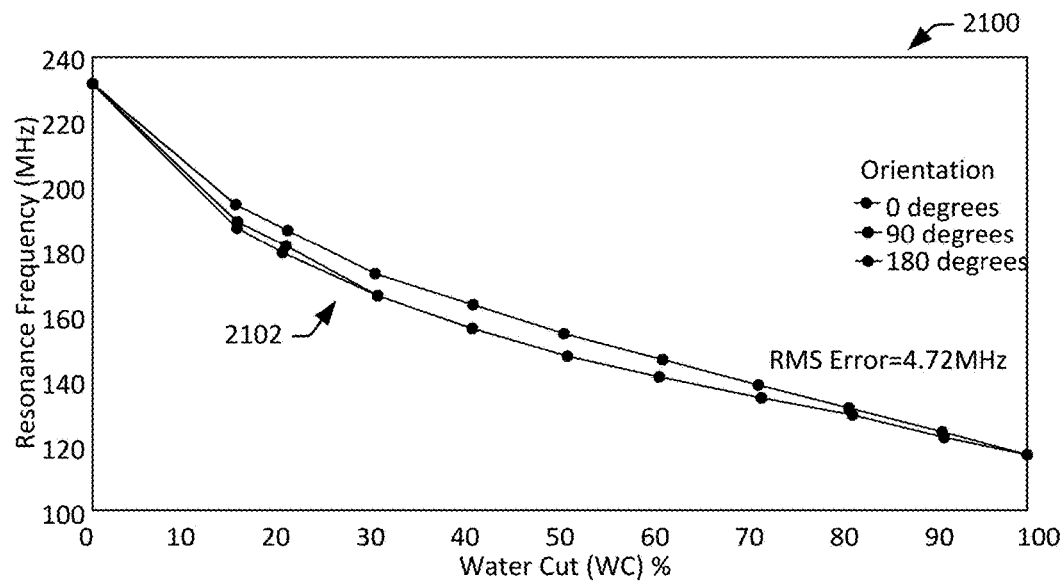
FIG. 21A is a plot diagram that illustrates example water-cut characteristic curves of water-cut for fluids having different orientations of mixed oil and water obtained using a helical water-cut sensor in accordance with one or more embodiments.
Figure 21B:
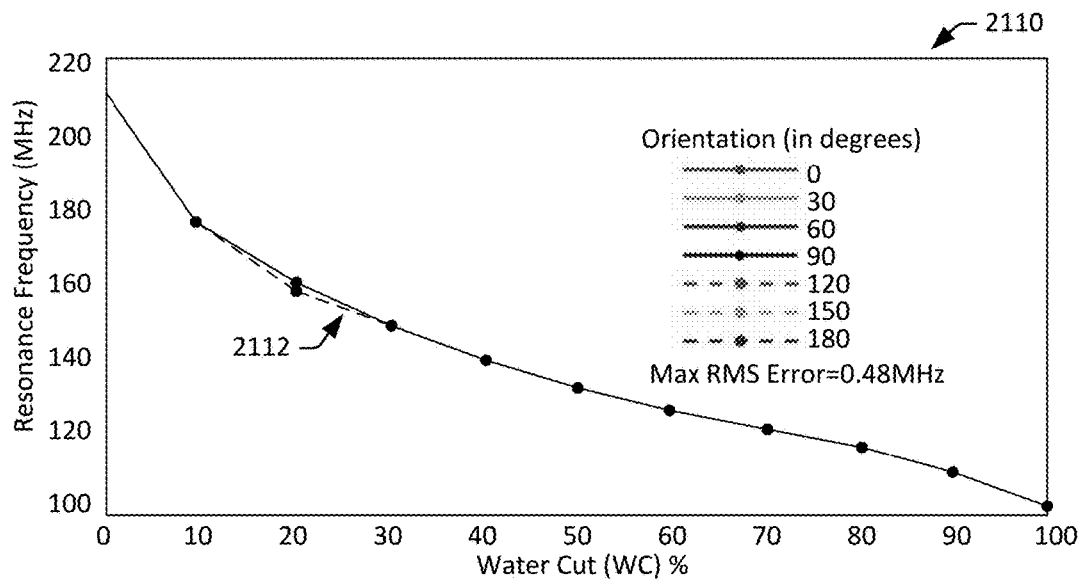
FIG. 21B is a plot diagram that illustrates example water-cut characteristic curves of water-cut for fluids having different orientations of mixed oil and water obtained using a dual helical water-cut sensor in accordance with one or more embodiments.

In some embodiments, as described below, introducing the source signal at a signal conductor of a water-cut sensor disposed on a pipe having a fluid therein (block 1602) and/or sensing a response signal at the signal conductor (block 1604) may be conducted in a frequency sweep. For example, referring to the WC sensor 1102 of FIG. 10E as an example, a vector network analyzer (VNA) of the measurement processing system 1106 may conduct a frequency sweep, supplying source signals having different frequencies in the range of about 50 MHz-130 Mhz to the input terminal 1150 of the feed line 1130 of the signal conductor 1110 of the water-cut sensor 1102 disposed on a pipe 1104 and having the fluid 1108 therein. During the frequency sweep, the vector network analyzer (VNA) may measure the phase and frequency of corresponding response signals present at the output terminal 1152. The vector network analyzer (VNA) may assess these signals to determine a S21 response value for each of the frequencies. That is, a S21 response across the frequency range can be determined. FIG. 19 is a plot 1900 that illustrates example S21 responses of a water-cut sensor 1102 determined for fluids 1108 having a water-cut of about 100% to about 40% in accordance with one or more embodiments. For example, the first curve 1902, second curve 1904, third curve 1906, fourth curve 1908, fifth curve 1910, sixth curve 1912, and seventh curve 1914, represent example S21 responses determined for the water-cut sensor 102 with fluids having known water-cuts of 100%, 90%, 80%, 70%, 60%, 50% and 40%, respectively, present in the pipe 1104. The reliability of this technique has been verified through simulation and actual test results for fluids having known WC values. FIG. 20A is a plot 2000 that illustrates an example comparison of simulated vs measured characteristic curves of a WC of a fluid having homogeneously mixed oil and water in accordance with one or more embodiments. The top curve 2002 represent the characteristic curve based on actual measurements, and the bottom curve 2004 represents the characteristic curve based on simulated measurements. FIG. 20B is a plot 2010 that illustrates an example comparison of simulated vs measured characteristic curves of a WC of a fluid having separate oil and water phases in accordance with one or more embodiments. The top curve 2012 represent the characteristic curve based on actual measurements, and the bottom curve 2014 represents the characteristic curve based on simulated measurements. A sweep operation, similar to that described above for the WC sensor system 1000, can be conducted for the other embodiments of WC sensors, including those of the WC sensor system 100, 1200 and/or 1400. FIG. 21A is a plot 2100 that illustrates example WC characteristic curves of WC for fluids having different orientations of mixed oil and water obtained using a single helical WC sensor in accordance with one or more embodiments. The curves 2102 correspond to fluid mixtures having respective oil/water mixture orientations of 0, 90, and 180 degrees. FIG. 21B is a plot 2110 that illustrates example WC characteristic curves of WC for fluids having different orientations of mixed oil and water obtained using a dual helical WC sensor in accordance with one or more embodiments. The curves 2112 corresponds to fluid mixtures having respective oil/water mixture orientations of 0, 30, 60, 90, 120, 150 and 180 degrees.

In some embodiments, determining a resonant frequency of the signal conductor based on the response signal (block 1606) can include the measurement processing system (e.g., measurement processing system 106, 1106, 1206 or 1406) determining a resonant frequency of the water-cut sensor with the fluid present in the pipe (e.g., with the fluid 108, 1108, 1208 or 1408 present in the pipe 104, 1104, 1204 or 1404, respectively) when the source signal was introduced and/or the corresponding response signals were sensed. Referring, for example, to the WC system 1000 and FIG. 19 as an example, the resonant frequency may be identified as a well-defined dip the an S21 response across the relevant frequencies. Continuing with the above example, if a frequency sweep is conducted while a fluid 1108 having a WC of about 50% is flowing through the pipe 1104, the resulting S21 response curve may look similar to that of the sixth curve 1912, and the resonant frequency can be determined to about 91 MHz based on the well-defined dip in the S21 response (e.g., the frequency at about the lowest point on the S21 response curve 1912).

In some embodiments, determining a water-cut for the fluid mixture based on the determined resonant frequency (block 1608) can include the measurement processing system (e.g., measurement processing system 106, 1106, 1206 or 1406) determining a WC that corresponds to the determined resonant frequency for the WC sensor (e.g., for the WC sensor 102, 1102, 1202 or 1402, respectively). For example, calibration test can be run with the a WC sensor (e.g., the WC sensor 102, 1102, 1202 or 1402) (or a test WC sensor) in the same or similar conditions (e.g., on the pipe 104, 1104, 1204 or 1404, respectively, or a similar type/sized pipe) with fluids having different water-cuts to generate a mapping (e.g., an equation, curve, look-up table or the like) that represents water-cuts vs. observed resonant frequency. In response to determining the resonant frequency, the measurement processing system (e.g., measurement processing system 106, 1106, 1206 or 1406) may employ this predefined relationship to determine the WC for the fluid (e.g., the fluid 108, 1108, 1208 or 1408, respectively). For example, the measurement processing system 1106 may access a look-up-table to determine that fluid flowing through the pipe 1104 having an S21 response at about 91 MHz, has a water-cut of 50%. That is, if a frequency sweep indicates that the WC sensor 1102 has a dip (low point) in the S21 response at about 91 MHz, then it can be determined that the fluid 1108 in the pipe has a WC of about 50%.

In some embodiments, the above process can be performed continuously (e.g., in series, one after the other), on a regular basis (e.g., every minute, hourly, and/or the like), or the like so that the WC for a fluid flowing through the pipe can be continually or regularly determined. For example, the measurement processing system (e.g., (e.g., measurement processing system 106, 1106, 1206 or 1406) may initiate and conduct the operations of method 1600 continuously (e.g., in series, one after the other), on a regular basis (e.g., every minute, hourly, and/or the like), or the like, and the results may be presented (e.g., displayed to a well/production operator), stored in a memory (e.g., a WC log) for later review, and/or used for other related determinations.

In some embodiments, to manufacture a WC sensor for use in making WC measurements for fluid flowing through a pipe, some or all of the elements of a WC sensor can be formed directly onto the surface of the pipe. For example, one or more masks can be disposed about the surface of the pipe that provides one or more openings for the one or more ground plane, the ground ring, the one or more open shunt stubs, and/or the feed line. A conductive paste can be disposed (e.g., sprayed, painted, and/or the like) into the opening(s) of the mask to form the one or more ground planes, the ground ring, the one or more open shunt stubs, and/or the feed line. Once the conductive paste has cured, the corresponding mask portion can be removed, leaving a conductive pattern that includes the signal conductor and the ground conductor, formed from the cured conductive paste, disposed on the surface of the pipe.

Figure 17A:
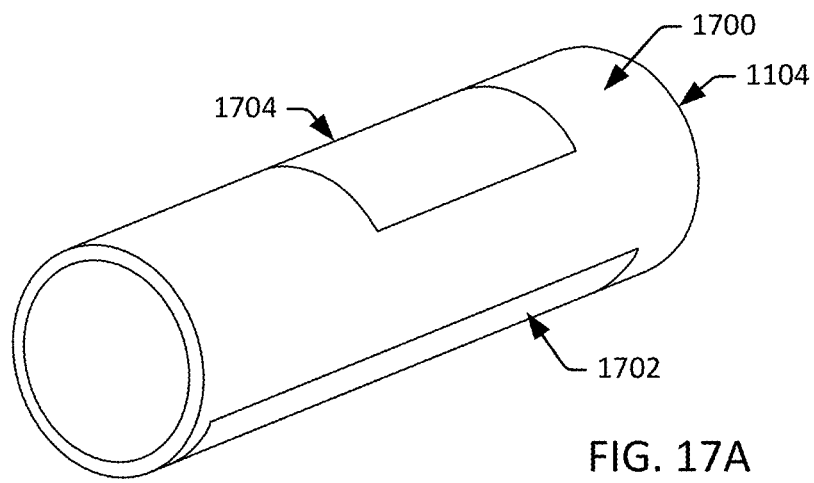
FIGS. 17A-17F are diagrams that illustrate examples of various masks that can be employed in the manufacture of a water-cut sensor in accordance with one or more embodiments.
Figure 17B:
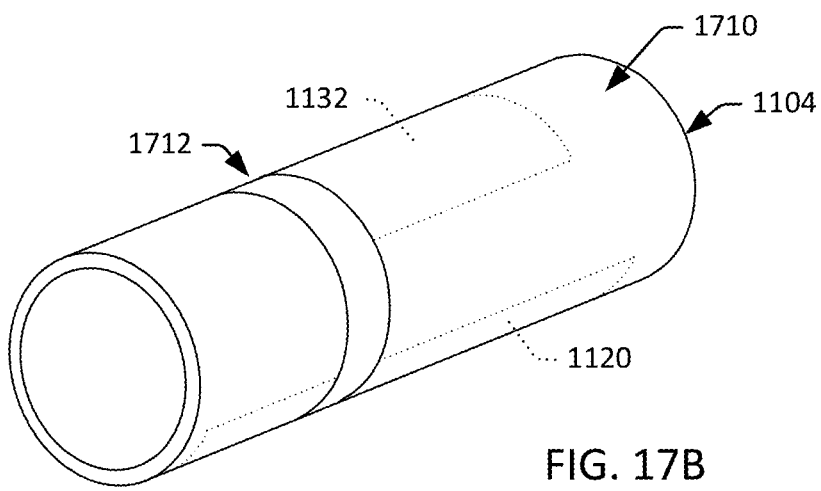
Figure 17C:
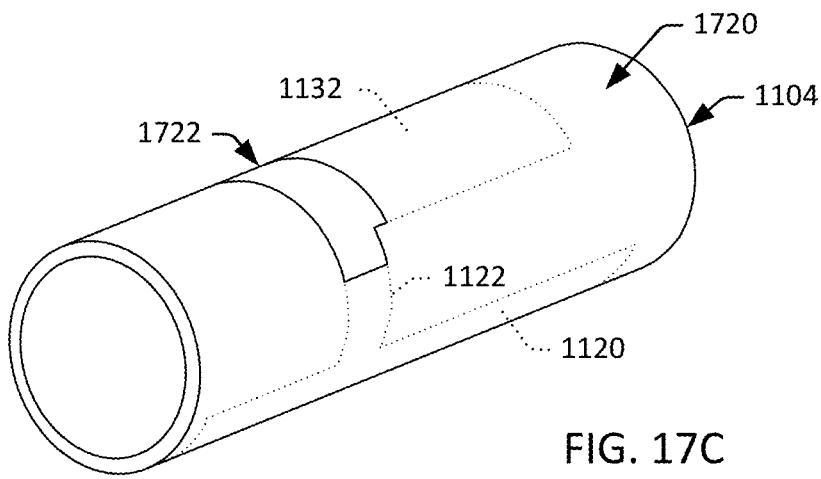
Figure 17D:
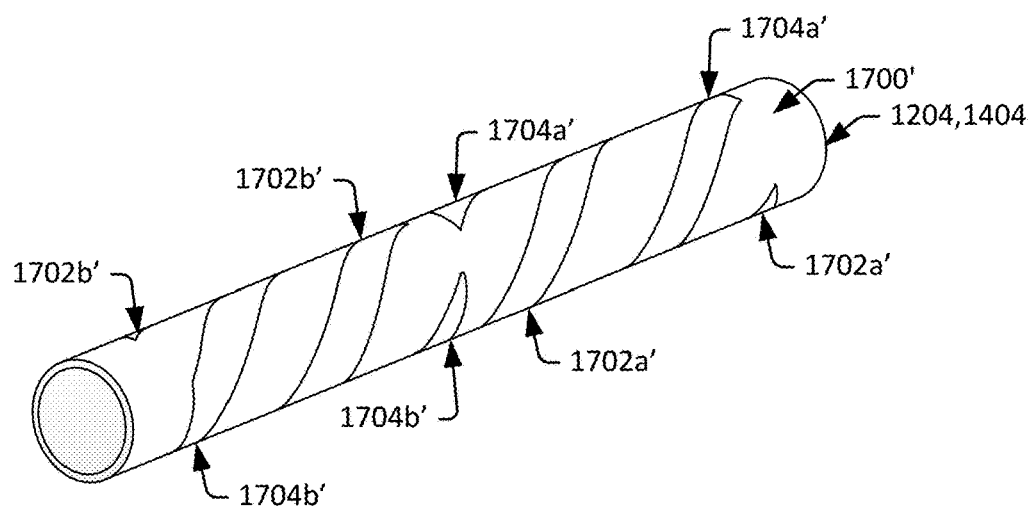

FIGS. 17A-17F are diagrams illustrating various masks that can be employed in the manufacture a WC sensor in accordance with one or more embodiments. The masks can include three-dimensional (3D) masks, printed or otherwise disposed on the surface of pipe and/or other materials already deposited on the pipe. FIG. 17A illustrates an example first mask 1700 in accordance with one or more embodiments. The first mask 1700 may include material covering some or all of the portions of the pipe 1104, other than in areas where openings in the first mask 1700 expose the surface of the pipe 1104 on which the ground plane 1120 and the open shut stub 1132 (or at least a portion thereof) is to be disposed. That is, the first mask 1700 may provide a first opening 1702 for the ground plane 1120 and a second opening 1704 for at least a distal portion of the open shut stub 1132 (e.g., the portion distal from the ground ring 1122). With regard to embodiments of the single helical WC sensor 1202, a first mask 1700 can be provided on the pipe 1204 that includes material covering some or all of the portions of the pipe 1204, other than in areas where openings in the first mask 1700 expose the surface of the pipe 1204 on which the ground plane 1220 and the open shut stub 1212 (or at least a portion thereof) is to be disposed. With regard to the single helical WC sensor 1202, the first mask 1700 may provide a first opening for the ground plane 1220 and a second opening for at least a distal portion of the helical open shut stub 1232 (e.g., the portion distal from the ground ring 1222). For example, FIG. 17D illustrates an embodiment of a first mask 1700' that includes an opening 1702a' for forming the ground plane 1220 and an opening 1704a' for forming at least a distal portion of the helical open shut stub 1232 (e.g., the portion distal from the ground ring 1222). With regard to embodiments of the double helical WC sensor 1402, a first mask 1700 can be provided on the pipe 1404 that includes material covering some or all of the portions of the pipe 1404, other than in areas where openings in the first mask 1700 expose the surface of the pipe 1404 on which the ground plane 1420 and the helical open shut stubs 1432a and 1432b (or at least a portion thereof) are to be disposed. With regard to the double helical WC sensor 1402, the first mask 1700 may provide a first opening for the first ground plane 1420a, a second opening for at least a distal portion of the first helical open shut stub 1432a, a third opening for the second ground plane 1420b, and a fourth opening for at least a distal portion of the second helical open shut stub 1432b (e.g., for the portions of the open shut stub distal from the ground ring 1422). For example, referring again to FIG. 17D, the first mask 1700' may include the opening 1702a' for forming the first ground plane 1420a, the opening 1704a' for forming at least a distal portion of the first helical open shut stub 1432a, an opening 1702b' for forming the second ground plane 1420b, and an opening 1704b' for forming at least a distal portion of the second helical open shut stub 1432b (e.g., for the portions of the open shut stub distal from the ground ring 1422).

Figure 17E:
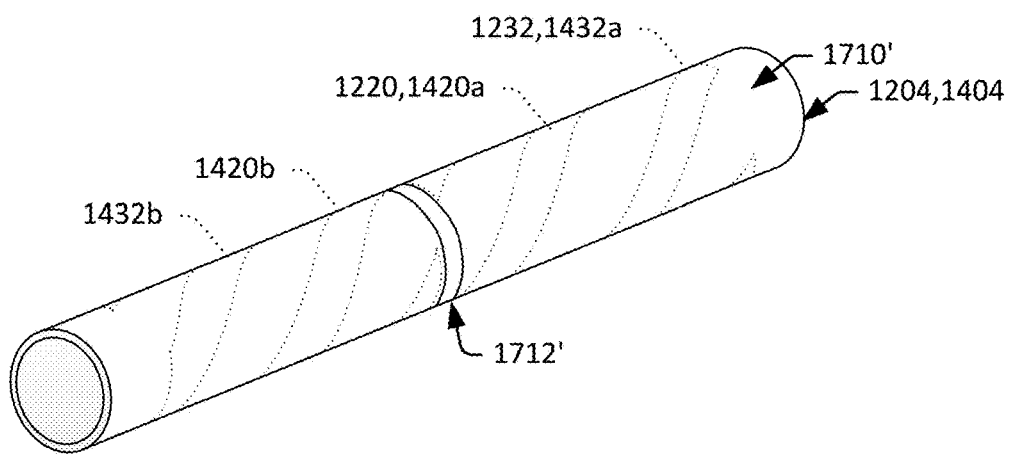

FIG. 17B illustrates an example second mask 1710 in accordance with one or more embodiments. The second mask 1710 may include material covering some or all of the portions of the pipe 1104, other than in areas where opening(s) in the second mask 1710 expose the surface of the pipe 1104 and/or the ground plane 1120 on which the ground ring 1122 is to be disposed or at least attached. That is, the second mask 1710 may provide a third opening 1712 for the ground ring 1122. In some embodiments, the first mask 1700 may include the openings 1704, 1702 and 1712 such that the ground plane 1120, the open shunt stub 1132 and the ground ring 1122 can be formed at the same time (or at least using the single first mask 1700). In some embodiments, the dielectric separator 1140 may be disposed on the ground ring 1122. With regard to embodiments of the single helical WC sensor 1202, the second mask 1710 may include material covering some or all of the portions of the pipe 1204, other than in areas where opening(s) in the second mask 1710 expose the surface of the pipe 1204 and/or the ground plane 1220 on which the ground ring 1222 is to be disposed or at least attached. That is, the second mask 1710 may provide an opening 1712 for the ground ring 1222. For example, FIG. 17E illustrates an embodiment of the second mask 1710' that includes an opening 1712' for forming the ground ring 1222. In some embodiments, the first mask 1700 may include openings such that the ground plane 1220, the helical open shunt stub 1232, and the ground ring 1222 can be formed at the same time (or at least using the single mask 1700). In some embodiments, the dielectric separator 1240 may be disposed on the ground ring 1222. With regard to embodiments of the double helical WC sensor 1402, the second mask 1710 may include material covering some or all of the portions of the pipe 1404, other than in areas where opening(s) in the second mask 1710 expose the surface of the pipe 1404 and/or the ground plane 1420 on which the ground ring 1422 is to be disposed or at least attached. That is, the second mask 1710 may provide an opening 1712 for the ground ring 1422. For example, referring again to FIG. 17E, the second mask 1710' may include the opening 1712' for forming the ground ring 1222. In some embodiments, the first mask 1700 may include openings such that the ground plane 1420, the helical open shunt stubs 1432a and 1432b, and the ground ring 1422 can be formed at the same time (or at least using the single mask 1700). In some embodiments, the dielectric separator 1440 may be disposed on the ground ring 1422.

Figure 17F:
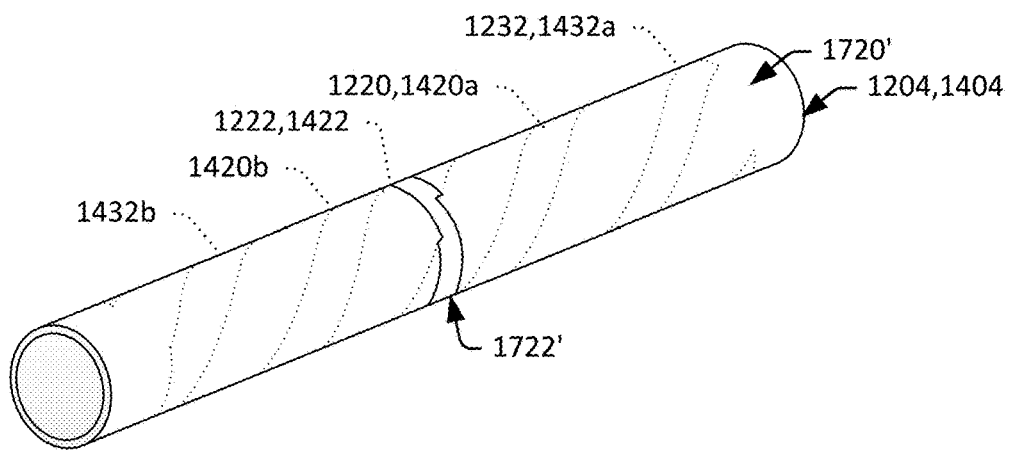

FIG. 17C illustrates an example third mask 1720 in accordance with one or more embodiments. The third mask 1720 may include material covering some or all of the portions of the pipe 1104, other than in areas where opening(s) in the third mask 1720 expose the surface of the pipe 1104, the ground ring 1122 and/or the dielectric separator 1140 on which on which the feed line 1130 and/or the proximal portion of the open shunt stub 1132 is to be disposed. That is, the third mask 1720 may provide an opening 1722 for the feed line 1130 and/or the proximal portion of the open shunt stub 1132. With regard to embodiments of the single helical WC sensor 1202, the third mask 1720 may include material covering some or all of the portions of the pipe 1204, other than in areas where opening(s) in the third mask 1720 expose the surface of the pipe 1204, the ground ring 1222 and/or the dielectric separator 1240 on which on which the feed line 1230 and/or the proximal portion of the open shunt stub 1232 is to be disposed, respectively. That is, the third mask 1720 may provide an opening 1722 for the feed line 1230 and/or the proximal portion of the open shunt stub 1232. For example, FIG. 17F illustrates an embodiment of the third mask 1720' that includes an opening 1722' for forming for the feed line 1230 and/or the proximal portion of the open shunt stub 1232. With regard to embodiments of the double helical WC sensor 1402, the third mask 1720 may include material covering some or all of the portions of the pipe 1404, other than in areas where opening(s) in the third mask 1720 expose the surface of the pipe 1404, the ground ring 1422 and/or the dielectric separator 1440 on which on which the feed line 1430 and/or the proximal portion of the open shunt stubs 1432a and 1432b are to be disposed, respectively. That is, the third mask 1720 may provide an opening 1722 for the feed line 1430 and/or the proximal portions of the open shunt stubs 1432a and 1432b. For example, referring again to FIG. 17F, the third mask 1720' may include an opening 1722' for forming for the feed line 1230 and/or the proximal portion of the open shunt stubs 1432a and 1432b.

Figure 18:
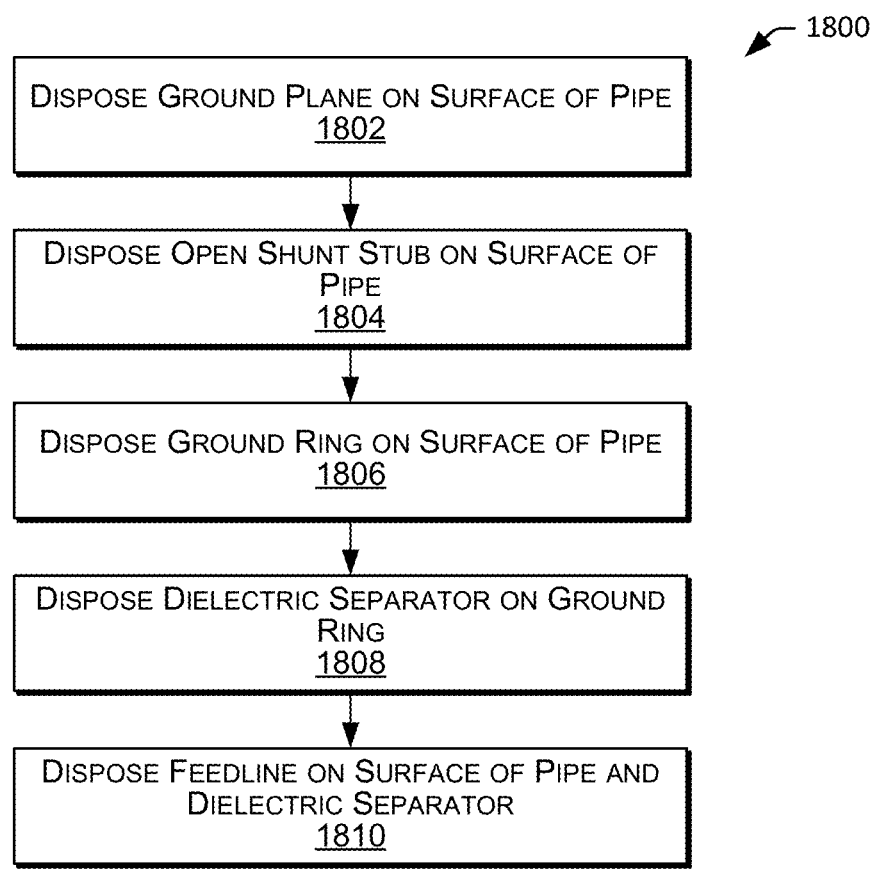
FIG. 18 is a flowchart that illustrates an example method of manufacturing a microwave based water-cut sensor for a pipe in accordance with one or more embodiments.

FIG. 18 is a flowchart that illustrates a method 1800 of manufacturing a microwave based water-cut sensor for a pipe in accordance with one or more embodiments. Method 1400 may generally include disposing the ground plane on the surface of the pipe (block 1802), disposing the open shunt stub(s) on the surface of the pipe (block 1804), disposing the ground ring on the surface of the pipe (block 1806), disposing the dielectric separator on ground ring (block 1808), and disposing the feed line on the surface of the pipe (block 1810).

In some embodiments, disposing the ground plane on the surface of the pipe (block 1802) and disposing the open shunt stub(s) on the surface of the pipe (block 1804) can include disposing the first mask 1700 on the surface of the pipe 1104, and disposing (e.g., spraying, painting, and/or the like) a conductive material (e.g., a copper based paste) into the first opening 1702 (e.g., to form the ground plane 1120 and into the second opening 1704 (e.g., to form at least a distal portion of the open shut stub 1132 distal from the ground ring 1122). With regard to embodiments of the single helical WC sensor 1202, this can include disposing the first mask 1700' on the surface of the pipe 1204, and disposing (e.g., spraying, painting, and/or the like) a conductive material (e.g., a copper based paste) into the opening 1702a' (e.g., to form the ground plane 1220) and the second opening 1704a' (e.g., to form at least a distal portion of the open shut stub 1232 distal from the ground ring 1222). With regard to embodiments of the double helical WC sensor 1402, this can include disposing the first mask 1700' on the surface of the pipe 1404, and disposing (e.g., spraying, painting, and/or the like) a conductive material (e.g., a copper based paste) into the openings 1702a' and 102b' (e.g., to form the ground planes 1420a and 1420b) and the second openings 1704a' and 1704b' (e.g., to form at least a distal portion of the open shut stubs 1432a and 1432b distal from the ground ring 1422). The first mask 1700 or 1700' may be removed, for example, once the conductive paste has cured.

In some embodiments, disposing the ground ring on the surface of the pipe (block 1806) can include disposing the second mask 1710 on the surface of the pipe 1104, and disposing (e.g., spraying, painting, and/or the like) a conductive material (e.g., a copper based paste) into the third opening 1712 (e.g., to form the ground ring 1122). The conductive material may be disposed on the exposed surface of the pipe and/or over the ground plane (e.g., over the ground plane 1120). With regard to embodiments of the single helical WC sensor 1202 or the double helical WC sensors 1402, this can include disposing the second mask 1710' on the surface of the pipe 1204 or 1404, and disposing (e.g., spraying, painting, and/or the like) a conductive material (e.g., a copper based paste) into the opening 1712' (e.g., to form the ground ring 1222 or 1422). The conductive material may be disposed on the exposed surface of the pipe and/or over the ground plane (e.g., over the ground plane 1220, or the ground planes 1420a and 1420b). The second mask 1710 or 1710' may be removed, for example, once the conductive paste has cured. In some embodiments, the first mask 1700 may include the openings 1704, 1702 and 1712 such that the ground plane 1120, the open shunt stub 1132 and the ground ring 1122 can be formed at the same time (or at least using the single first mask 1700). In some embodiments, the first mask 1700' may include the openings 1702a', 1702b', 1704a', 1704b' and/or 1712' such that the ground planes 1220 or 1420a and 1420b, the open shunt stubs 1232 or 1432a and 1432b, and the ground ring 1222 or 1422 can be formed at the same time (or at least using the single first mask 1700').

In some embodiments, disposing the dielectric separator on ground ring (block 1808) can include obtaining a dielectric separator (e.g., dielectric separator 1140, 1240 or 1440) (e.g., a strip of dielectric material, such as a piece of Teflon tape) that is about the size of the feed line to be formed (e.g., feed line 1130, 1230 or 1430), and placing the dielectric separator on the exterior surface of the ground ring (e.g., ground ring 1122, 1222 or 1422) that is to be overlapped by the feed line.

In some embodiments, disposing the feed line on the surface of the pipe (block 1810) can include disposing the third mask 1720 on the surface of the 1104 and the dielectric separator 1140, and disposing (e.g., spraying, painting, and/or the like) a conductive material (e.g., a copper based paste) into the fourth opening 1722 (e.g., to form the feed line 1130 and/or the proximal portion of the open shunt stub 1132). With regard to embodiments of the single helical WC sensor 1202 or the double helical WC sensors 1402, this can include disposing the third mask 1720' on the surface of the pipe 1204 or 1404, and disposing (e.g., spraying, painting, and/or the like) a conductive material (e.g., a copper based paste) into the opening 1722' (e.g., to form the feed line 1230 or 1430 and/or the proximal portion of the respective open shunt stubs 1232 or 1432a and 1432b. The third mask 1720 or 1720' may be removed, for example, once the conductive paste has cured. In some embodiments, an input and/or and output port may be provided. For example, a terminal (e.g., an SubMiniature version A (SMA) connector) for the respective input port (e.g., input port 1150, 1250 or 1450) may be provided at a first end of the feed line and a terminal (e.g., an SMA connector) for the output port (e.g., output port 1152, 1252 or 1452) may be provided at a second end of the feed line (e.g., opposite the first end of the feed line).

In some embodiments, the measurement processing system 106, 1106, 1206 and/or 1406 includes a computer system for performing some or all of the operations described with regard to the respective measurement processing system). For example, the measurement processing system 106, 1106, 1206 or 1406 may include a computer for automatically controlling an external device (e.g., vector network analyzer (VNA) of the measurement processing system 106, 1106, 1206 or 1406 to conduct one or more frequency sweeps across the respective WC sensor 102, 1102, 1202 or 1402 on the respective pipe 104, 1104, 1204 or 1404, and to process the corresponding signals to determine respective WC measurements for the fluid 108, 1108, 1208 or 1408 flowing through the respective pipe 104, 1104, 1204 or 1404. In some embodiments, the measurement processing system 106, 1106, 1206 and/or 1406 can include a computer system that is the same or similar to the example computer system 3000 described with regard to FIG. 22.

Figure 22:
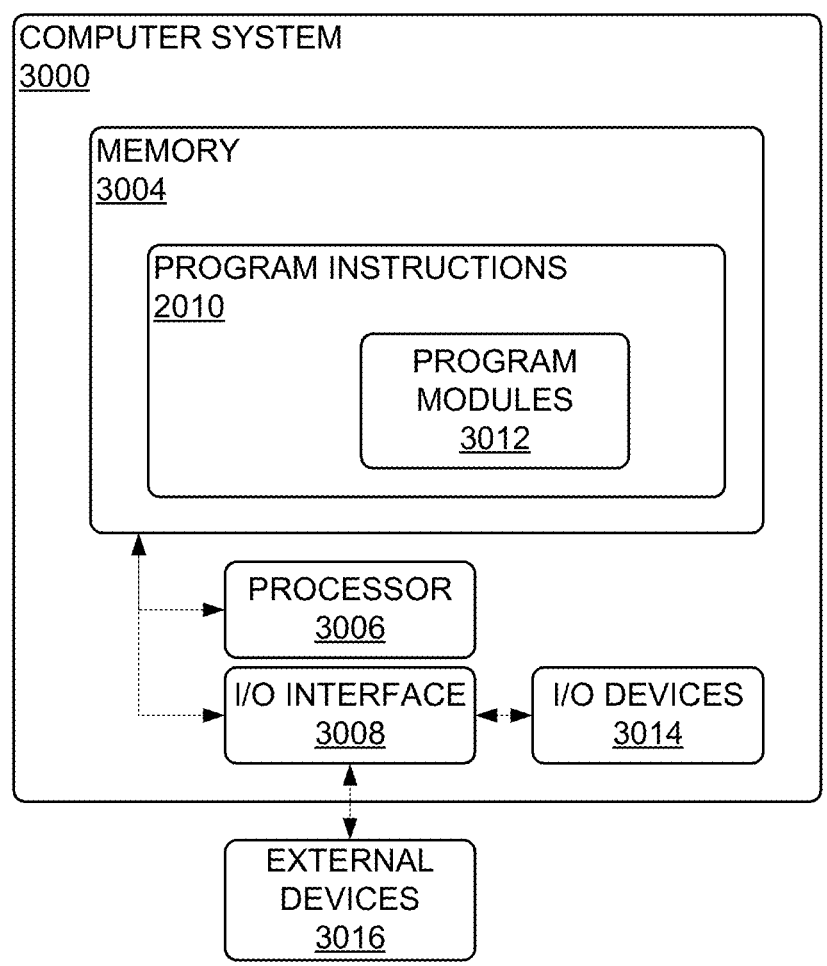
FIG. 22 is a diagram that illustrates an example computer system in accordance with one or more embodiments.

FIG. 22 is a diagram that illustrates an example computer system 3000 in accordance with one or more embodiments. In some embodiments, the computer system 3000 may include a memory 3004, a processor 3006, and an input/output (I/O) interface 3008. The memory 3004 may include non-volatile memory (e.g., flash memory, read-only memory (ROM), programmable read-only memory (PROM), erasable programmable read-only memory (EPROM), electrically erasable programmable read-only memory (EEPROM)), volatile memory (e.g., random access memory (RAM), static random access memory (SRAM), synchronous dynamic RAM (SDRAM)), bulk storage memory (e.g., CD-ROM and/or DVD-ROM, hard drives), and/or the like. The memory 3004 may include a non-transitory computer-readable storage medium having program instructions 3010 stored therein. The program instructions 3010 may include program modules 3012 that are executable by a computer processor (e.g., the processor 3006) to cause the functional operations described herein, including those described with regard to the processes described herein, including the methods 1600 and/or 1800. In the context of a computer system of a measurement processing system 106, 1106, 1206 or 1406, the program modules 3012 may include one or more user modules for performing some or all of the operations described with regard to the measurement processing system 106, 1106, 1206 or 1406.

The processor 3006 may be any suitable processor capable of executing/performing program instructions. The processor 3006 may include a central processing unit (CPU) that carries out program instructions (e.g., the program instructions of the program module(s) 3012) to perform the arithmetical, logical, and input/output operations described herein. The processor 3006 may include one or more processors. The I/O interface 2008 may provide an interface for communication with one or more I/O devices 3014, such as a joystick, a computer mouse, a keyboard, a display screen (e.g., an electronic display for displaying a graphical user interface (GUI)), and/or the like. The I/O devices 3014 may include one or more of the user input devices. The I/O devices 3014 may be connected to the I/O interface 2008 via a wired or a wireless connection. The I/O interface 3008 may provide an interface for communication with one or more external devices 3016, such as other computers, networks, and/or the like. In some embodiments, the I/O interface 3008 may include an antenna, a transceiver, and/or the like. In some embodiments, the computer system 3000 and/or the external devices 3016 may include a vector network analyzer (VNA). Further modifications and alternative embodiments of various aspects of the disclosure will be apparent to those skilled in the art in view of this description. Accordingly, this description is to be construed as illustrative only and is for the purpose of teaching those skilled in the art the general manner of carrying out the embodiments. It is to be understood that the forms of the embodiments shown and described herein are to be taken as examples of embodiments. Elements and materials may be substituted for those illustrated and described herein, parts and processes may be reversed or omitted, and certain features of the embodiments may be utilized independently, all as would be apparent to one skilled in the art after having the benefit of this description of the embodiments. Changes may be made in the elements described herein without departing from the spirit and scope of the embodiments as described in the following claims. Headings used herein are for organizational purposes only and are not meant to be used to limit the scope of the description.

It will be appreciated that the processes and methods described herein are example embodiments of processes and methods that may be employed in accordance with the techniques described herein. The processes and methods may be modified to facilitate variations of their implementation and use. The order of the processes and methods and the operations provided therein may be changed, and various elements may be added, reordered, combined, omitted, modified, etc. Portions of the processes and methods may be implemented in software, hardware, or a combination thereof. Some or all of the portions of the processes and methods may be implemented by one or more of the processors/modules/applications described herein.

As used throughout this application, the word "may" is used in a permissive sense (i.e., meaning having the potential to), rather than the mandatory sense (i.e., meaning must). The words "include," "including," and "includes" mean including, but not limited to. As used throughout this application, the singular forms "a", "an," and "the" include plural referents unless the content clearly indicates otherwise. Thus, for example, reference to "an element" may include a combination of two or more elements. As used throughout this application, the phrase "based on" does not limit the associated operation to being solely based on a particular item. Thus, for example, processing "based on" data A may include processing based at least in part on data A and based at least in part on data B unless the content clearly indicates otherwise. As used throughout this application, the term "from" does not limit the associated operation to being directly from. Thus, for example, receiving an item "from" an entity may include receiving an item directly from the entity or indirectly from the entity (e.g., via an intermediary entity). Unless specifically stated otherwise, as apparent from the discussion, it is appreciated that throughout this specification discussions utilizing terms such as "processing," "computing," "calculating," "determining," or the like refer to actions or processes of a specific apparatus, such as a special purpose computer or a similar special purpose electronic processing/computing device. In the context of this specification, a special purpose computer or a similar special purpose electronic processing/computing device is capable of manipulating or transforming signals, typically represented as physical, electronic or magnetic quantities within memories, registers, or other information storage devices, transmission devices, or display devices of the special purpose computer or similar special purpose electronic processing/computing device.

What is claimed is:

1. A method of manufacturing a water-cut sensor system, the method comprising:
    forming, on an external surface of a cylindrical pipe, a helical T-resonator of a water-cut sensor, comprising:
        disposing, on the external surface of the cylindrical pipe, a feed line comprising a conductive material extending in a circumferential direction about the external surface of the cylindrical pipe; and
        disposing, on the external surface of the cylindrical pipe, a helical open shunt stub comprising a conductive material extending from the feed line in a spiral pattern along the external surface of the cylindrical pipe, the helical open shunt stub being conductively coupled to the feed line;
    forming, on the external surface of the cylindrical pipe, a helical ground conductor of a water-cut sensor, comprising:
        disposing, on the external surface of the cylindrical pipe, a ground ring comprising a conductive material extending in a circumferential direction about the external surface of the cylindrical pipe, the feed line overlapping the ground ring; and
        disposing, on the external surface of the cylindrical pipe, a helical ground plane comprising a conductive material extending from the ground ring in a spiral pattern along the external surface of the cylindrical pipe, the helical ground plane being located opposite the helical open shunt stub, and the helical ground plane being conductively coupled to the ground ring; and disposing a separator between the feed line and the ground ring, the separator being configured to electrically isolate the feed line from the ground ring to electrically isolate the helical T-resonator from the helical ground conductor.

2. The method of claim 1, wherein the helical open shunt stub has a length that is greater than a diameter of the cylindrical pipe.

3. The method of claim 1, wherein the helical open shunt stub has a length that is between three and five times the diameter of the cylindrical pipe.

4. The method of claim 1, wherein the spiral pattern of the helical open shunt stub comprises a complete turn about the circumference of the cylindrical pipe such that the helical open shunt stub comprises a complete turn about the circumference of the cylindrical pipe.

5. The method of claim 1, wherein the spiral pattern of the helical ground plane comprises a complete turn about the circumference of the cylindrical pipe such that the helical open ground plane comprises a complete turn about the circumference of the cylindrical pipe.

6. The method of claim 1, wherein the feed line has a length that is the same or greater than a width of the helical open shunt stub.

7. The method of claim 1, wherein the ground ring has a width that is the same or greater than a width of the feed line.

8. The method of claim 1, wherein the separator has a width that is the same or greater than a width of the feed line, and a length that is the same or greater than a length of the feed line.

9. The method of claim 1, wherein the helical ground plane has a width corresponding to an average of a first width associated with a minimum resonant frequency for oil and a second width associated with a minimum resonant frequency for water.

10. The method of claim 1,
wherein the helical T-resonator comprises a dual helical T-resonator, and forming the helical T-resonator further comprises:
disposing, on the external surface of the cylindrical pipe, a second helical open shunt stub comprising a conductive material extending from the feed line in a direction opposite the helical open shunt stub and in a spiral pattern along the external surface of the cylindrical pipe, the second helical open shunt stub being conductively coupled to the feed line, and
wherein the helical ground conductor comprises a dual helical ground conductor, and forming the helical T-resonator further comprises:
disposing, on the external surface of the cylindrical pipe, a second helical ground plane comprising a conductive material extending from the ground ring in a direction opposite the helical ground plane and in a spiral pattern along the external surface of the cylindrical pipe, the second helical ground plane being conductively coupled to the ground ring, and the second helical ground plane being located opposite the second helical open shunt stub.

11. The method of claim 1, wherein the helical T-resonator comprises:
an input terminal located at a first end of the feed line, wherein the input terminal is configured to receive source signals from an external circuit; and
an output terminal located at a second end of the feed line, wherein the output terminal is configured to provide for sensing, by an external circuit, of response signals corresponding to the source signals.

12. The method of claim 11,
wherein a resonant frequency of the water-cut sensor is determined based on the source signals and the response signals, and
wherein a water-cut of fluid in the cylindrical pipe is determined based on the resonant frequency of the water-cut sensor.

13. The method of claim 1,
wherein disposing the helical open shunt stub on the external surface of the cylindrical pipe comprises:
disposing a first mask on the external surface of the cylindrical pipe, the first mask comprising a first opening at a first portion of the external surface of the cylindrical pipe for forming the helical open shunt stub; and
disposing a conductive material into the first opening to form the helical open shunt stub on the first portion of the external surface of the cylindrical pipe;
wherein disposing the helical ground plane on the external surface of the cylindrical pipe comprises:
disposing a second mask on the external surface of the cylindrical pipe, the second mask comprising a second opening at a second portion of the external surface of the cylindrical pipe for forming the helical ground plane; and
disposing a conductive material into the second opening to form the helical ground plane on the second portion of the external surface of the cylindrical pipe;
wherein disposing the ground ring on the external surface of the cylindrical pipe comprises:
disposing a third mask on the external surface of the cylindrical pipe, the third mask comprising a third opening at a third portion of the external surface of the cylindrical pipe for forming the ground ring; and
disposing a conductive material into the third opening to form the ground ring on the third portion of the external surface of the cylindrical pipe; and
wherein disposing the feed line on the external surface of the cylindrical pipe comprises:
disposing a fourth mask on the external surface of the cylindrical pipe, the fourth mask comprising a fourth opening at an external surface of the dielectric separator for forming the feed line of the helical T-resonator; and
disposing the fourth conductive material into the fourth opening to form the feed line on the external surface of the dielectric separator.

14. A method for manufacturing a water-cut sensor system, the method comprising:
disposing a first conductive material on a first portion of an external surface of a cylindrical pipe to form a helical open shunt stub of a helical T-resonator of a water-cut sensor, the helical open shunt stub extending in a spiral pattern along the external surface of the cylindrical pipe;
disposing a second conductive material on a second portion of the external surface of the cylindrical pipe to form a helical ground plane of a helical ground conductor of the water-cut sensor, the helical ground plane extending in a spiral pattern along the external surface of the cylindrical pipe, and the helical ground plane being located opposite the helical open shunt stub such that fluid flow in the cylindrical pipe is configured to flow between the helical ground plane and the helical open shunt stub;

disposing a third conductive material on a third portion of the external surface of the cylindrical pipe to form a ground ring of the helical ground conductor of the water-cut sensor, the ground ring extending in a circumferential direction about the external surface of the cylindrical pipe, and the ground ring being conductively coupled to the helical ground plane;

disposing a dielectric separator on at least a portion of the ground ring to be overlapped by a feed line of the helical T-resonator of the water-cut sensor; and disposing a fourth conductive material on an external surface of the dielectric separator to form a feed line of the helical T-resonator of the water-cut sensor, the feed line overlapping the portion of the ground ring, and the feed line being conductively coupled to the helical open shunt stub.

15. The method of claim 14, wherein the helical open shunt stub has a length that is greater than a diameter of the cylindrical pipe.

16. The method of claim 14, wherein the helical open shunt stub has a length that is between three and five times the diameter of the cylindrical pipe.

17. The method of claim 14, wherein the spiral pattern of the helical open shunt stub comprises a complete turn about the circumference of the cylindrical pipe such that the helical open shunt stub comprises a complete turn about the circumference of the cylindrical pipe.

18. The method of claim 14, wherein the spiral pattern of the helical ground plane comprises a complete turn about the circumference of the cylindrical pipe such that the helical open ground plane comprises a complete turn about the circumference of the cylindrical pipe.

19. The method of claim 14, wherein the feed line has a length that is the same or greater than a width of the helical open shunt stub.

20. The method of claim 14, wherein the ground ring has a width that is the same or greater than a width of the feed line.

21. The method of claim 14, wherein the dielectric separator has a width that is the same or greater than a width of the feed line, and a length that is the same or greater than a length of the feed line.

22. The method of claim 14, wherein the helical ground plane has a width corresponding to an average of a first width associated with a minimum resonant frequency for oil and a second width associated with a minimum resonant frequency for water.

23. The method of claim 14, wherein the helical T-resonator comprises a dual helical T-resonator and the helical ground conductor comprises a dual helical ground conductor, the method further comprising:

disposing a fifth conductive material on a fifth portion of the external surface of the cylindrical pipe to form a second helical open shunt stub extending from the feed line in a direction opposite the helical open shunt stub and in a spiral pattern along the external surface of the cylindrical pipe, the second helical open shunt stub being conductively coupled to the feed line; and disposing a sixth conductive material on a sixth portion of the external surface of the cylindrical pipe to form a second helical ground plane extending from the ground ring in a direction opposite the helical ground plane and in a spiral pattern along the external surface of the cylindrical pipe, the second helical ground plane being conductively coupled to the ground ring, and the second helical ground plane being located opposite the second helical open shunt stub.

24. The method of claim 14, wherein the helical T-resonator comprises:

an input terminal located at a first end of the feed line, wherein the input terminal is configured to receive source signals from an external circuit; and an output terminal located at a second end of the feed line, wherein the output terminal is configured to provide for sensing, by an external circuit, of response signals corresponding to the source signals.

25. The method of claim 24,
wherein a resonant frequency of the microwave resonator water-cut sensor is determined based on the source signals and the response signals, and
wherein a water-cut of fluid in the cylindrical pipe is determined based on the resonant frequency of the microwave resonator water-cut sensor.

26. The method of claim 14,
wherein disposing a first conductive material on a first portion of an external surface of a cylindrical pipe to form the helical open shunt stub comprises:
  disposing a first mask on the external surface of the cylindrical pipe, the first mask comprising a first opening at the first portion of the external surface of the cylindrical pipe for forming the helical open shunt stub; and
  disposing the first conductive material into the first opening to form the helical open shunt stub on the first portion of the external surface of the cylindrical pipe,
wherein disposing the second conductive material on a second portion of the external surface of the cylindrical pipe to form the helical ground plane comprises:
  disposing a second mask on the external surface of the cylindrical pipe, the second mask comprising a second opening at the second portion of the external surface of the cylindrical pipe for forming the helical ground plane, and the second portion of the external surface of the cylindrical pipe being opposite the first portion of the external surface of the cylindrical pipe; and
  disposing the second conductive material into the second opening to form the helical ground plane on the second portion of the external surface of the cylindrical pipe,
wherein disposing a third conductive material on a third portion of the external surface of the cylindrical pipe to form the ground ring comprises:
  disposing a third mask on the external surface of the cylindrical pipe, the third mask comprising a third opening at the third portion of the external surface of the cylindrical pipe for forming the ground ring, and the third portion extending at least from the ground plane about a circumference of the cylindrical pipe; and
  disposing the third conductive material into the third opening to form the ground ring on the third portion of the external surface of the cylindrical pipe, the ground ring being conductively coupled to the helical ground plane; and
wherein disposing a fourth conductive material on an external surface of the dielectric separator to form a feed line comprises,
  disposing a fourth mask on the external surface of the cylindrical pipe, the fourth mask comprising a fourth opening at an external surface of the dielectric separator for forming the feed line of the helical T-resonator; and disposing the fourth conductive material into the fourth opening to form the feed line on the external surface of the dielectric separator, the feed line being conductively coupled to the helical open shunt stub.

27. A method for manufacturing a water-cut sensor, the method comprising:

disposing a first mask on an external surface of a cylindrical pipe, the first mask comprising a first opening at a first portion of the external surface of the cylindrical pipe for forming a helical open shunt stub of a helical T-resonator;

disposing a first conductive material into the first opening to form the helical open shunt stub of the helical T-resonator on the first portion of the external surface of the cylindrical pipe;

disposing a second mask on the external surface of the cylindrical pipe, the second mask comprising a second opening at a second portion of the external surface of the cylindrical pipe for forming a helical ground plane of a helical ground conductor, and the second portion of the external surface of the cylindrical pipe being opposite the first portion of the external surface of the cylindrical pipe;

disposing a second conductive material into the second opening to form the helical ground plane of the helical ground conductor on the second portion of the external surface of the cylindrical pipe;

disposing a third mask on an external surface of the cylindrical pipe, the third mask comprising a third opening at a third portion of the external surface of the cylindrical pipe for forming a ground ring of the helical ground conductor, and the third portion extending at least from the ground plane about a circumference of the cylindrical pipe;

disposing a third conductive material into the third opening to form the ground ring of the helical ground conductor on the third portion of the external surface of the cylindrical pipe, the ground ring being conductively coupled to the helical ground plane;

disposing a dielectric separator on at least a portion of the ground ring to be overlapped by a feed line of the helical T-resonator;

disposing a fourth mask on an external surface of the cylindrical pipe, the fourth mask comprising a fourth opening at an external surface of the dielectric separator for forming the feed line of the helical T-resonator; and disposing a fourth conductive material into the fourth opening to form the feed line of the helical T-resonator on the external surface of the dielectric separator, the feed line being conductively coupled to the helical open shunt stub.

* * * * *